United States Patent
Gordon et al.

(10) Patent No.: US 8,795,333 B2
(45) Date of Patent: Aug. 5, 2014

(54) METHOD AND APPARATUS FOR REPAIRING A TENDON OR LIGAMENT

(76) Inventors: Leonard Gordon, Mill Valley, CA (US); Shawn T Huxel, Lawrenceville, NJ (US); Mari Susan Truman, Warsaw, IN (US); Alan B. Miller, Jamison, PA (US)

( * ) Notice: Subject to any disclaimer, the term of this patent is extended or adjusted under 35 U.S.C. 154(b) by 732 days.

(21) Appl. No.: 12/716,724

(22) Filed: Mar. 3, 2010

(65) Prior Publication Data
US 2011/0202002 A1   Aug. 18, 2011
US 2013/0060190 A9   Mar. 7, 2013

Related U.S. Application Data

(63) Continuation-in-part of application No. PCT/US2008/066754, filed on Jun. 12, 2008.

(60) Provisional application No. 61/304,003, filed on Feb. 12, 2010.

(51) Int. Cl.
*A61B 17/04* (2006.01)

(52) U.S. Cl.
USPC ........ 606/232; 623/13.14; 606/228; 606/144; 606/148

(58) Field of Classification Search
USPC .................. 623/13.11, 13.13; 606/228, 232
See application file for complete search history.

(56) References Cited

U.S. PATENT DOCUMENTS

| | | | |
|---|---|---|---|
| 4,979,956 A | 12/1990 | Silvestrini | |
| 5,480,408 A | 1/1996 | Chow | |
| 5,486,197 A | 1/1996 | Le et al. | |
| 5,645,568 A | 7/1997 | Chervitz et al. | |
| 5,683,389 A | 11/1997 | Orsak | |
| 5,741,260 A | 4/1998 | Songer et al. | |
| 6,102,947 A * | 8/2000 | Gordon | 623/13.11 |
| 6,132,433 A * | 10/2000 | Whelan | 606/916 |
| 6,342,060 B1 * | 1/2002 | Adams | 606/151 |
| 6,626,916 B1 | 9/2003 | Yeung et al. | |
| 6,773,450 B2 | 8/2004 | Leung et al. | |
| 6,984,241 B2 | 1/2006 | Lubberts et al. | |
| 7,279,008 B2 * | 10/2007 | Brown et al. | 623/13.15 |

(Continued)

FOREIGN PATENT DOCUMENTS

| | | |
|---|---|---|
| KR | 1020060027231 | 4/2006 |
| WO | 2006045809 | 5/2006 |
| WO | 2009151453 | 12/2009 |

OTHER PUBLICATIONS

International Search Report and Written Opinion issued May 10, 2011 in PCT/US2011/024476.

(Continued)

*Primary Examiner* — Corrine M McDermott
*Assistant Examiner* — Alexander Orkin
(74) *Attorney, Agent, or Firm* — Law Office of Sergei Orel, LLC

(57) ABSTRACT

A method and apparatus for reattaching the opposed ends of a member, such as a tendon, ligament or bone, during preparing and healing of the member using a surgical repair device that can be securely attached to the member and then safely guided through tortuous anatomy for reattachment and repair. The repair device further includes structural means so as to secure opposed ends of the member against separation during healing. Devices for aiding in the positioning of the surgical repair device are provided.

14 Claims, 43 Drawing Sheets

(56) References Cited

U.S. PATENT DOCUMENTS

| | | | |
|---|---|---|---|
| 2001/0014825 A1* | 8/2001 | Burke et al. | 623/13.14 |
| 2003/0120278 A1* | 6/2003 | Morgan et al. | 606/73 |
| 2005/0245958 A1 | 11/2005 | Carlson et al. | |
| 2010/0137883 A1* | 6/2010 | Gonzalez-Hernandez | 606/138 |

OTHER PUBLICATIONS

International Search Report dated May 25, 2009 of PCT/US2008/066754.

International Preliminary Report on Patentability of PCT/US2008/066754, dated Dec. 13, 2010.

McDonald et al., "Mechanical Properties of a New Stainless Steel Suture for Use in Flexor Tendon Repair: Comparison with Current Suture Materials", ASME Summer Bioengineering Conference, Naples, Florida, Jun. 16-19, 2010.

McDonald et al., "In Situ Comparison of a New Flexor Tendon Repair using Multifilament Stainless Steel Suture with the Savage Technique", Orthopaedic Research Study, New Orleans, LA, Mar. 6-9, 2010.

Vianna et al., "Mechanical Comparison of Two Knots and Two Crimp Systems for Securing Nylon Line Used for Extra-Articular Stablization of the Canine Stifle", Veterinary Surgery, vol. 35, pp. 567-572, 2006.

Anderson, et al., "Biomechanical Evaluation of a Crimp Clamp System for Loop Fixation of Monofilament Nylon Leader Material Used for Stabilization of the Canine Stifle Joint", Veterinary Surgery, vol. 27, pp. 533-539, 1998.

Banwell et al., "In Vitro Evaluation of the 18 and 36kg Securos Cranial Cruciate Ligament Repair System", Veterinary Surgery, vol. 34, pp. 283-288, 2005.

Cabano et al., "Mechanical Comparison of Two Suture Constructs for Extra-Capsular Stifle Stabilization", Veterinary Surgery, vol. 40, pp. 334-339, 2011.

Crockard, "Evaluation of Spinal Laminar Fixation by a New, Flexible Stainless Steel Cable", Neurosurgery, vol. 35 (5), Nov. 1994, pp. 892-898.

Dall, et al., "Re-Attachment of the Great Trochanter—The Use of the Trachanter Cable-Grip System", The Journal of Bone and Joint Surgery, vol. 65-B, No. 1, Jan. 1983, pp. 55-59.

Dickman, et al., "Comparative Mechanical Properties of Spinal Cable and Wire Fixation Systems", Spine, vol. 22(6), Mar. 15, 1997, pp. 596-604; Abstract only.

Finn et al., "Surgical Treatment of Occipitocervical Instability", Neurosurgery, vol. 63, No. 5, Nov. 2008, pp. 961-969.

Huhn, et al., "Posterior Spinal Osteosynthesis for Cervical Fracture/Dislocation Using a Flexible Multistrand Cable System: Technical Note", Neurosurgery, vol. 29, No. 6, 1991, pp. 943-946.

Hurlbert, et al., "A biomechanical evaluation of occipitocerival instrumentation: screw compared with wire fixation", J. Neurosurg: Spine, vol. 90, Jan. 1999, pp. 84-90.

Moores, et al., "Mechanical Evaluation of Two Crimp Clamp Systems for Extracapsular Stabilization of the Cranial Cruciate Ligament-Deficient Canine Stifle", Veterinary Surgery, vol. 35, 2006, pp. 470-475.

Moores, et al., "Mechanical Evaluation of Two Loop Tensioning Methods for Crimp Clamp Extracapsular Stabilization of the Cranial Cruciate Ligament-Deficient Canine Stifle", Veterinary Surgery, vol. 35, 2006, pp. 476-479.

Ramond C. Read, "Milestones in the history of hernia surgery: Prosthetic repair", Hernia, vol. 8, 2004, pp. 8-14.

Sicard, et al., "Evaluation of 5 Types of Fishing Material, 2 Sterilization Methods, and a Crimp-Claim System for Extra-articular Stabilization of the Canine Stifle Joint", Veterinary Surgery, vol. 31, 2002, pp. 78-84.

Songer et al., "Repair of the Pars Interarticularis Defect with a Cable-Screw Construct: A Preliminary", Spine, vol. 23 (2), Jan. 15, 1998, pp. 263-269.

Songer et al., "The Use of Sublaminar Cables to Replace Luque Wires", Spine, vol. 16, No. 8 Supplement, 1991, pp. S418-S421.

Takahira et al., "Reattachment of the greater trochanter in total hip arthroplasty: the pin-sleeve system compared with the Dall-Miles cable grip system", International Orthopaedics, vol. 34, 2010, pp. 793-797.

Burgess et al., "In Vitro Biomechanical Evluation and Comparison of FiberWire, FiberTape, OrthoFiber, and Nylon Leader Line for Potential Use During Extraarticlar Stabilization of Canine Cruciate Deficient Stifles" Veterinary Surgery, vol. 39, 2010, pp. 208-215.

* cited by examiner

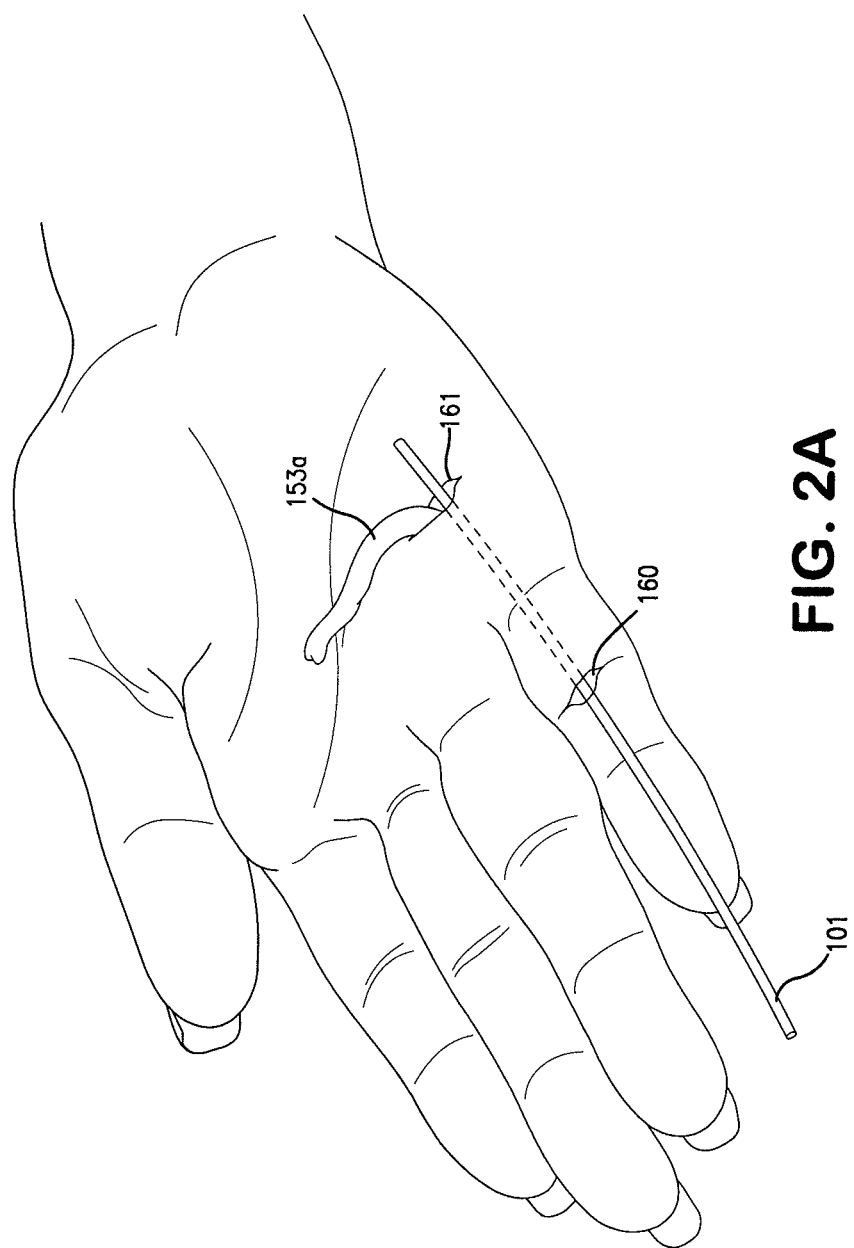

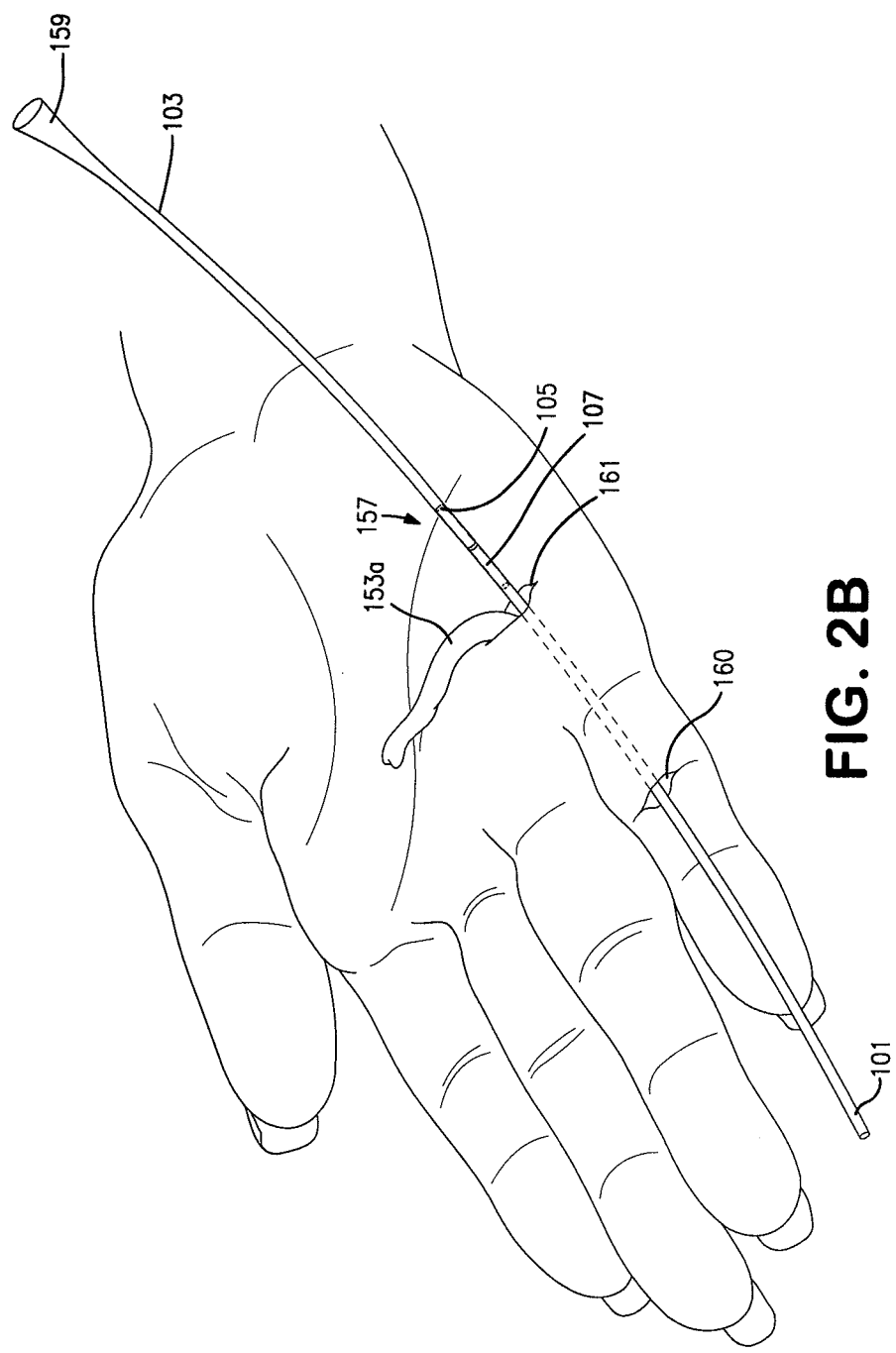

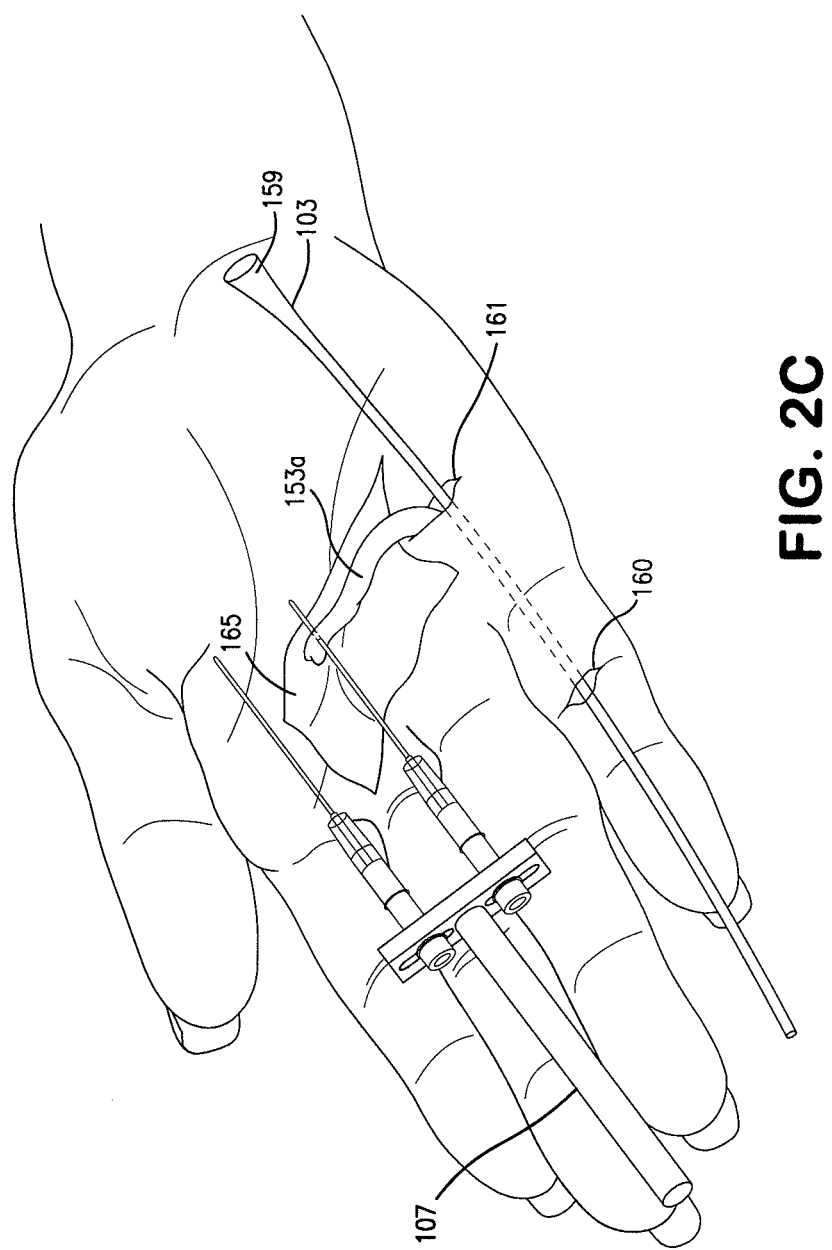

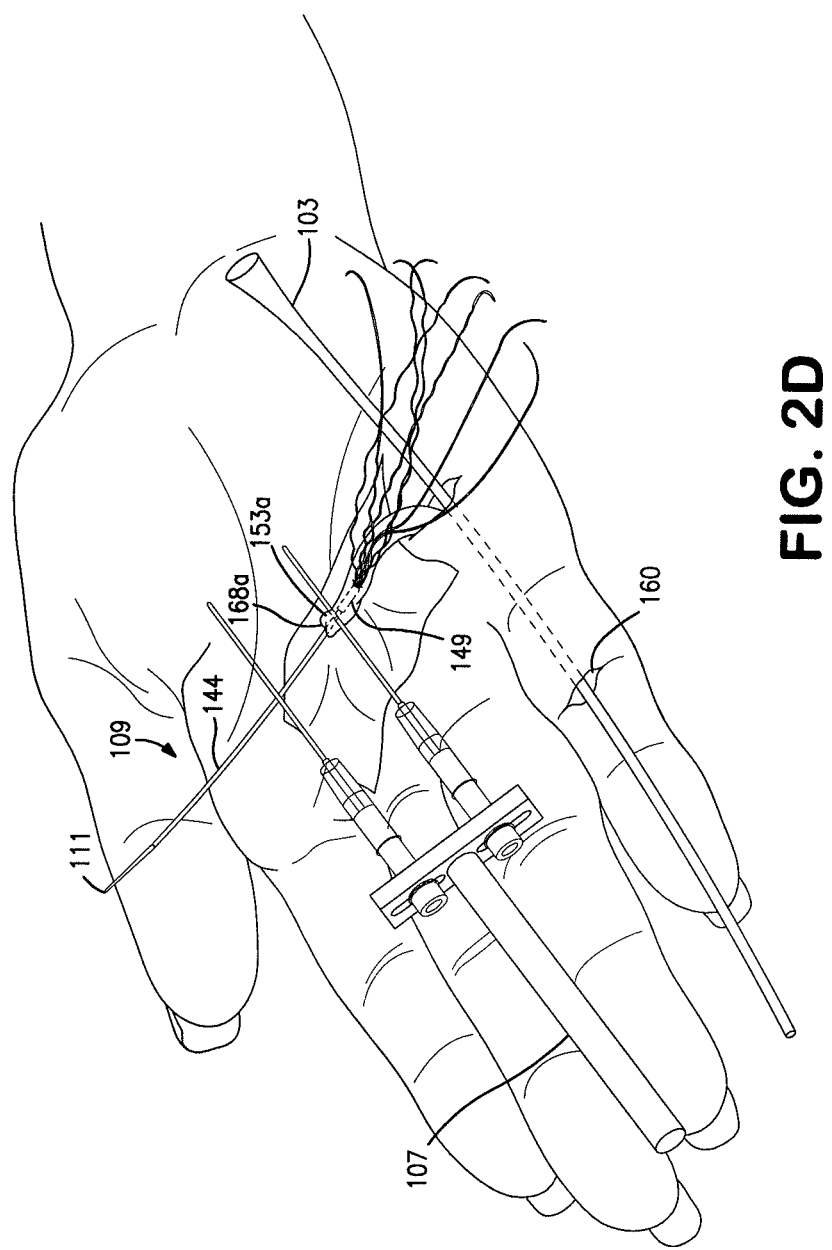

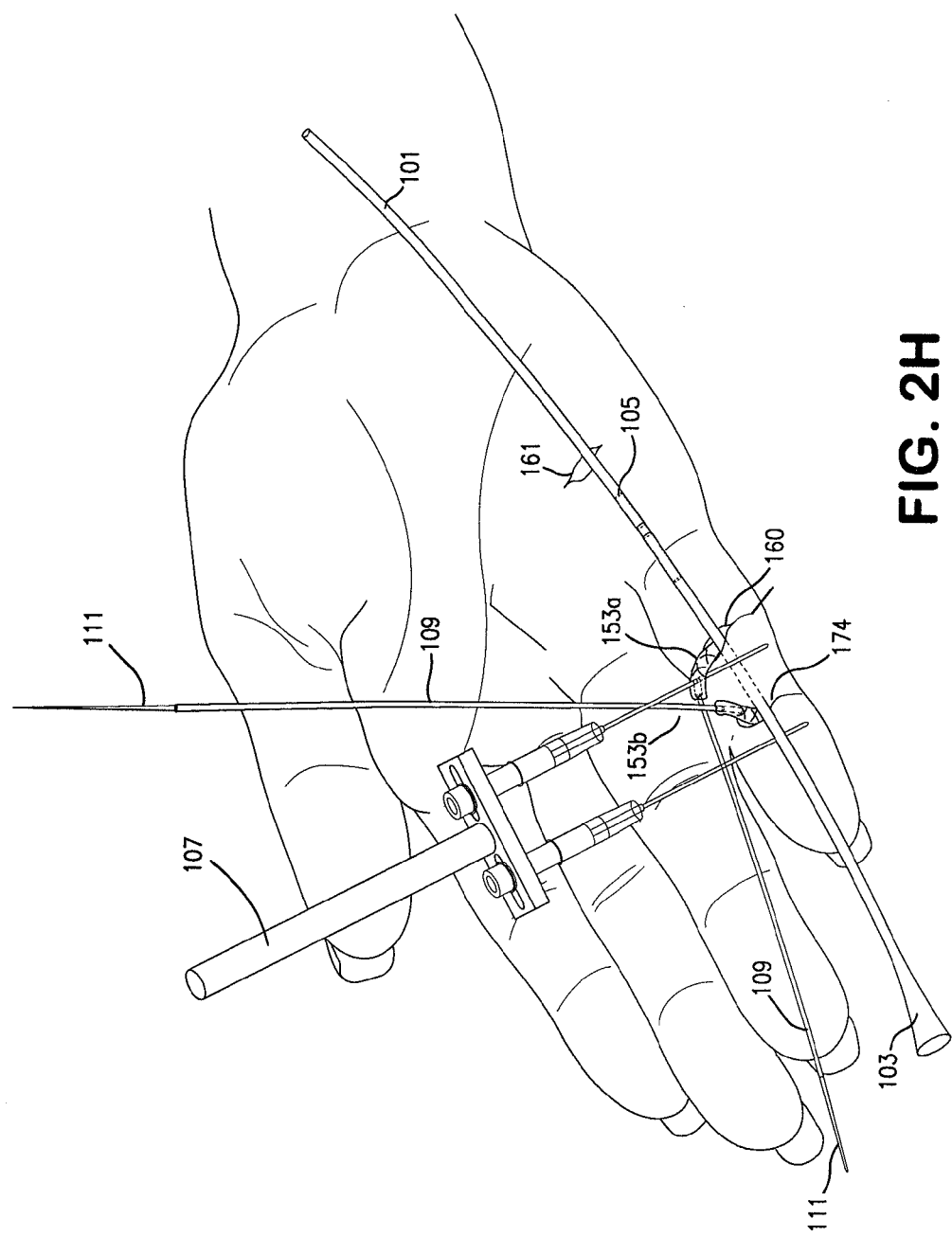

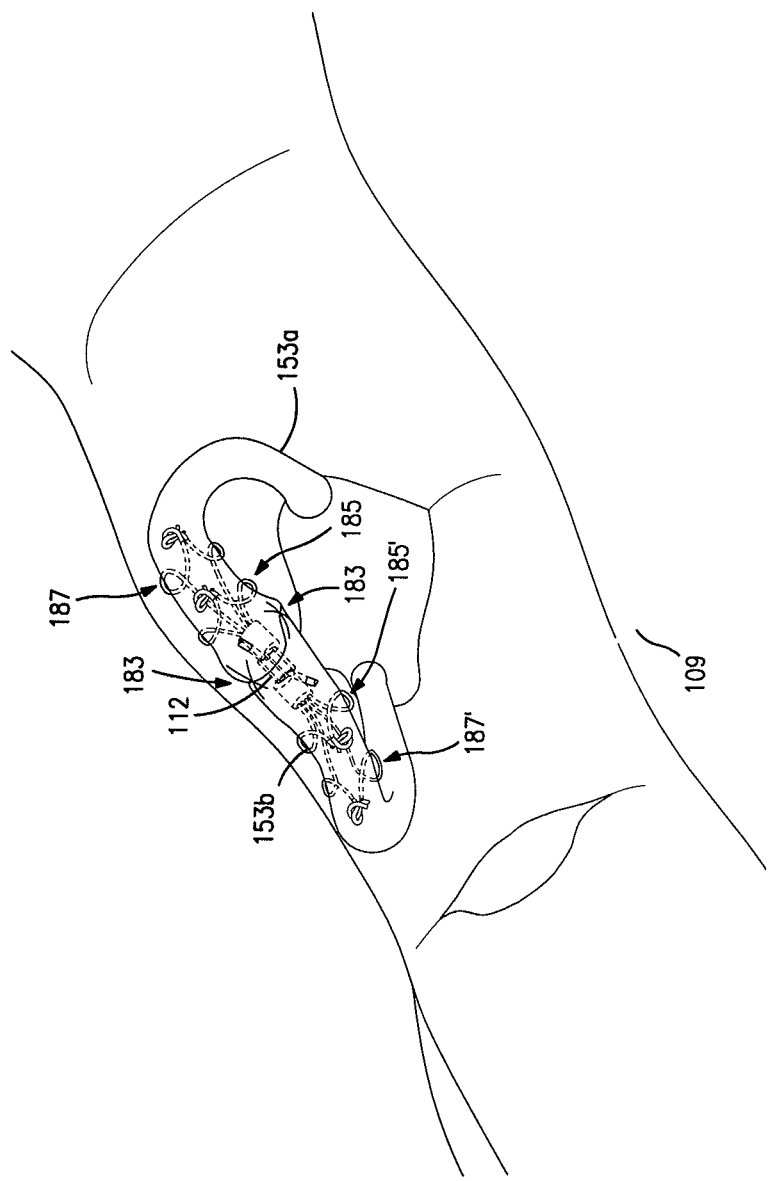

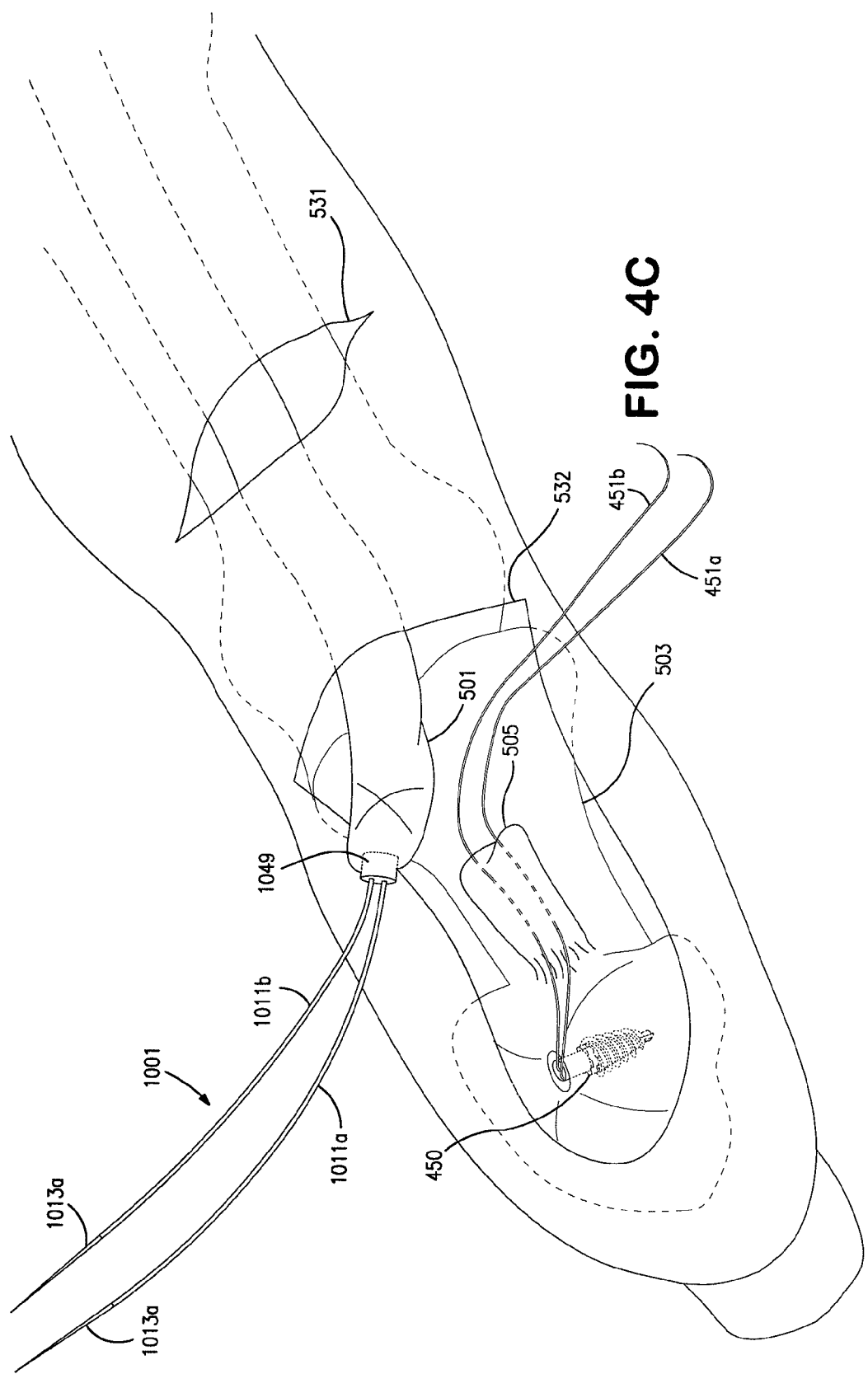

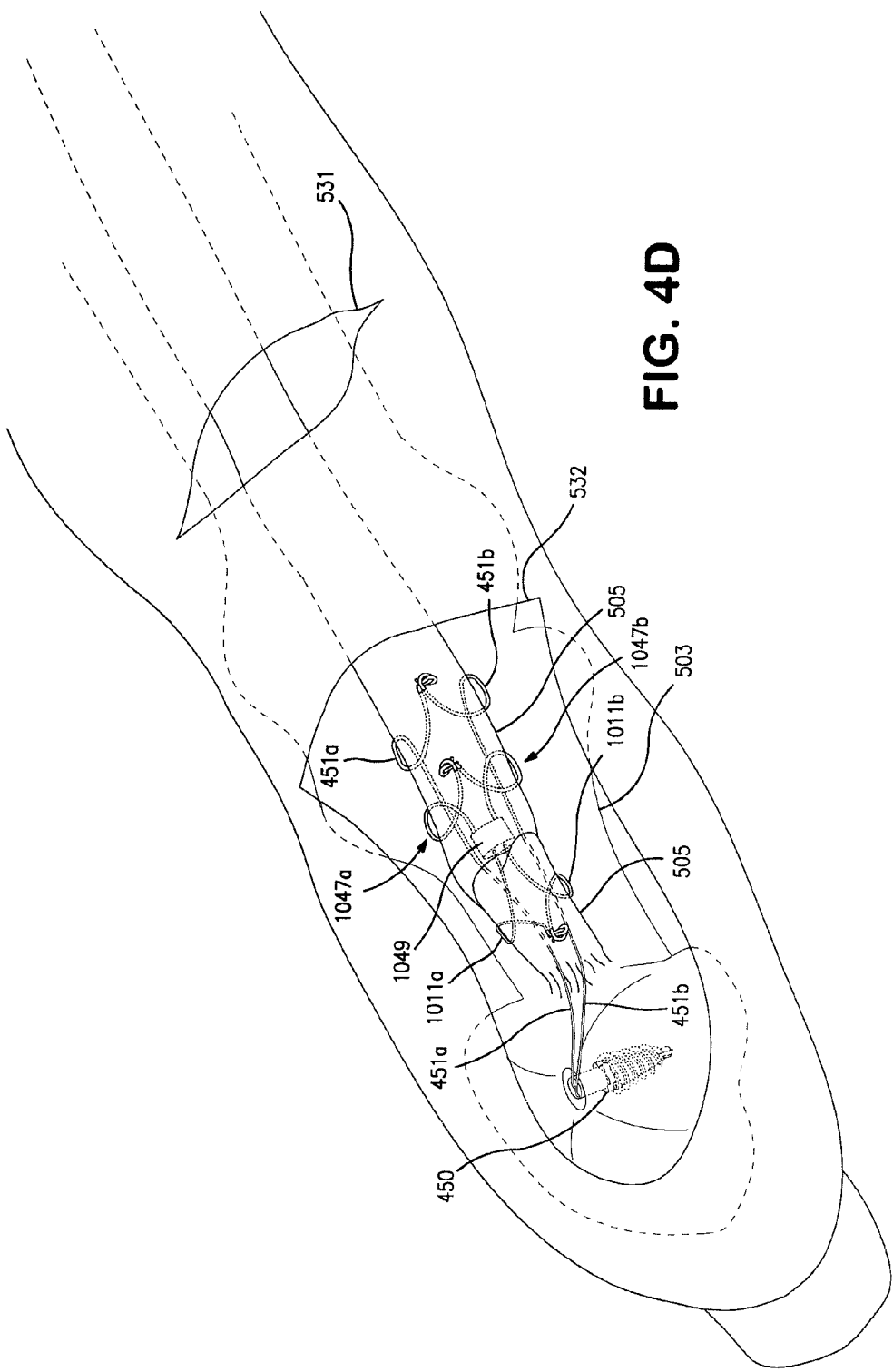

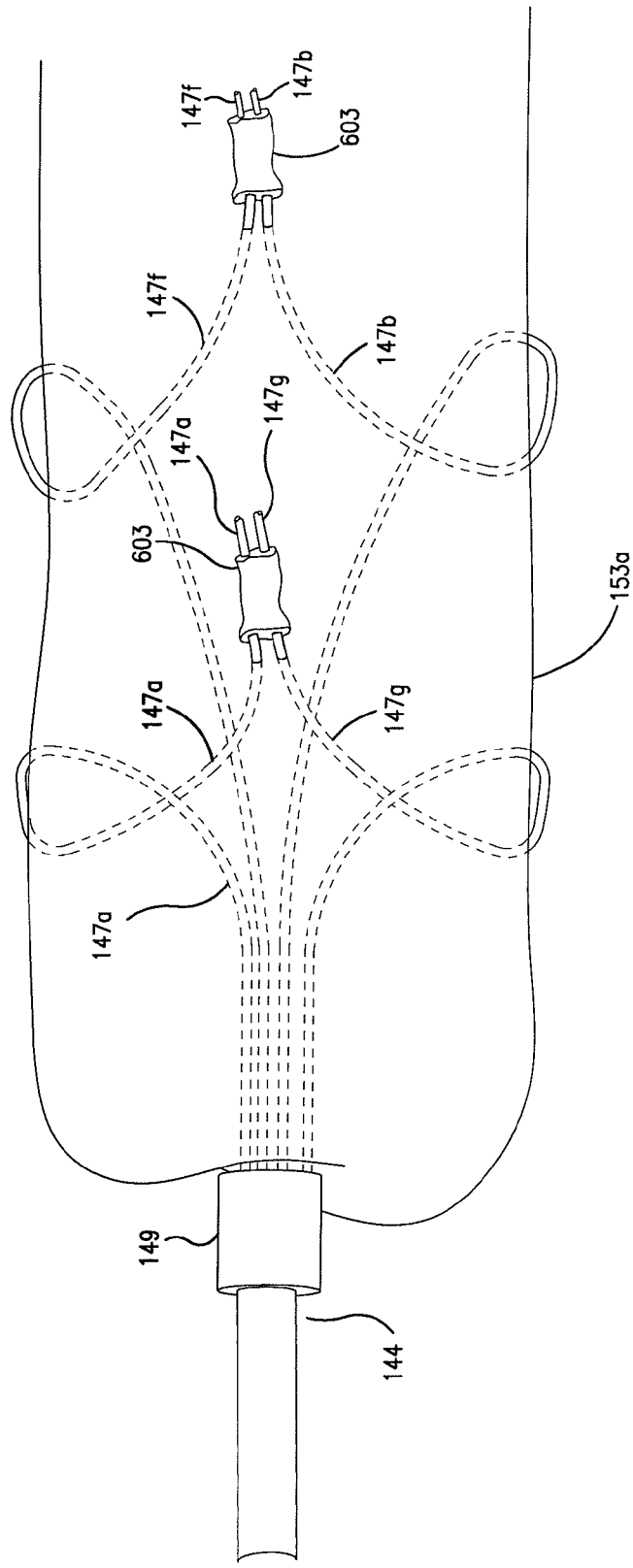

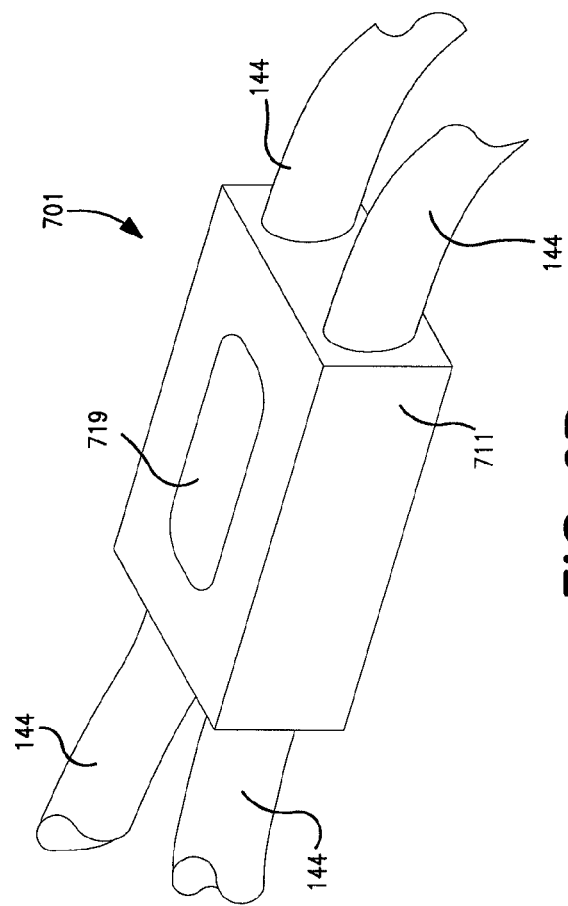
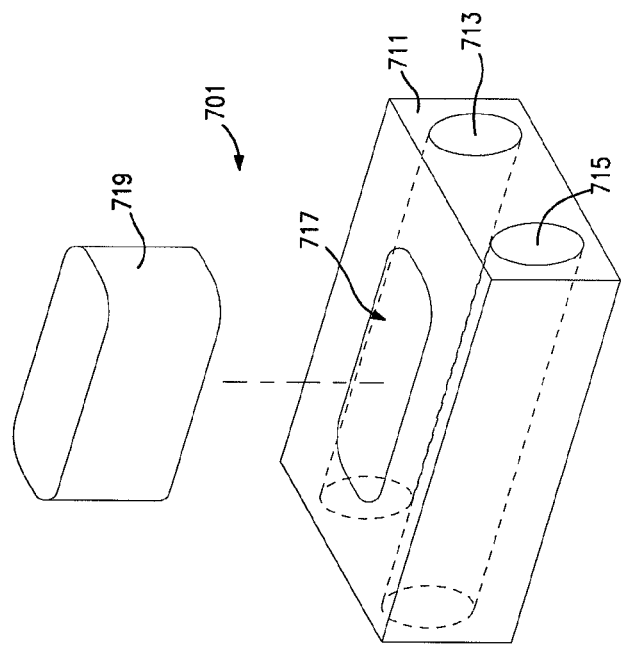
FIG. 6B
FIG. 6A

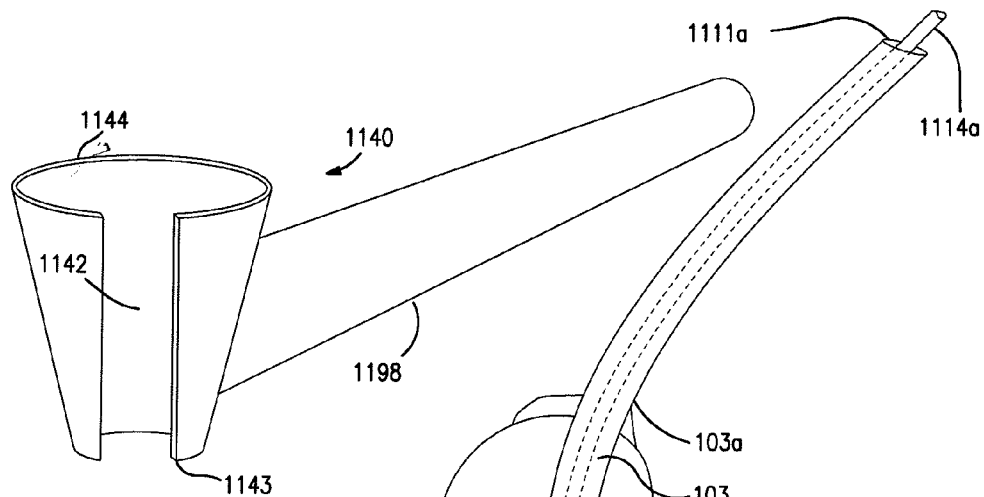
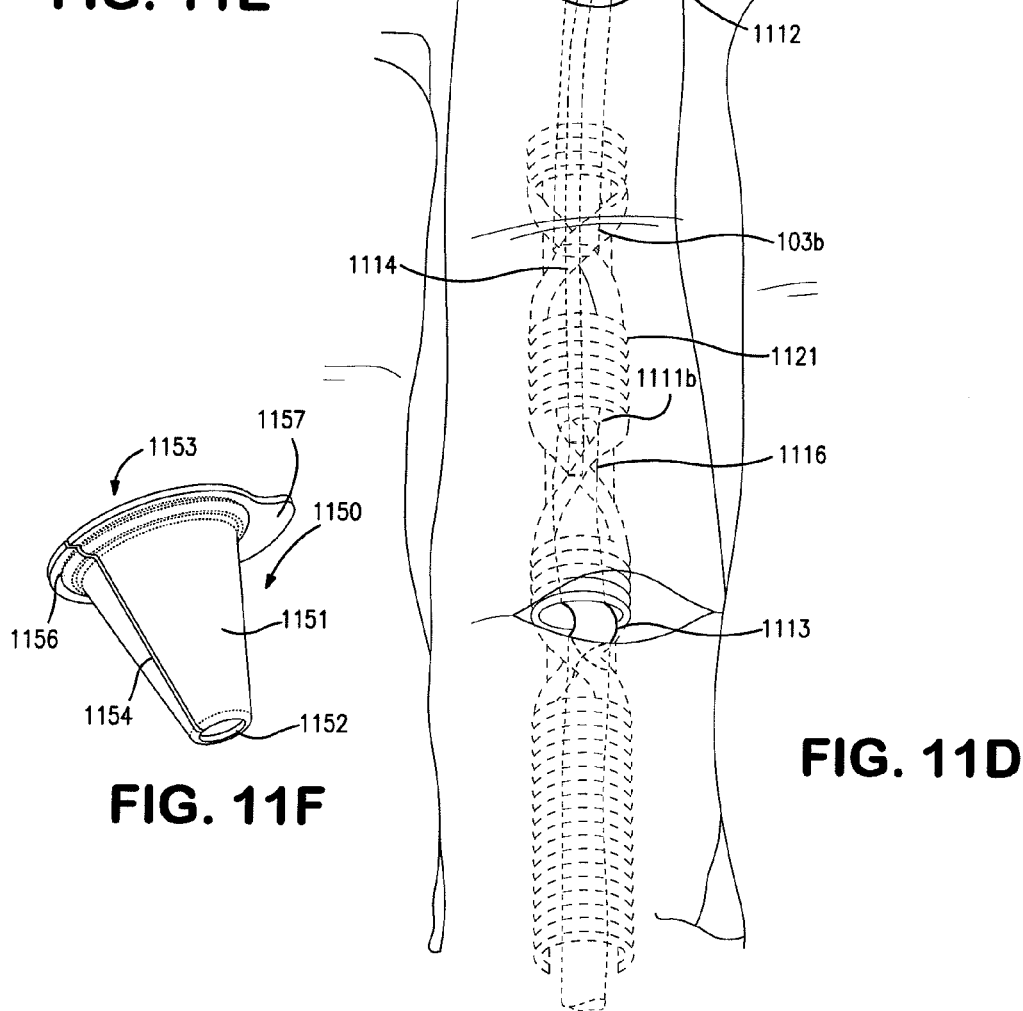
FIG. 11E
FIG. 11F
FIG. 11D

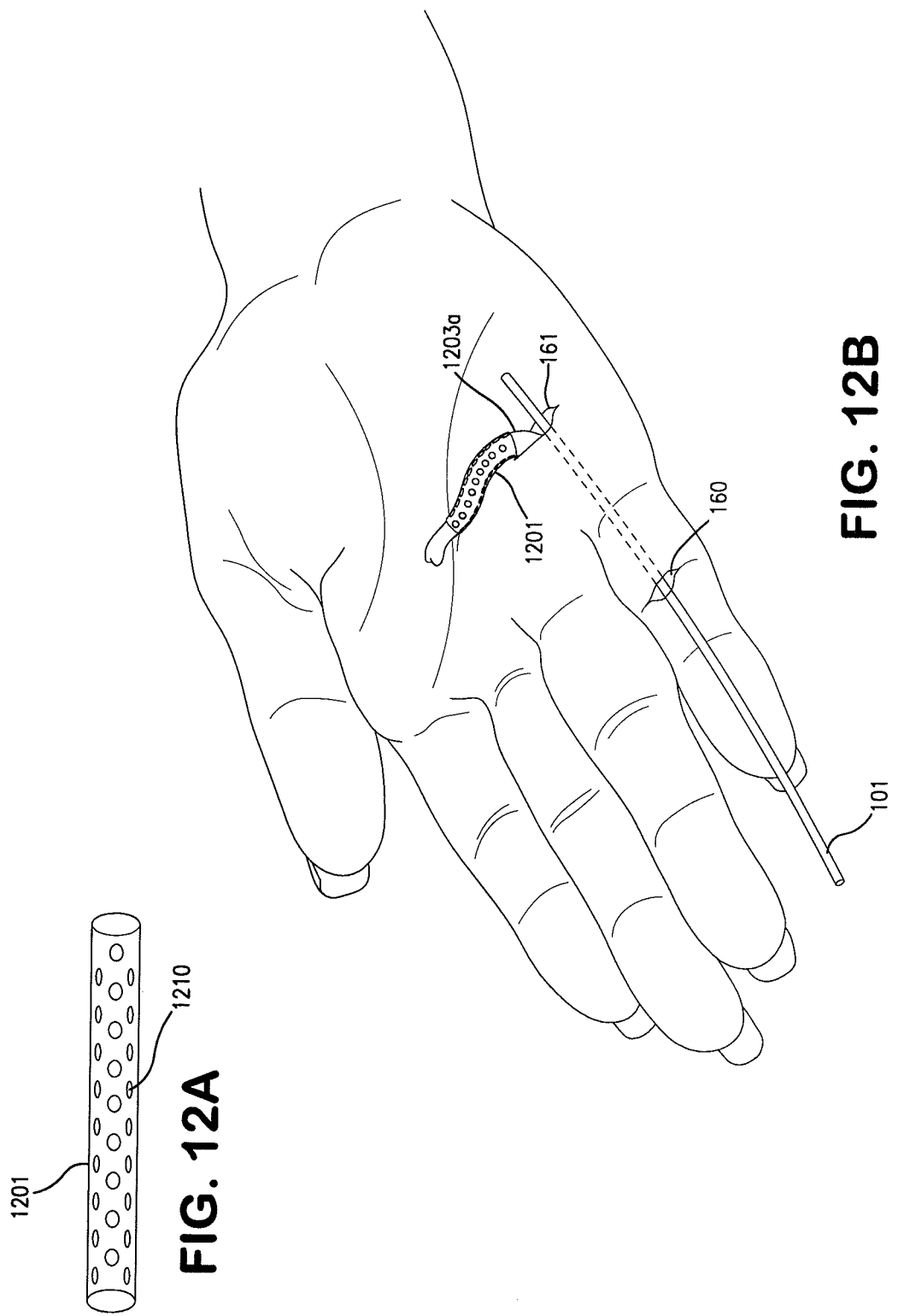

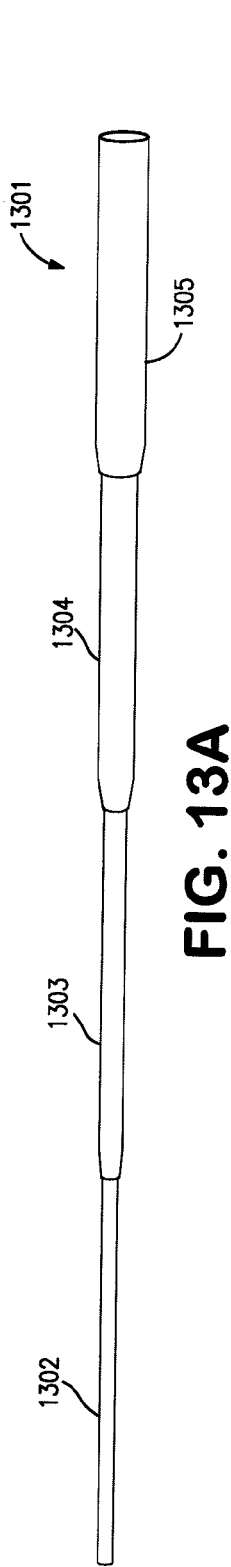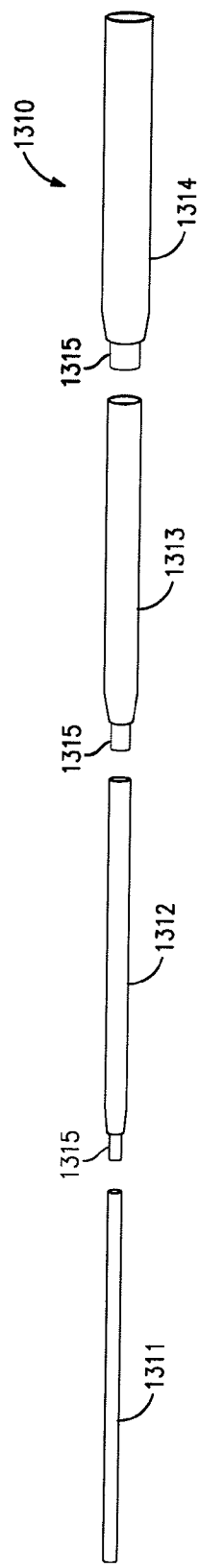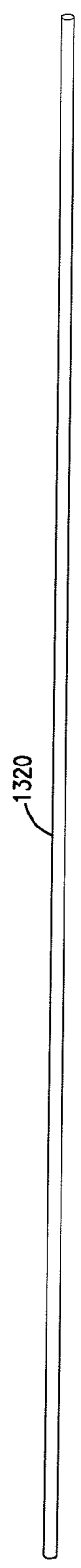
FIG. 13A
FIG. 13B
FIG. 13C

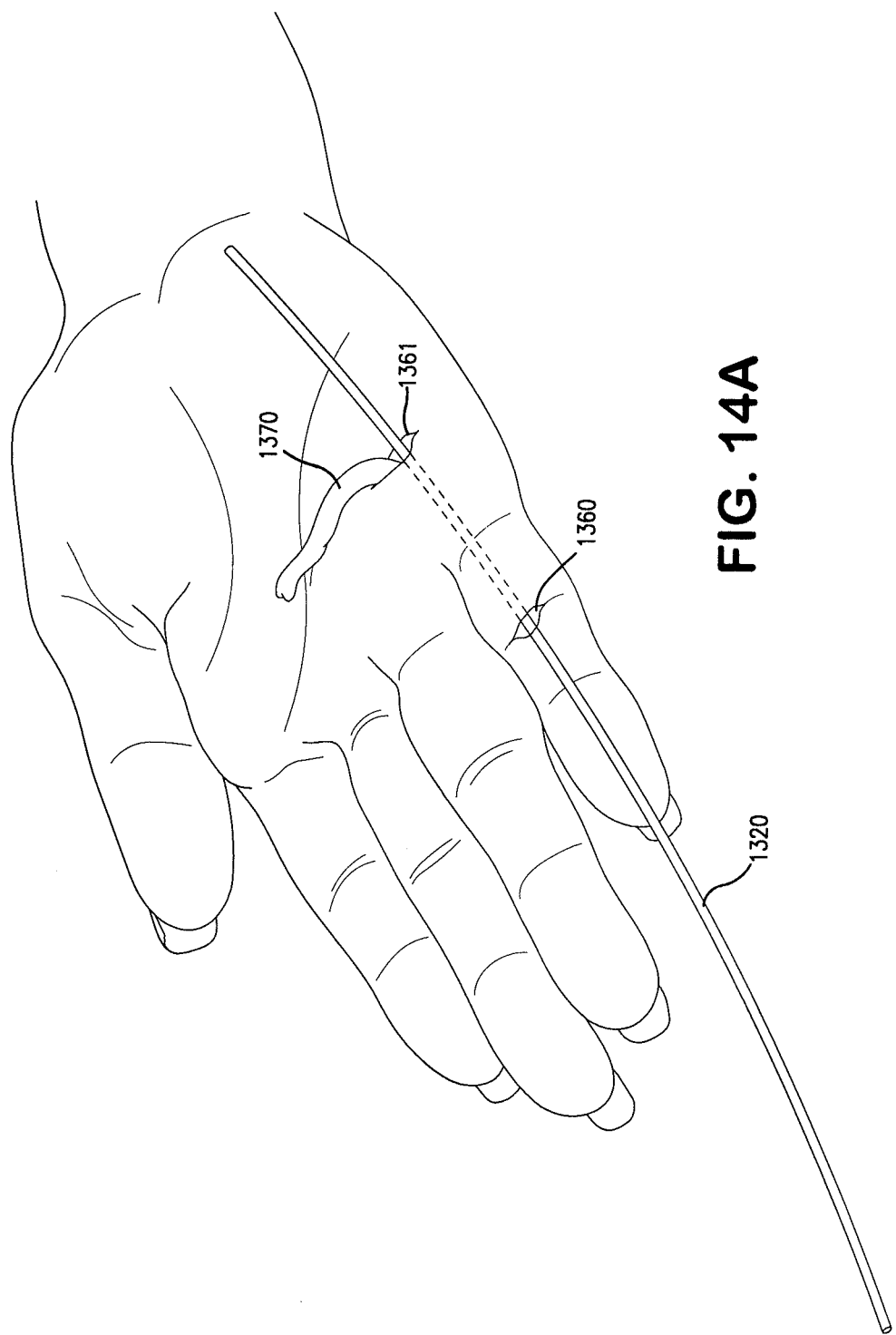

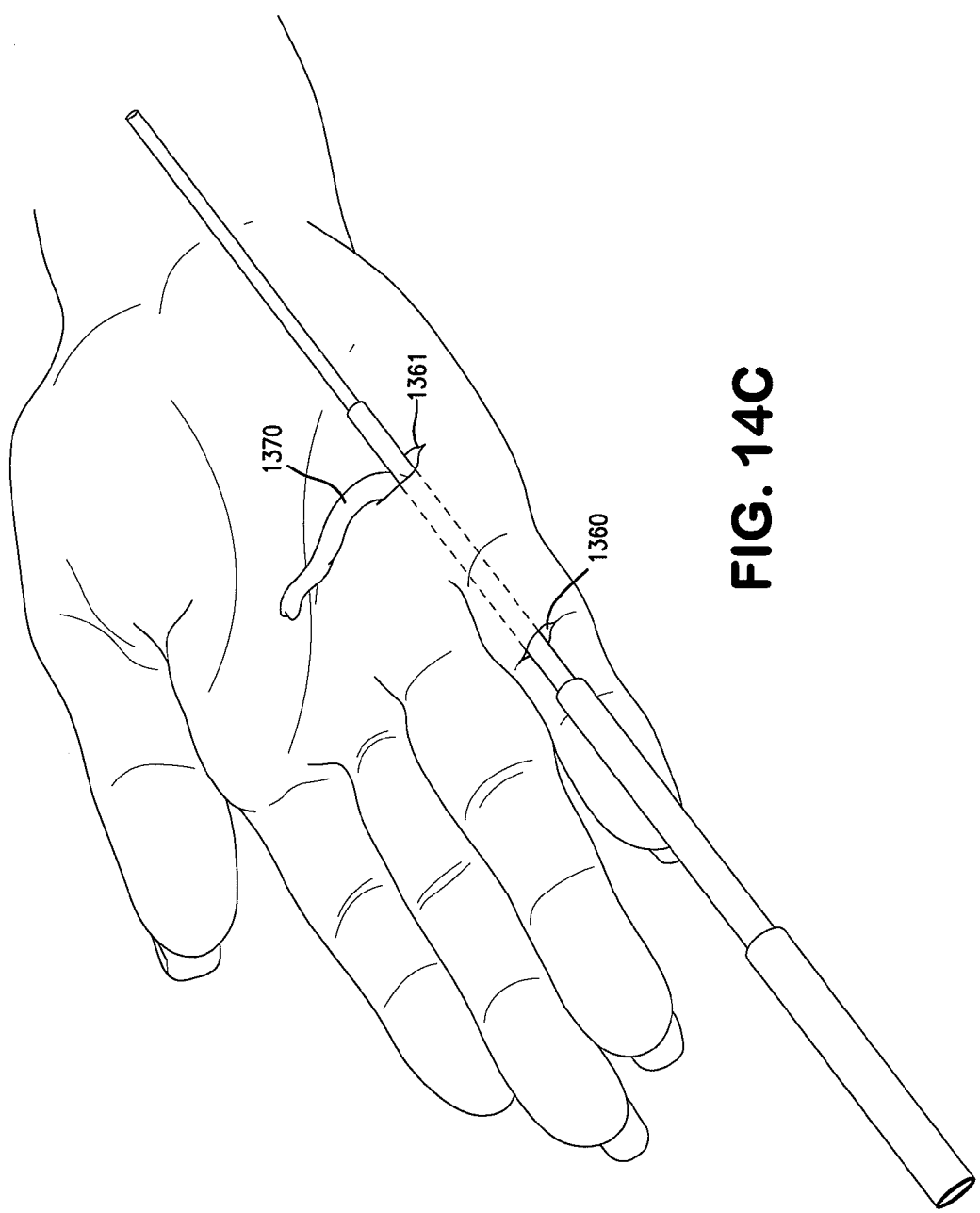

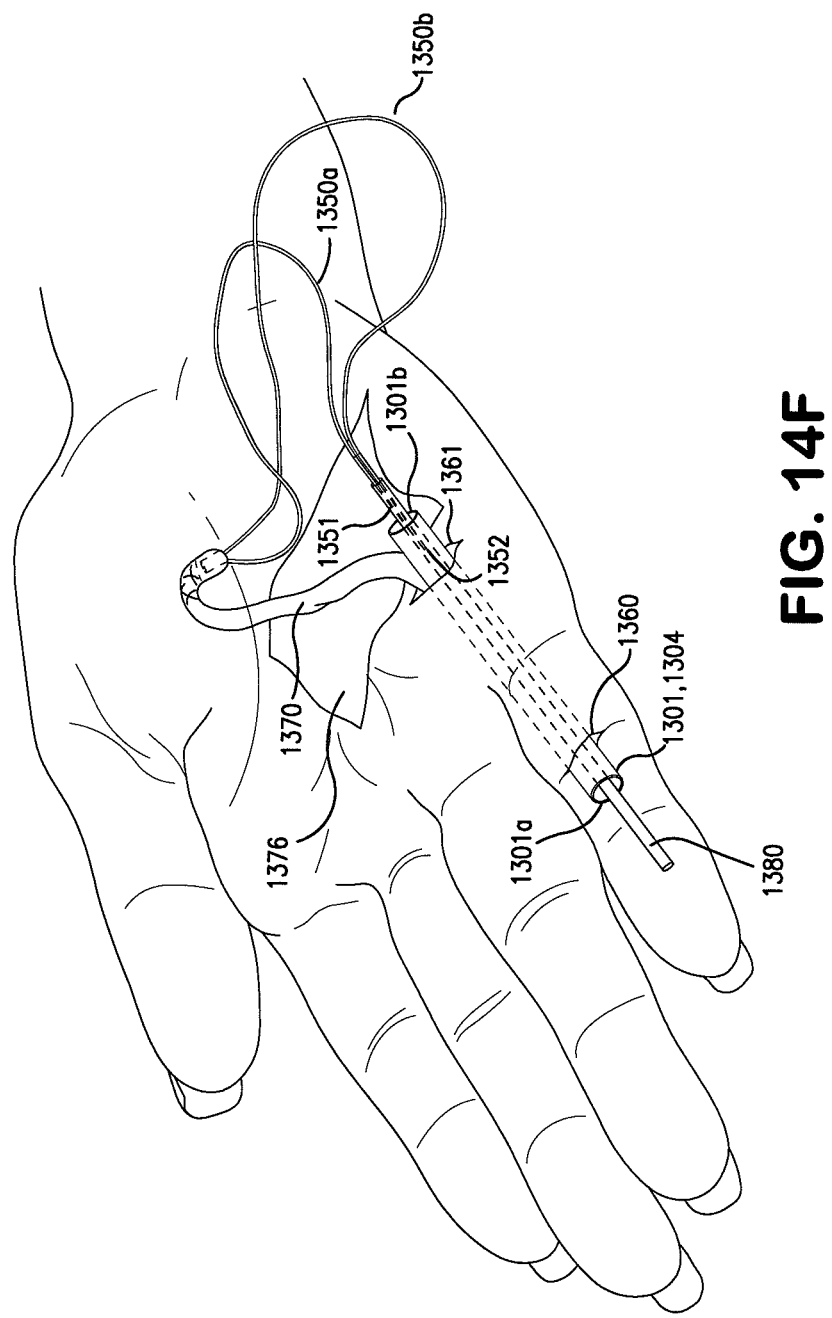

METHOD AND APPARATUS FOR REPAIRING A TENDON OR LIGAMENT

CROSS-REFERENCE TO RELATED APPLICATIONS

This application claims priority to provisional patent Application No. 61/304,003, filed Feb. 12, 2010, the disclosure of which is hereby incorporated herein by reference.

FIELD OF THE INVENTION

The invention pertains to methods and apparatus for repairing tendons, ligaments, and the like. More particularly, the invention pertains to surgical implants and techniques for repairing severed or injured tendons and ligaments. It is particularly well-suited for repairing tendons and ligaments of the extremities with minimal disruption of the surrounding tissues.

BACKGROUND OF THE INVENTION

The current standard of care for repairing severed tendons in the hand is to re-attach the two separated ends of the tendon with nothing but sutures. The two ends of the tendon are held together by the suture while the tendon heals. Surgical repair of tendons and ligaments, particularly flexor tendons, has been accurately described as a technique-intensive surgical undertaking.

The repair must be of sufficient strength to prevent gapping at the apposed end faces of the repaired member to allow the member to reattach and heal as well as to permit post-repair application of rehabilitating manipulation of the repaired member. Considerable effort has been directed toward the development of various suturing techniques for this purpose. Two strand, four strand, and six strand suturing techniques, primarily using locking stitches, have been widely used. There are a wide variety of suturing patterns which have been developed in an effort to attempt to increase the tensile strength across the surgical repair during the healing process. A common suturing technique in recent times is known as the Kessler repair, which involves the use of sutures that span, in a particular configuration or pattern, across the opposed severed ends of the tendon (or ligament). Evans and Thompson, "The Application of Force to the Healing Tendon" The Journal of Hand Therapy, October-December, 1993, pages 266-282, surveys the various suturing techniques that have been employed in surgical tendon repair. Further, two articles by Strickland in the Journal of American Academy of Orthopaedic Surgeons entitled "Flexor Tendon Injuries: I. Foundations of Treatment" and "Flexor Tendon Injuries: II. Operative Technique", Volume 3, No. 1, January/February, 1995, pages 44-62, describe and illustrate various suturing techniques.

Generally, the tensile strength of a tendon repair increases with increased complexity of the suturing scheme. As set forth in the Evans and Thompson article, the loads at which failure occur across a sutured joint can vary between about 1,000 grams force to as much as about 8,000 grams force (or about 10 to 80 Newtons). There are at least two modes of potential failure, including breakage of the sutures or the sutures tearing out of the tendon. The Kessler and modified Kessler repair techniques tend to exhibit failure toward the low end of the range, for example, between about 1,500 to 4,000 grams force (or about 15 to 40 Newtons), which is much weaker than the original tendon and requires the patient to exercise extreme care during the healing process so as not to disrupt the tendon repair.

For instance, normal flexing of the fingers of the hand without any load generates forces of about 40 Newtons (N) on the tendon. Flexing with force to grasp something with the hand typically will place a force of about 60N-100N on the tendon. Finally, strong grasping of an object, such as might be involved in an athletic activity or in lifting of a heavy object can place forces on the tendons of the hand on the order of 140N or more.

The various suturing techniques also are rather complex and, therefore, difficult to reproduce and perfect as a technique, let alone perform it on the small tendons in the hand. Further, because they employ locking stitches, the two tendon ends must be brought to and maintained in the correct position relative to each other (i.e., with the ends in contact) throughout the entire procedure because the locking stitches do not permit future adjustment of the repair (as did some of the earlier techniques that do not use locking stitches).

Another significant difficulty with repairing lacerated and avulsed tendons in the hand, and, particularly, in the fingers is the need to re-route the severed tendon (usually the proximal tendon stump) through the pulley system of the finger joint. Specifically, when a tendon is severed or avulsed, the proximal tendon stump tends to recoil away from the laceration site toward the wrist. Accordingly, it often is necessary to make a longitudinal incision proximal to the laceration site in order to retrieve the proximal portion of the severed tendon and guide it through the pulley system of the finger back to the laceration site for reattachment to the distal tendon stump.

As reported in Evans and Thompson, at least one researcher has employed a Mersilene mesh sleeve having a diameter slightly larger than the tendon that is subsequently sutured to the two apposed tendon ends. Experimental failure loading as high as 10,000 grams force (100N) was reported using the sleeve. However, Mersilene, which is a non-degradable polyester, a common material used for manufacturing sutures used in orthopedics, has the disadvantage that human tissue will experience a local tissue response leading to adhesion of the polyester to tissue surrounding the repair site. This is undesirable in tendons and ligaments since the tendon must be able to glide freely relative to the surrounding tissue, such as the pulleys in the fingers. While a sleeve may be well suited for use with tendons and ligaments which are substantially cylindrical, it is less easily employed with tendons having a flat or ovaloid cross section. Moreover, any added bulk, in this case to the outside of the tendon, could be problematic as this repair would have to traverse the pulley system of the fingers.

U.S. Pat. No. 6,102,947 discloses another method and apparatus for repairing tendons that involves an implant that can be sutured to the tendon and which provides a splint running between the two tendon ends. The implant essentially comprises a wire bearing a first pair of wedges on one side of the midpoint of the wire with their pointed ends facing away from the midpoint and a second pair of wedges on the other side of the midpoint of the wire with their pointed ends also facing away from the midpoint (i.e., facing oppositely to the first pair of wedges). The first pair of wedges is pushed (or pulled) into one of the severed ends of the tendon and the other pair is pushed (or pulled) into the other severed end of the tendon. The wedges are sutured to the tendon and are retained within the tendon. This system provides high tensile strength to the repair.

Further, Ortheon Medical of Winter Park, Fla., USA developed and commercialized an implant for flexor tendon repair called the Teno Fix. The Teno Fix implant is substantially described in Su, B. et al, "A Device for Zone-II Flexor Tendon Repair: Surgical Technique", The Journal of Bone and Joint Surgery, March 2006, Volume 88-A-Supplement 1, Part 1. The assembled implant comprises two intratendonous, stainless-steel anchors (in the form of a coil wrapped around a core) joined by a single multi-filament stainless steel cable. The implant is delivered to the surgeon unassembled, comprising a stainless steel cable with a stop-bead affixed to one end of the cable, two separate anchors with through bores for passing the cable therethrough, and another stop-bead with a through bore for passing the cable therethrough.

In practice, one of the anchors is advanced into a longitudinal intratendonous split (tenotomy) made in the proximal tendon stump so that the anchor sits within the longitudinal tenotomy and engages the tendon substance by capturing tendonous fibers between the core and the anchor. The other anchor is placed in the distal tendon stump in the same manner. Next, a straight needle with the stainless-steel cable attached thereto is threaded into the through-bore of the distal anchor from the small end of the anchor and is pulled through the center of the cut surface of the distal tendon stump until the stop-bead at the end of the cable opposite the needle contacts the distal anchor. The stainless-steel cable with the needle attached is then guided into the cut end of the proximal stump and through the through-bore of the anchor in the proximal stump from the large end of the anchor to the small end. The proximal stump of the tendon is then brought into contact with the distal stump by tensioning the cable, and the second stop-bead is placed over the stainless-steel cable at the proximal end of the proximal anchor. The second stop-bead is then crimped to lock it to the cable and the excess cable is cut so that the cable end is flush with the second stop-bead.

A disadvantage of the Teno Fix is the size of the tendon anchor, which is large and, thus, may add resistance to the tendon as it passes through the pulley system. Another disadvantage of the Teno Fix is the invasive nature of implanting the device wherein the entire track of skin over the tendon path must be incised in order to effect the implantation of the device. A third disadvantage is that the attachment of the anchor to the tendon is rather weak, reporting only about 46 Newtons of pull strength. These disadvantages are overcome by the subject and method described in this invention.

A disadvantage of most, if not all, of the prior art techniques discussed above is a high infection rate.

SUMMARY OF THE INVENTION

The invention comprises methods and apparatus for reattaching the opposed ends of an anatomical member, such as a tendon, ligament, or bone, during preparing and healing of the member using a surgical repair device that can be securely attached to the member and then safely guided through tortuous anatomy for reattachment and repair. The repair device further includes structural means to secure opposed ends of the member against separation during healing. Devices for aiding in the positioning of the surgical repair device also are provided.

DESCRIPTION OF THE DRAWINGS

FIGS. 2A-2L illustrate various stages of a surgical procedure in accordance with a first embodiment of the method in accordance with the invention.

FIGS. 4A-4D illustrate various stages of a surgical procedure in accordance with another embodiment of the method in accordance with the invention.

FIG. 5 shows apparatus for reattaching a member in accordance with another embodiment of the invention.

FIG. 6A illustrates an alternative connector for interconnecting two tendon repair devices in accordance with the principles of the present invention.

FIG. 6B illustrates a procedure for locking the cables of two tendon repair devices in the connector of FIG. 7A.

FIGS. 11B-11F illustrate another alternate technique using the apparatus of FIG. 11A.

FIG. 12A illustrates an alternative apparatus in accordance with the invention.

FIGS. 12B-12C illustrate another alternate technique using the apparatus of FIG. 12A.

FIG. 13A is a perspective view of one embodiment of a unitary dilation catheter in accordance with another embodiment.

FIG. 13B is a perspective view of one embodiment of a multi-piece dilation catheter in accordance with another embodiment.

FIG. 13C is a perspective view of one embodiment of a guide member for the dilation catheters of FIGS. 13A and 3B.

FIGS. 14A-14G illustrate another alternate technique using the apparatus of FIG. 13A or FIG. 13B.

DETAILED DESCRIPTION

In accordance with the present invention, a surgical implant and associated technique is disclosed for repairing tendons, ligaments, and the like following laceration, avulsion from the bone, or the like. The invention is particularly adapted for repairing a lacerated or avulsed flexor tendon, e.g., flexor digitorum profundus from the distal phalanx and/or the flexor digitorum superficialis from the middle phalanx.

First Set of Exemplary Embodiments

Figure 1:
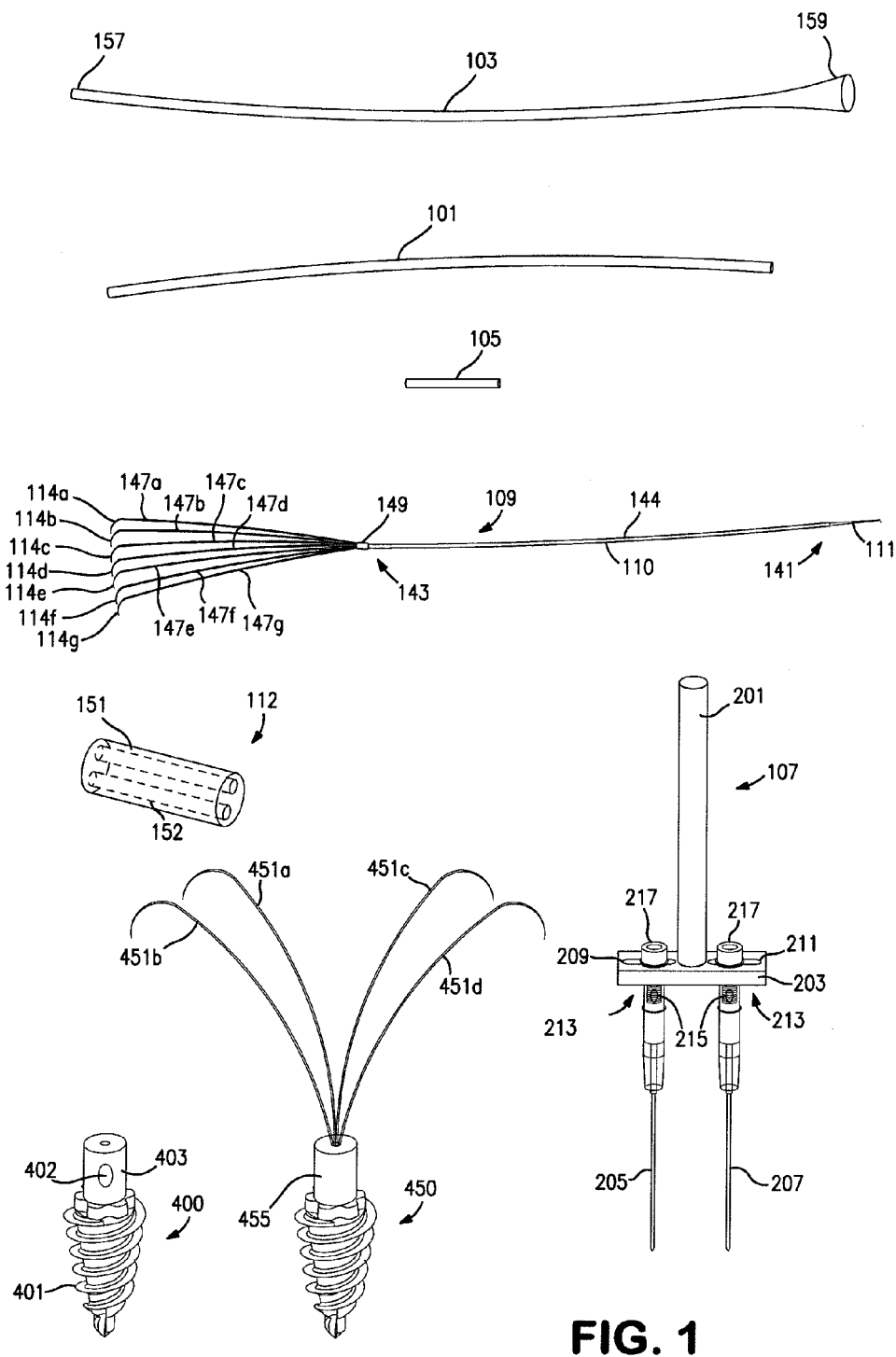
FIG. 1 shows the various components that may be used for repairing a severed member, such as a tendon or ligament, in accordance with a first embodiment of the apparatus of the invention.

FIG. 1 illustrates the components in accordance with a first embodiment of the invention. As will be described in detail below, not all of the components necessarily will be used in each surgical procedure. The components include a pulley catheter 101 which will be used, if needed, to guide the tendon repair device of the present invention along with a severed tendon stump, ligament stump, or similar anatomical feature through one or more anatomical restrictions to the repair site, e.g., through the pulley system of the finger. The components further include a flanged catheter 103, which will be used to guide a severed tendon stump through anatomical restrictions to the repair site, if necessary. A catheter connector 105 may be used to connect the pulley catheter 101 and the flanged catheter 103 together end to end, as will be described in detail below. The catheter connector 105 may be a metal dowel. A tendon holder tool 107 may be used, as necessary, to hold the tendon during the surgical repair procedure.

One or more of the tendon repair devices 109 are the actual devices that will effect the repair by reattaching two tendon stumps. Each tendon anchor 109 comprises a multi-filament stainless-steel cable 110. From one end 141 of the cable to an intermediate point 143 of the cable, the individual filaments of the cable are wound in the normal fashion to form a single cable portion 144. A straight needle 111 is attached to the first end 141 of the cable. From the intermediate point 143 in the direction opposite from end 141, the individual filaments of the cable are unwound so as to form a plurality of (in this particular embodiment, seven) separate sutures 147a-147g. A needle, preferably a curved needle 114a-114g, is attached to the end of each of the seven separate cable portions 147a-147g. A fitting attached at the intermediate point 143 keeps the cable portion 144 from unwinding. The fitting, for instance, may be a sleeve 149. In one preferred embodiment of the invention, the stainless-steel cable is formed of 343 individual strands wound in groups of seven. Thus, from the sleeve 149 to the first end 141, the cable 144 comprises 343 individual strands making up seven intermediate strands, and each of the intermediate strands comprised of seven smaller wound strands of 49 filaments each, and each of those smaller strands comprised of seven individual strands of seven filaments each. In the other direction from the sleeve 149, each of the seven individual strands 147a-147g comprises seven of those smaller strands wound together (wherein each of those smaller strands comprises seven individual strands wound together).

The afore-described embodiment of the tendon repair device 109 is advantageous because it is particularly easy to fabricate from widely available materials. (e.g., 343 strand stainless steel suture cable and a crimp). The materials can be chosen from the implantable family of metals and alloys including the stainless steels, cobalt chrome alloys, titanium and its alloys and nickel-titanium alloy (NiTinol). However, the tendon repair device 109 can be formed of other materials, such as a polymer fiber, and assembled in other manners, such as braiding, welding, or molding. For instance, it may be formed of individual filaments, fibers or yarns welded together.

In the following discussion, in order to more clearly differentiate them, the single ended portion 144 of the tendon repair device 109 will be referred to as cable portion 144, whereas the strands 147a-147g will be referred to as sutures. However, it is to be understood that the use of these terms is not intended to indicate that they are formed of different materials, since, for instance, in the exemplary embodiment described herein, all of the strands are formed of stainless steel wire.

A connector 112 is used to affix two tendon repair devices 109 to each other as will be described in detail below. The connector 112 in this illustrated embodiment comprises a block of material, preferably a deformable metal such as stainless steel, having two side-by-side through bores 151, 152 having inner diameters slightly larger than cable portion 144. As will be described in greater detail below, near the end of the tendon re-attachment procedure, each cable portion 144 will be inserted in opposing directions through each through bore 151 and 152 of the connector 112 and the connector will be deformed (i.e., crimped) to lock the cable portions 144 therein.

Finally, a bone anchor 400 or 450 can be used in procedures where the tendon has avulsed from the bone or has been severed too close to the bone to provide sufficient tendon length to retain a tendon repair device 109. In a first embodiment, the bone anchor 400 has a threaded distal end 401 for screwing securely into bone. The proximal end 403 includes an eyelet 402 through which sutures can be passed. As will be described in more detail hereinbelow, the sutures can be tied in the eyelet. Alternately, the proximal end 403 can be formed of a deformable material, such as a thin-walled metal, so that the eyelet can be crushed by a crimping tool to capture the sutures therein. In a second embodiment, the bone anchor 450 may be manufactured with one or more sutures 451 extending from the proximal end 455, such as four sutures 451a, 451b, 451c, 451d. The ends of the sutures are provided with needles 452a, 452b, 452c, 452d.

The tendon repair devices, surgical tools, and methods will be described herein below in connection with the repair of a lacerated flexor digitorum profundus at the level of the middle phalanx. However, it should be understood that this is exemplary only. Various stages of the procedure are illustrated by FIGS. 2A-2L.

First, if the proximal end of the divided tendon can be reached from the wound site, then it is gently retrieved through the wound to be held by the tendon holder 107.

The tendon holder 107 comprises a handle 201, a cross bar 203 at the distal end of the handle 201, and first and second needles 205 and 207, respectively, extending distally from the cross bar 203. The needles 205 and 207 are slidable laterally within slots 209 and 211, respectively, in the cross bar 203. Particularly, the proximal ends of the needles comprise a stop shoulder 213, and an internally threaded bore running from the stop shoulder 213 to the proximal end of the needle. A screw 217 can be threaded into the proximal end of each needle 205, 207 to trap the cross bar 203 between the head of the screw 217 and the stop shoulder 213 of the needle 205, 207 to affix each needle in any given position along its slot 209, 211.

Depending on the length of tendon extending outside of the wound opening, the surgeon may pierce the tendon with one or both of the needles 205, 207 of the tendon holder 107 to hold the tendon outside of the wound. See FIG. 2C, for example, which illustrates the tendon holder 107 holding a tendon stump 153a. The surgeon preferably pierces the tendon about 1 cm from the severed end.

However, if the tendon is not readily retrievable from the wound and must be accessed through another incision and brought back to the wound site, the tendon holder 107 still may be used, but first the tendon must be retrieved to the wound site. In such a case, the pulley catheter 101 and flanged catheter 103 will be used to retrieve the tendon. Specifically, the pulley catheter 101 is a hollow plastic tube formed of a biocompatible polymer of such composition and/or wall thickness so that it is relatively rigid, but bendable. It might, for instance, have the approximate flexibility of a typical surgical vascular catheter. The relative rigidity of the pulley catheter will permit it to be pushed through narrow anatomical passages, such as the pulleys of the fingers. However, its flexibility will permit some bending to accommodate an overall curved path. Preferably, the pulley catheter is formed of a material having a low friction coefficient to allow the pulley catheter to readily pass through and around bodily tissues such as the tendon pulley system. Suitable biocompatible polymers include homopolymers, copolymers and blends of silicone, polyurethane, polyethylene, polypropylene, polyamide, polyaryl, flouropolymer, or any other biocompatible polymer system that meets the mechanical characteristics above. Various cross sections of the pulley catheter other than a simple tubular structure can also be used, such as a solid structure, multi-lumen, or complex geometry that would provide the mechanical characteristics above. The coefficient of friction of the surfaces of the pulley catheter may be inherent to the materials used to construct the device or may be enhanced through a surface preparation such as a lubricious coating or mechanical modification of the surface such as longitudinal recesses.

The particular length, material, wall thickness, inner diameter, outer diameter, and stiffness of the pulley catheter 101 may vary greatly depending on the particular tendon or ligament with which is it to be used. The length, of course, would be dictated by the longest length that it might be required to traverse. The inner diameter must be large enough to easily accommodate the cable portion 144 of the tendon repair device 109. The outer diameter must be small enough to pass through the anatomy that it may be called upon to pass through. The particular material and cross sectional geometry (e.g., wall thickness) of the pulley catheter will largely dictate the stiffness of the catheter and, as noted above, should be selected to provide enough rigidity to allow it to be pushed through a narrow path, but flexible enough to bend to accommodate bends in the path. In the exemplary case of the flexor digitorum profundus at the level of the middle phalanx, the pulley catheter may be formed of silicone and be 120 millimeters in length with a wall thickness of 0.5 mm, and an outer diameter of 2 mm. A silicone having a durometer of 50-80 (Shore A) may be used for the pulley catheter.

The flanged catheter 103 also is a hollow tube formed of a biocompatible material, preferably a polymer. However, the flanged catheter preferably is softer than the pulley catheter. The flanged catheter has a first end 157 having a diameter that is approximately equal to the diameter of the pulley catheter 103 so that it can be connected end-to-end with the pulley catheter, as described in more detail further below. It also has a flanged end 159 that is tapered so as to essentially form a funnel for accepting the end of a tendon stump, also as will be described in more detail further below. As will become clear in the ensuing discussion, while the flanged catheter will traverse essentially the same path as the pulley catheter, the pulley catheter will guide or pull the flanged catheter into the anatomical path along with the tendon repair device attached to the tendon stump inside the flanged portion 159 of the flanged catheter. Accordingly, the flanged catheter need not be rigid. Actually, the flanged catheter should be relatively flexible because it may need to be bent into a tortuous shape to accommodate passage of the cable portion 144 of the tendon repair device 109. Furthermore, the flange portion 159 of the flanged catheter 103 particularly should be readily collapsible in order to collapse around the tendon stump and pass through narrow anatomical passages, such as the pulleys of the fingers, with the tendon stump and tendon repair device enclosed therein as will be described in more detail below.

The flanged catheter 103 should have a length, wall thickness, inner diameter, outer diameter, and material composition suited to its purpose. Its purpose is to allow the single-ended portion 144 of the tendon repair device 109 to pass through it and to follow the pulley catheter through an anatomical path, as will be described more fully below. Accordingly, the flanged catheter has a narrow end 157 and a wide end 158. The wide end terminates in a cone or flange 159 in order to make it easier to insert the straight needle 111 at the end of cable portion 144 of the tendon repair device 109 into it as well as contain the tendon stump. The narrow end 157 of the flanged catheter 109 is narrow in order to be mated to the end of the pulley catheter.

The flanged catheter 103 also is preferably formed of a material having a low friction coefficient to allow the flanged catheter to readily pass through and around bodily tissues such as the tendon pulley system. Such biocompatible polymers can be chosen from homopolymers, copolymers, and blends of silicone, polyurethane, polyethylene, polypropylene, polyamide, polyaryl, flouropolymer, or any other biocompatible polymer system that meets the mechanical characteristics above. Various cross sections of the flanged catheter other than a simple tubular structure can also be used such as a solid structure, multi-lumen, or complex geometry that would provide the mechanical characteristics above. The coefficient of friction of the surfaces of the flanged catheter may be inherent to the materials used to construct the device or may be enhanced through a surface preparation such as a lubricious coating or mechanical modification of the surface such as longitudinal recesses.

In the exemplary case of the flexor digitorum profundus at the level of the middle phalanx, the flanged catheter may be formed of silicone and be 120 millimeters in length with a wall thickness of 0.5 mm, and an outer diameter of 2 mm. However, it is preferred that the flange portion 159 of the catheter be fabricated of a thinner cross section material, for example, 0.25 mm or less, that will allow the flange portion 159 of the flanged catheter to envaginate the tendon stump and collapse as it tracks through the anatomical pathway for repositioning of the tendon stump, e.g., pulley system of the finger. A softer silicone, for instance, of 20 to 40 durometer (Shore A) is preferred for the flanged catheter.

Figure 7:
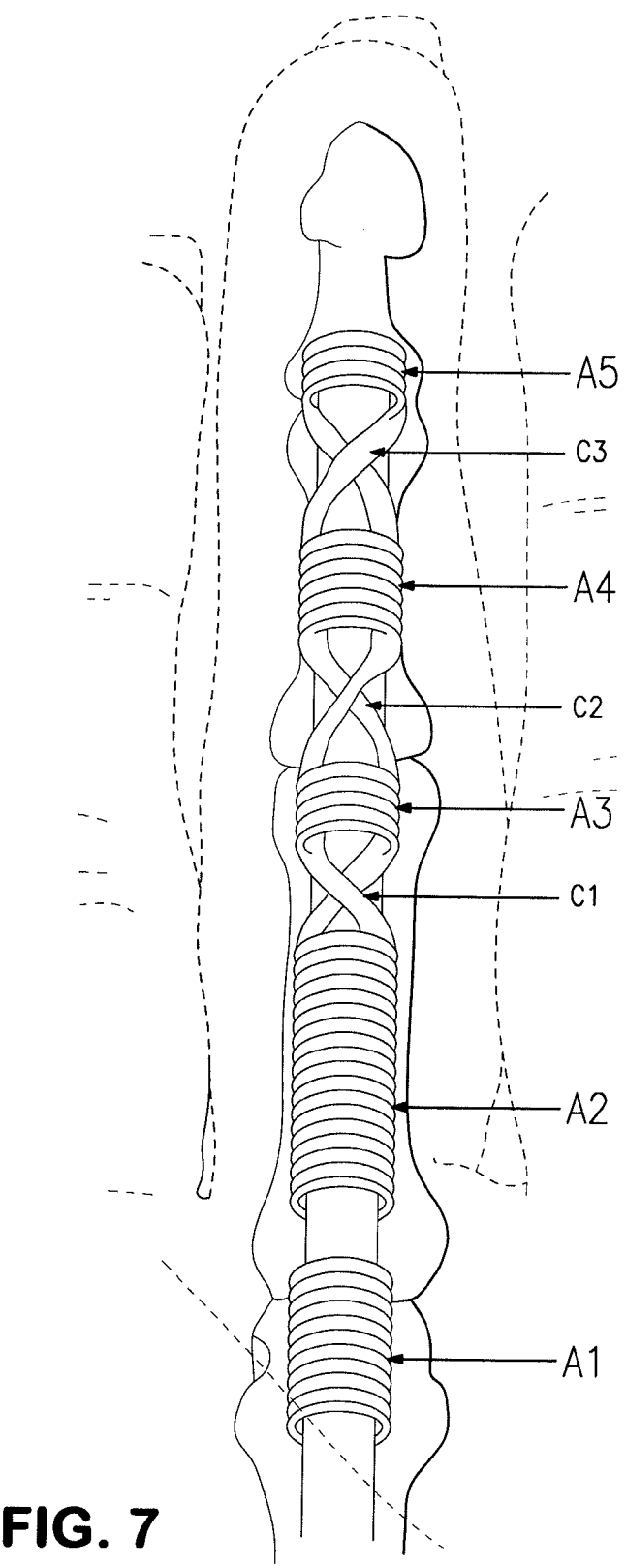
FIG. 7 illustrates the pulley system of the finger.

Referring now to FIG. 2A, in use, if the tendon has retracted and must be retrieved from a first incision 161 into a second incision (or the wound) 160, as is typical of tendon lacerations in the hand, an incision 161 is made, typically in the palm of the hand, where the tendon 153 can be retrieved. If, on the other hand, the proximal tendon stump is distal to the A2 pulley, then the tendon would be exposed through an incision just distal to the A2 pulley. The pulley system of the pinky finger is shown in FIG. 7 disembodied from the surrounding tissue for sake of clarity. It comprises five annular pulleys, termed A1 through A5, and three cruciate pulleys, termed C1, C2, and C3 as shown. The pulley system is not shown in most other Figures in order not to obfuscate the invention.

The pulley catheter 101 is passed into the wound or incision 160 at the laceration site and slowly pushed proximally toward the new incision 161 beneath the A3 pulley through the pulley system of the finger. If resistance is encountered such that the pulley catheter 101 cannot be pushed through proximally, then a ½ cm to 1 cm incision (not shown) may be made midway between the skin creases of the proximal interphalangeal joint of the finger and the crease at the base of the finger. This is at a level between the A2 pulley and the A3 pulley of the finger. The dissection is carried down gently to the flexor sheath where the pulley catheter will be found. The pulley catheter can then be pulled past the obstruction or resistance through this incision. Then the pulley catheter can continue to be advanced proximally through the pulley system of the finger by pushing gently on it until it reaches the tendon retrieval incision 161 and is exposed proximally.

Next, as shown in FIG. 2B, the narrow end 157 of the flanged catheter 103 is connected to the proximal end of the pulley catheter 101. If the components are sufficiently large and/or the surgeon is sufficiently dexterous, the narrow end of the flanged catheter may be inserted directly into the proximal end of the pulley catheter. Otherwise, a metal dowel 105 or other form of catheter connector (e.g., a hook) may be used to make the connection. Particularly, the catheter connector 105 is rigid and the narrow end 157 of the flanged catheter 103 can be inserted over one end of the catheter connector. Then, the other end of the catheter connector 105 can be inserted into a tight friction fit in the proximal end of the pulley catheter 101 to interconnect the pulley catheter 101 and the flanged catheter 103.

Next, with reference to FIG. 2C, the proximal stump 153a of the tendon is delivered through the incision 161 in the palm so that approximately 2 cm of the tendon is exposed outside of the incision 161. (If the proximal tendon stump has retracted only a short distance and is present at the level of the proximal phalanx, then the tendon can be delivered through an incision distal to the A2 pulley or between the A1 and A2 pulleys, as the case may be). Preferably, a flexible barrier 165 is placed under the tendon holder 107 and the proximal tendon stump 153a to create a working 'table' for practicing this technique. With the pulley catheter 101 and the flanged catheter 103 attached, the pulley is pulled distally from incision 160 to draw the flanged catheter 103 into and through the pulley system between incisions 160 and 161. When the leading end 157 of the flanged catheter 103 exits through incision 160 so that the flanged catheter 103 is running between the two incisions 160, 161, the pulley catheter 101 and connector 105 are removed, as shown in FIG. 2C.

Turning now to FIG. 2D, the straight needle 111 at the end of cable portion 144 of the tendon repair device 109 is then placed in the tendon stump 153a approximately 1 cm from the end 168a of the stump 153a and the needle 111 is directed out through cut end 168a of the tendon stump 153a. The needle 111 is pulled through until the sleeve 149 is approximately ½ cm from the cut end 168a. If the tendon exposure is too little, then the sleeve 149 may be positioned somewhat closer to the cut end 168a.

Next, a small tenotomy is made in the tendon so that the crimp can be buried within the tendon. The condition of the tendon and tendon repair device at this point of the procedure is shown in FIG. 2D.

With the tendon repair device 109 in this position, the seven free strands 147a-147g of the tendon repair device are used to stitch the tendon repair device 109 to the tendon stump 153a. More particularly, two of the sutures, e.g., 147a and 147g, are pushed through the tendon using the curved needles 114a and 114g and tied to each other in a knot 185. In a preferred embodiment, the two sutures are stitched to the tendon 153a using a locking cross stitch or cruciate pattern. In this instance, the loading will be spread amongst multiple points of fixation along the length of the repair. Also, due to the cruciate method, under tension, the repaired tendon would tend to reduce in diameter which would facilitate traversing through the pulley system. The sutures 147a, 147g are cut at the far side of the knot to remove excess material beyond the knot. In order not to obfuscate the invention, however, the stitches are shown in most of the drawings, including FIGS. 2E-2J, representatively as Xs. Only in drawings that are of suitable scale, such as FIG. 2L, or in which some significant discussion of the stitches is given in the corresponding text is the stitching represented more accurately.

Figure 2E:
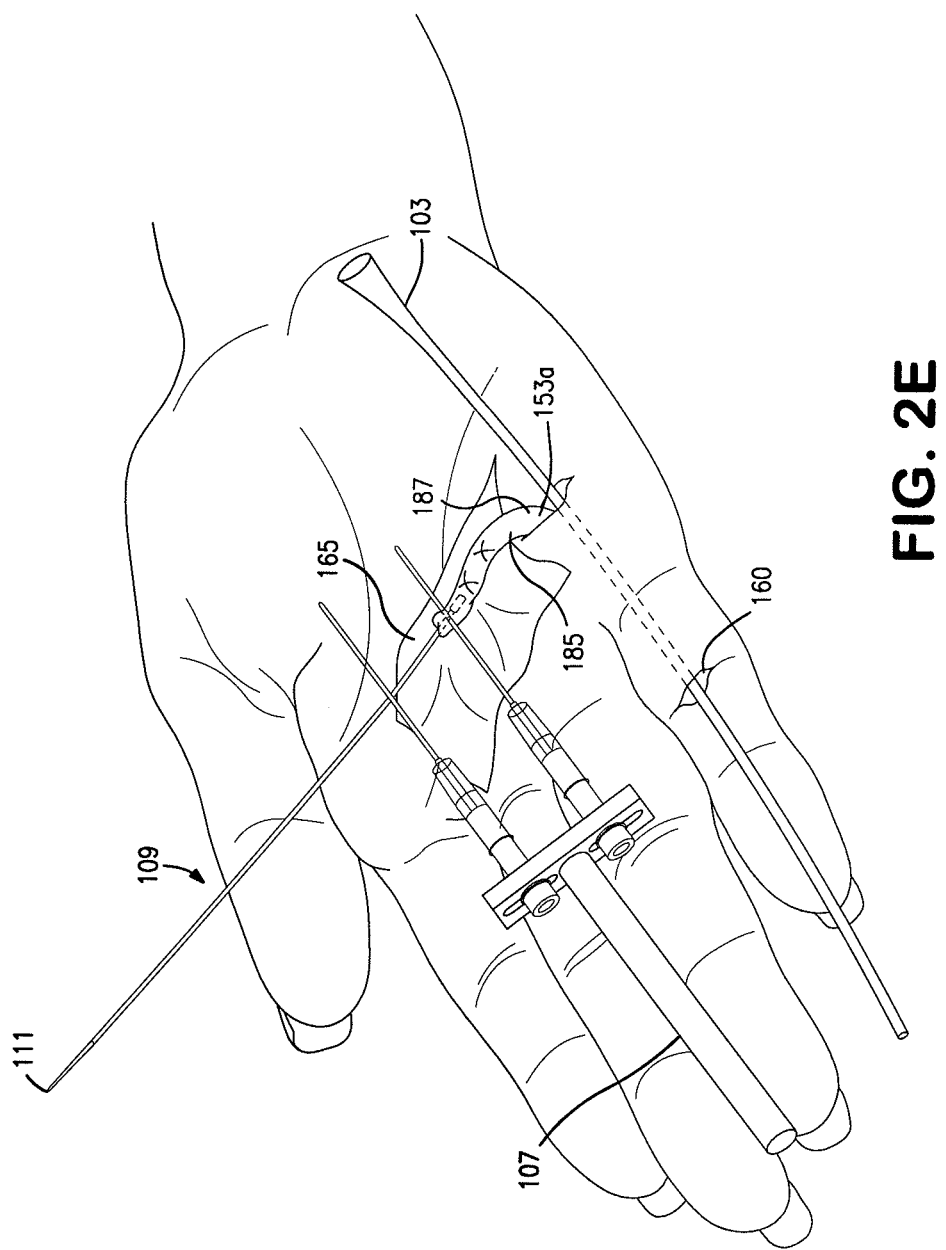

Next, two more sutures, e.g., 147b and 147f, are stitched to the tendon using the curved needles and 114b and 114f and tied together in another knot 187. Preferably, the knot 187 is a crisscross locking stitch with the two limbs traveling proximally. The sutures are cut after the knot is tied. In a preferred embodiment of the invention, as shown in FIG. 2E, the first knot 185 and the second knot 187 are tied at different levels along the length of the tendon stump 153a. Finally, two more sutures, e.g., 147c and 147e, are tied in a similar crisscross knot (not seen) on the other side of the tendon stump 153a and cut.

Finally, the single remaining suture 147d may be cut off or may be used to couple with any of the other free ends (prior to trimming) to form yet another knot. It is preferable that there be multiple points of fixation of the tendon repair device to the tendon stump.

In one embodiment of the invention, the sutures can be of different lengths, organized in pairs, such that each of the two sutures forming a pair are the same length and each pair of sutures is of a different length. When stitching the sutures to the tendon, each pair of sutures of the same length are stitched to the tendon and knotted to each other. This embodiment is advantageous in that it provides an easy visual indication to the surgeon which pairs of sutures are to be tied to each other during the procedure (the sutures of the same length) thus simplifying the procedure.

Figure 2F:
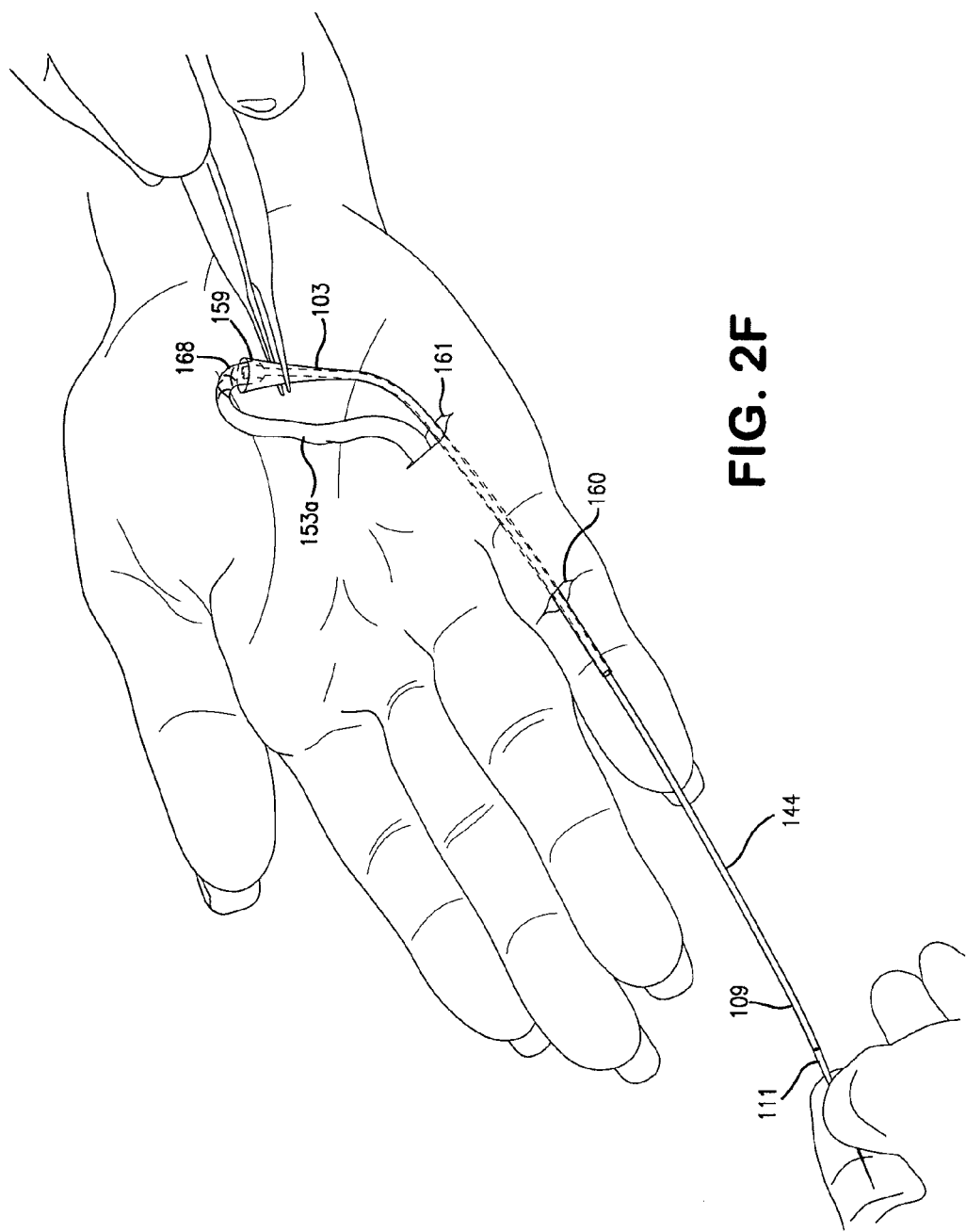

Referring to FIG. 2F, now that the tendon repair device 109 is securely fixed to the proximal tendon stump 153a, the tendon is removed from the tendon holder and the straight needle 111 at the end of cable portion 144 is inserted into the flange 159 of the flanged catheter 103. Tendon repair device 109 is advanced through the flanged catheter until the end of the tendon stump 153a (which is stitched to the back end of the tendon repair device 109) is in the flange portion 159 of the flanged catheter 103. Cable portion 144 preferably is rigid enough that the cable can be pushed along with the flanged catheter through the pulley system of the finger and follow the flanged catheter 103 out of the wound 160. Now the surgeon can grasp the needle 111 through the flanged catheter 103 with a clamp and pull the needle 111, cable portion 144, flanged catheter 103 and tendon stump 153a (contained inside collapsible flange 159 of flanged catheter 103), through the pulley system of the finger and out of the wound 160. Alternately, if the needle 111 protrudes from the distal end 157 of the flanged catheter, the surgeon can grasp the needle 111 or cable portion 144 directly by hand or with a clamp and pull the needle 111, cable portion 144, flanged catheter 103, and tendon stump 153a (contained inside collapsible flange 159 of flanged catheter 103), through the pulley system of the finger and out of the wound 160. If any resistance is encountered, then the path through the pulley system can be inspected through a separate incision.

The flange 159 of the flanged catheter 103 will collapse around the tendon stump as needed to pass through the pulley system of the fingers.

Figure 2G:
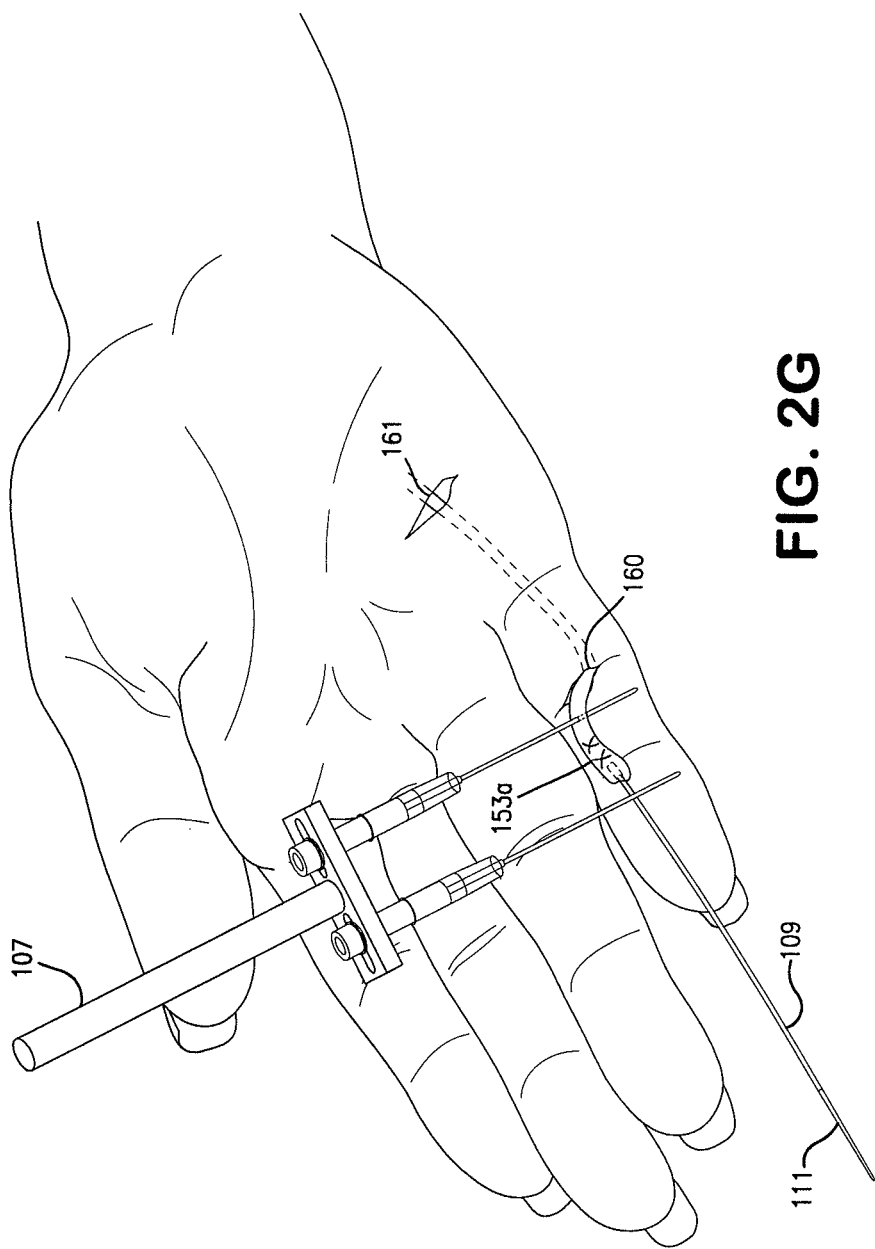
Figure 21:
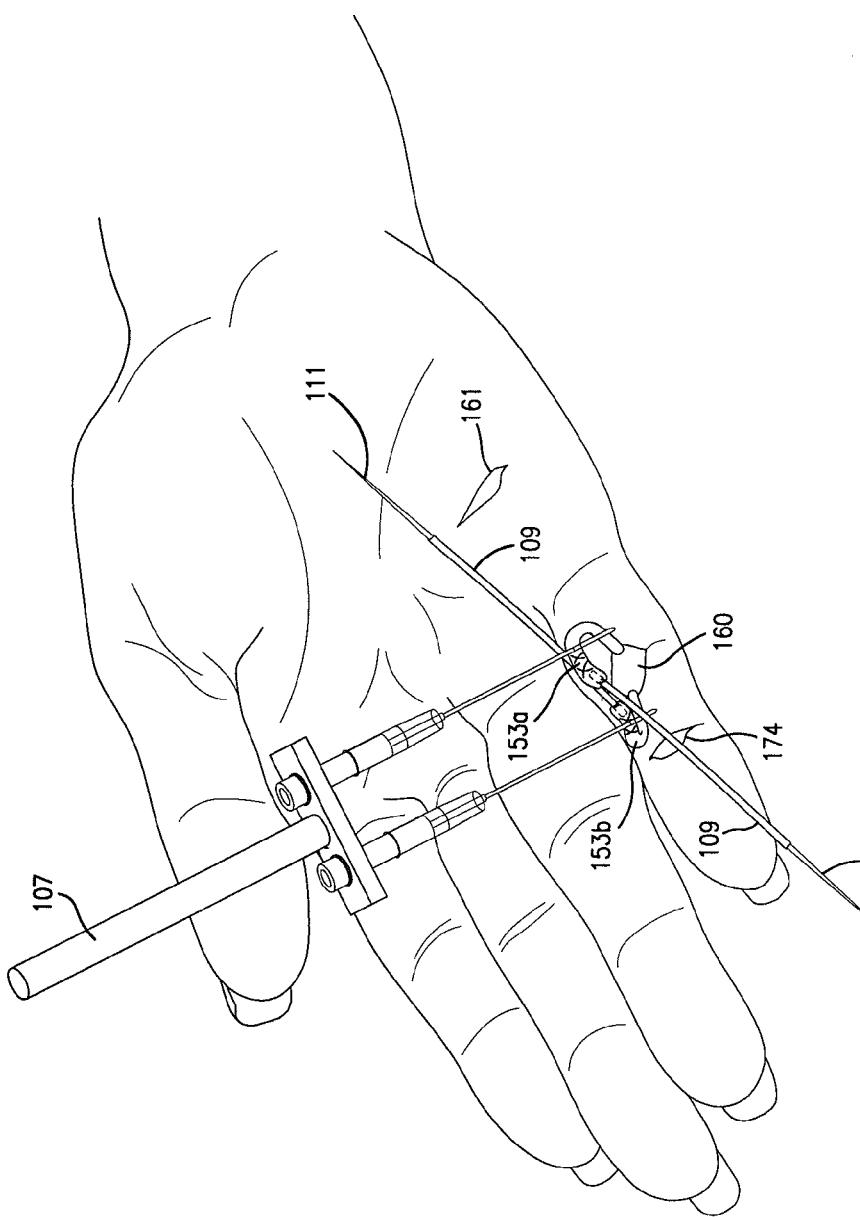

Referring to FIG. 2G, once the tendon stump 153a has reached the wound 160, flanged catheter 103 can be removed from the tendon repair device 109 and tendon stump 153a, thereby exposing the tendon repair device 109 and tendon stump 153a through the wound 160. Needle 205 of tendon holder 107 can be placed across the proximal tendon stump 153a to hold the tendon stump 153a in a stable position.

In FIG. 2G and subsequent drawings, the length of the tendon stump(s) may be exaggerated to help with the illustration of the repair. However, it should be understood that, once the tendon has been retrieved to or near the original wound site (as in FIG. 2G), there is little or no excess tendon to expose outside of the skin, especially if the finger is in an open (i.e., unflexed) condition. In actuality, if the finger is unflexed, the surgeon will probably be working on the tendon primarily within the skin. However, in some of the drawing figures, the length(s) of the tendon stump(s) may be exaggerated in order not to obscure the illustration of the methods and apparatus being described in connection therewith. Furthermore, in some of the drawings in which the stitches are not substantially related to the features being discussed in connection therewith, the stitches and/or knots are represented by a simple criss-cross pattern in order not to overly complicate the drawings. In other drawings in which the stitching or knots are more closely related to the features being the discussed, a more accurate representation of an appropriate knot/stitch is presented.

It also should be noted that other features, such as the diameters or lengths of the sutures, crimps, crimp connectors, and needles, are not necessarily drawn to scale in all of the figures.

Next, referring to FIG. 2H, a very similar procedure is performed with respect to the distal tendon stump. Particularly, the distal tendon stump 153b is delivered into the wound 160 in a similar fashion as described above in connection with the proximal tendon stump 153a. That is, if adequate exposure is not possible to retrieve the distal tendon stump 153b directly from the wound 160, a 1 cm incision 174 may be made just distal to the crease at the distal interphalangeal joint and dissection carried down onto the distal extent of the A5 pulley so that the distal tendon stump 153b can be exposed through this new incision. The pullet catheter 101 is guided between the incisions 160, and 174 and the flanged catheter 103 is inserted into the distal end of the pulley catheter 101. The pulley catheter 101 is then pulled through the pulley system with the flanged catheter 103 following it until the flanged catheter 103 is positioned through the pulley system and extending at opposite ends from incision 160 and 174, as shown in FIG. 2H. Next, another tendon repair device 109 is attached to the distal tendon stump 153b in the same manner as described above in connection with the proximal tendon stump. FIG. 2H illustrates the procedure at this stage.

Referring next to FIG. 2I, the distal tendon stump is next guided to the original wound site 160 using pulley catheter 101 and the flanged catheter 103 as described above in connection with the proximate tendon stump 153a. The second needle 207 of the tendon holder 107 may be placed through the distal tendon stump 153b, exposing approximately 1 cm of tendon as described above in connection with the proximal tendon stump. This stage of the procedure is illustrated in FIG. 2I.

Figure 2J:
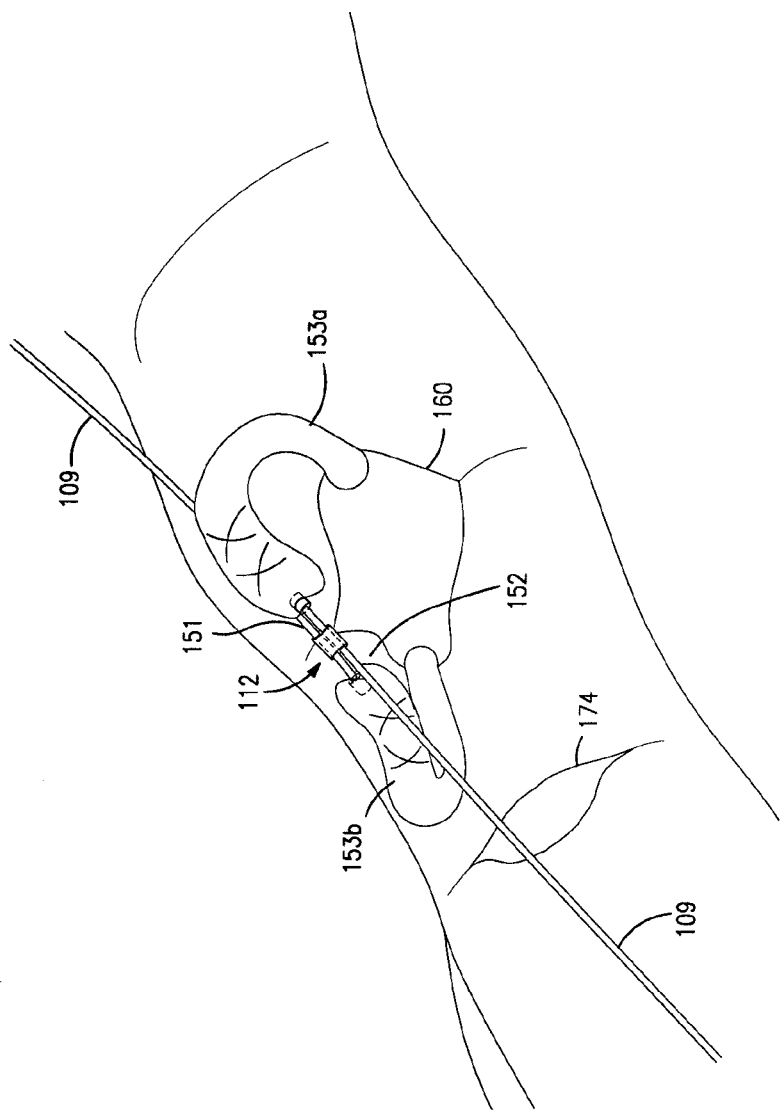

Next, referring to FIG. 2J, the connector 112 is brought to the site and the straight needles 111 at the ends of the cable portions 144 are inserted through the bores 151, 152 in the connector 112. More particularly, the straight needle 111 of the tendon repair device 109 that is attached to the proximal tendon stump 153a is passed through one of the bores 151 traveling in the proximal-to-distal direction and the straight needle 111 of the tendon repair device 109 that is attached to the distal tendon stump 153b is passed through the other through bore 152 in the connector traveling in the opposite direction, i.e., from the distal-to-proximal direction.

Figure 2K:
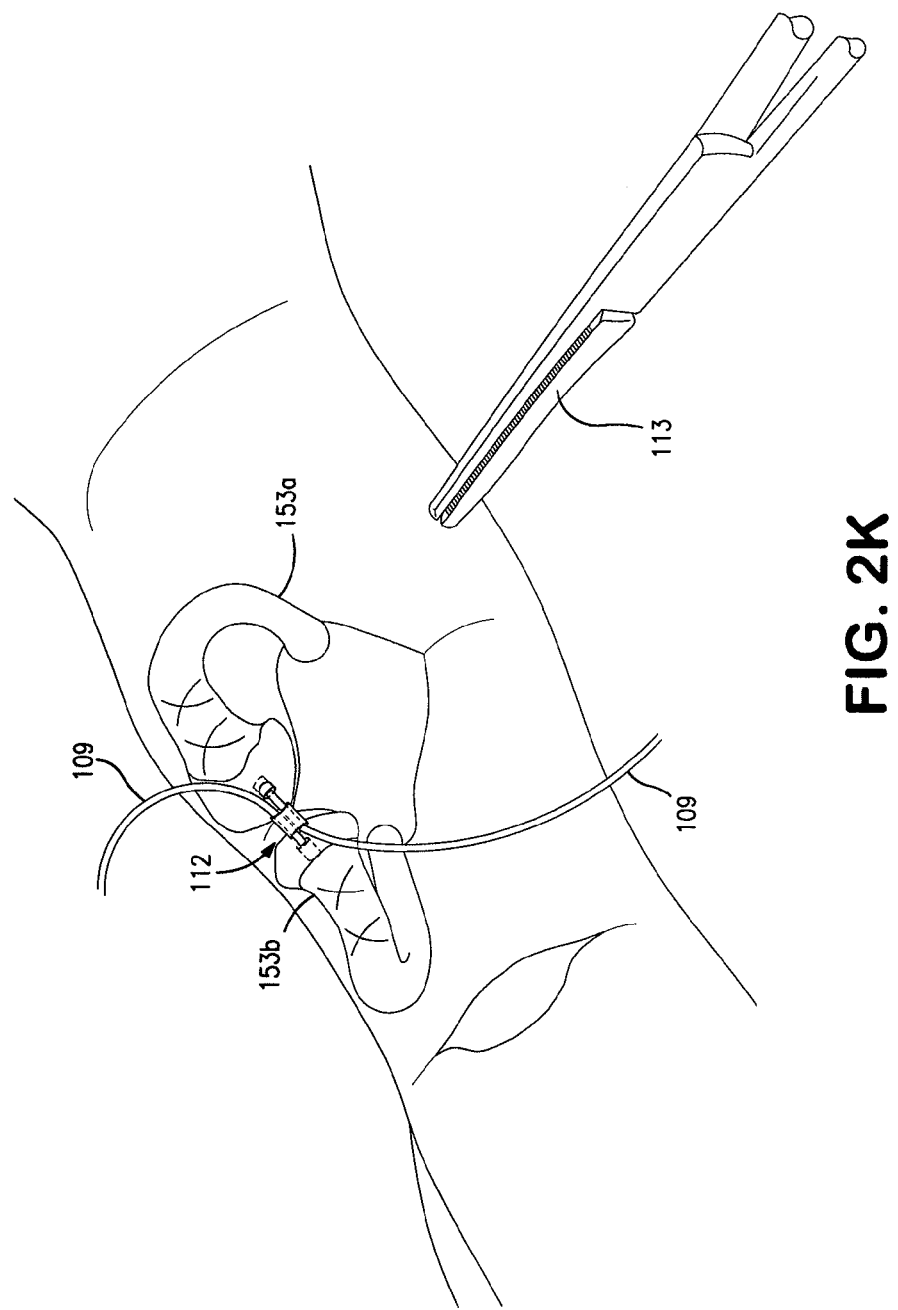

Referring now to FIG. 2K, the proximal and distal tendon stumps 153a, 153b are removed from their respective tendon holder needles (and the tendon holder is put aside) and traction is applied to pull the distal tendon stump 153b proximally and pull the proximal tendon stump 153a distally until there is overlap of the two tendon stumps of approximately 1 mm, with the connector 112 essentially buried in tendon between the tendon ends 168a, 168b.

A crimping tool 113 is then used to crimp the connector 112, thereby securely affixing the cable portions 144 of the two tendon repair devices inside of the connector 112. More particularly, with reference to FIG. 2K, the tendon stumps 153a, 153b can be folded back slightly to expose the connector 112 so that the crimping tool 113 can be placed over the crimp connector without contacting or damaging the tendon.

Alternatively, if necessary, the tendon holder 107 can be used to help bring or hold the tendon stumps together by adjusting the positions of the two needles 205, 207 in the slots 209, 211 of the tendon holder 107 towards the center so that they are very close to each other and piercing each tendon stump with one of the needles.

The extra lengths of cable portions 144 extending from the connector 112 are then cut as close to the edge of the crimp connector as possible and discarded. The connector 112 will then retract into the substance of the tendon when it is released and the tendon ends are unfolded and there will be excellent cooptation of the tendon ends, as illustrated in FIG. 2L. FIG. 2L represents four cruciate stitches 185, 187, 185', and 187' made using the tendon repair devices. While cruciate stitches are believed to be particularly efficacious, other types of stitches can be used as well. If desired, one or more 6-0 nylon epitendonous stitches 183 can be placed around the tendon ends to assure good cooptation of the tendon ends in order to 'tidy up' the edges of the repair.

Figure 3:
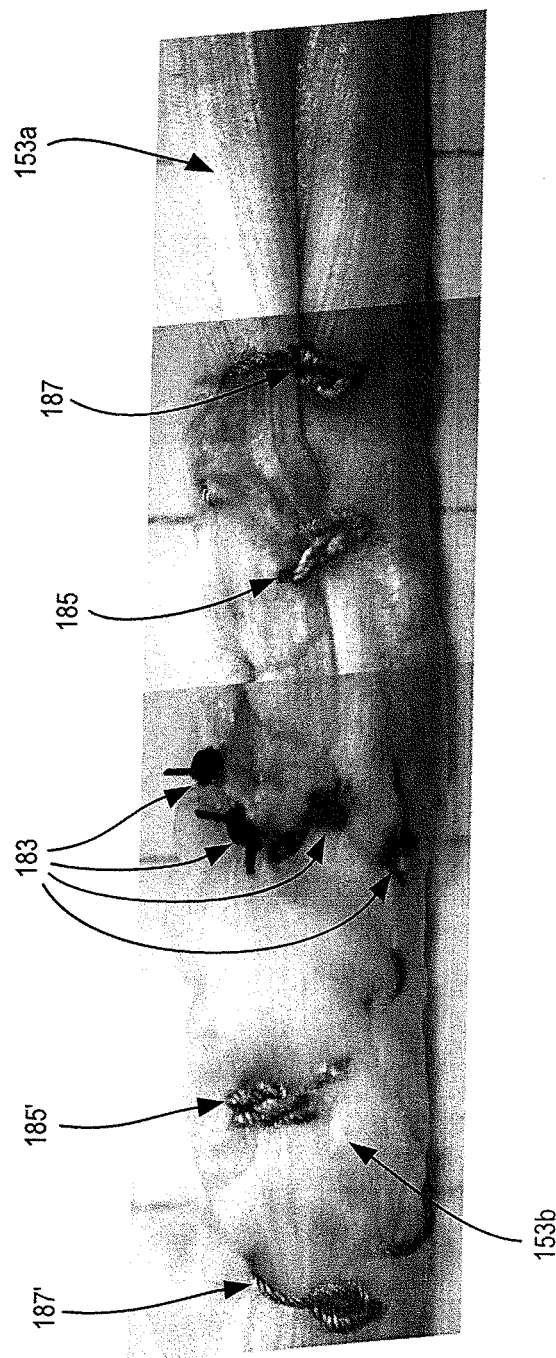
FIG. 3 is a photograph of a completed tendon repair in accordance with the first embodiment.

FIG. 3 is a photograph of an actual tendon repair performed in accordance with the first embodiment of the invention. The first and second knots 185 and 187, respectively, can be seen in the proximal tendon stump 153a. Similar knots 185' and 187' are seen in the distal tendon stump 153b. Four epitendonous stitches 183 also can be seen.

The one or more skin wounds can be stitched closed as usual and the procedure is ended.

While the procedure and apparatus has been described above in connection with one particular procedure relating to the repair of a flexor tendon laceration, flexor digitorum profundus at the level of the middle phalanx, this is merely an exemplary application. The invention can be applied to reattach other types of tendons, ligaments, or other similar load-bearing soft tissues.

Second Set of Exemplary Embodiments

FIGS. 4A-4D illustrate another apparatus and procedure in accordance with the principles of the present invention that can be used in situations where the tendon (or ligament) has avulsed or otherwise been separated from the bone, rather than severed. The apparatus and procedure described in connection with FIGS. 4A-4D also may be used in situations where the tendon or ligament has been severed very close to the bone so that there is not enough tendon length left to effectively attach a tendon repair device 109 to that stump.

In these types of situations, a tendon repair device such as the afore-described tendon repair device 109 is still used in the manner described above in connection with FIGS. 2A-2H in connection with the stump that has sufficient length, e.g., at least 2 cm, (typically the proximal stump). However, with respect to the bone or short tendon stump, one or more cables are attached directly to a bone anchor 400 instead of using a second tendon repair device.

The bone anchor may be any bone anchor that can be attached to bone at its distal end and to which a suture or cable can be attached to the proximal end thereof. Suitable bone anchors are disclosed, for instance, in PCT International Published Patent Application WO 2008/054814, which is incorporated herein by reference. However, much simpler bone anchors can be used also.

In a simple embodiment of a suitable bone anchor, such as illustrated in FIG. 1, the bone anchor may comprise a threaded distal portion 401 for threading into bone and an eyelet 402 for receiving the cable of the tendon repair device integrally formed in the proximal portion of the bone anchor main body. In other embodiments, the bone anchor may be prefabricated with one or more sutures integrally formed therein and extending from the proximal end thereof.

A surgical procedure in accordance with this embodiment will now be described in connection with an exemplary injury in which the flexor digitorum profundus has been lacerated very close to the distal phalanx. However, it should be understood that variations of this procedure can generally be used in connection with any tendon or ligament that has avulsed from the bone or been severed close to the bone.

Figure 10A:
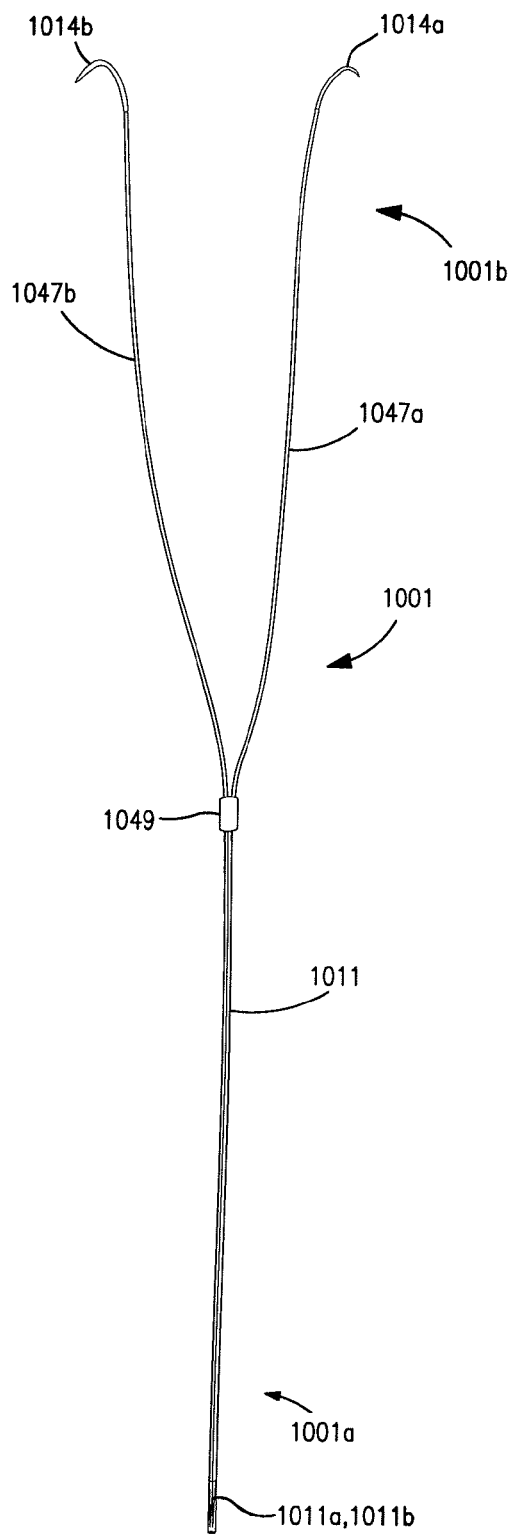
FIG. 10A illustrates another alternate embodiment of a tendon repair device in accordance with the principles of the present invention.

FIGS. 4A-4D illustrate various stages of an exemplary procedure for effecting a four strand repair (i.e., the repair will have four suture strands running between the two tendon stumps). This embodiment utilizes a different tendon repair device 1001 than the tendon repair device 109 illustrated in FIGS. 1-2L. This tendon anchor is illustrated in FIG. 10A, which is discussed in more detail below in connection with another exemplary surgical procedure. With reference to FIG. 10A, it comprises two strands or filaments 1047a, 1047b, with each strand having a needle at each end. In the illustrated embodiment, curved needles 1014a and 1014b are provided at the first ends of the strands 1047a, 1047b, respectively, and straight needles 1011a, 1011b are provided at the second end of the strands 1047a, 1047b, respectively. The two strands comprising the tendon repair 1001 device are joined intermediate their ends, such as by a fixed or slidable crimp 1049. The crimp 1049 may initially be uncrimped so that it can slide along the device and, if desired, crimped at a suitable stage of the procedure. As shown in FIG. 10A, the tendon repair device 1001 may be delivered to the surgeon with a portion of the sutures and the straight needles 1011a, 1011b on end 1001a enclosed in a sheath 1011 to ease the process of passing that end of the tendon repair device 1001 into the pulley catheter 101 and/or flanged catheter 103.

The long tendon stump 501 is operated upon essentially as described above in connection with the first embodiment. Particularly, with reference to FIG. 4A, the tendon stump 501 is retrieved, if necessary, by making a retrieval incision 531 where needed, exposing the tendon stump 501, and stitching end 1001b of the tendon repair device 1001 to the tendon stump using the curved needles. In this exemplary case, where there are only two sutures 1047a, 1047b, one cruciate stitch is preferred. In embodiments using tendon repair devices having more sutures, such as the tendon repair device 109 of FIGS. 1-2L having seven sutures, then the tendon repair device can be stitched to the tendon stump using multiple cruciate or other stitches, exactly as described above in connection with the embodiment of FIGS. 1-2L, for instance. Next, the pulley catheter 101, flanged catheter 103, and catheter connector 105 (if needed) can be used as previously described to guide the tendon repair device 1001 and tendon stump 501 back to the injury site 533. The narrow sheath 1011, if provided, will facilitate threading of the end 1001a of the tendon repair device 1001 into and through the catheters.

Figure 4A:
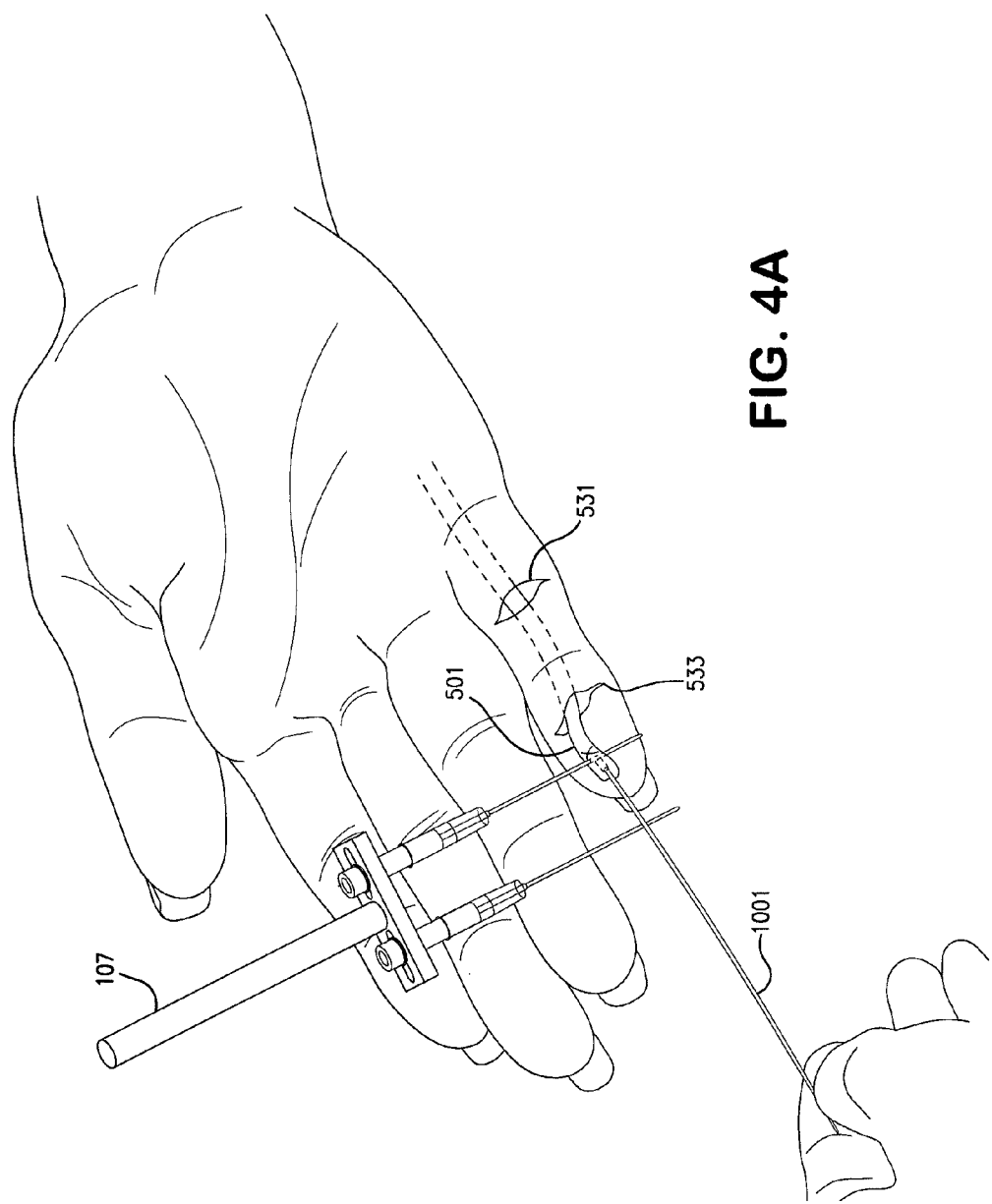

Then, the tendon stump 501 is placed in a tendon holder 107 while the distal tendon stump is prepared. FIG. 4A shows the condition of the surgical site after these steps have been performed, i.e., with the tendon 501 in a tendon holder 107 with a tendon repair device 1001 stitched thereto.

Figure 4B:
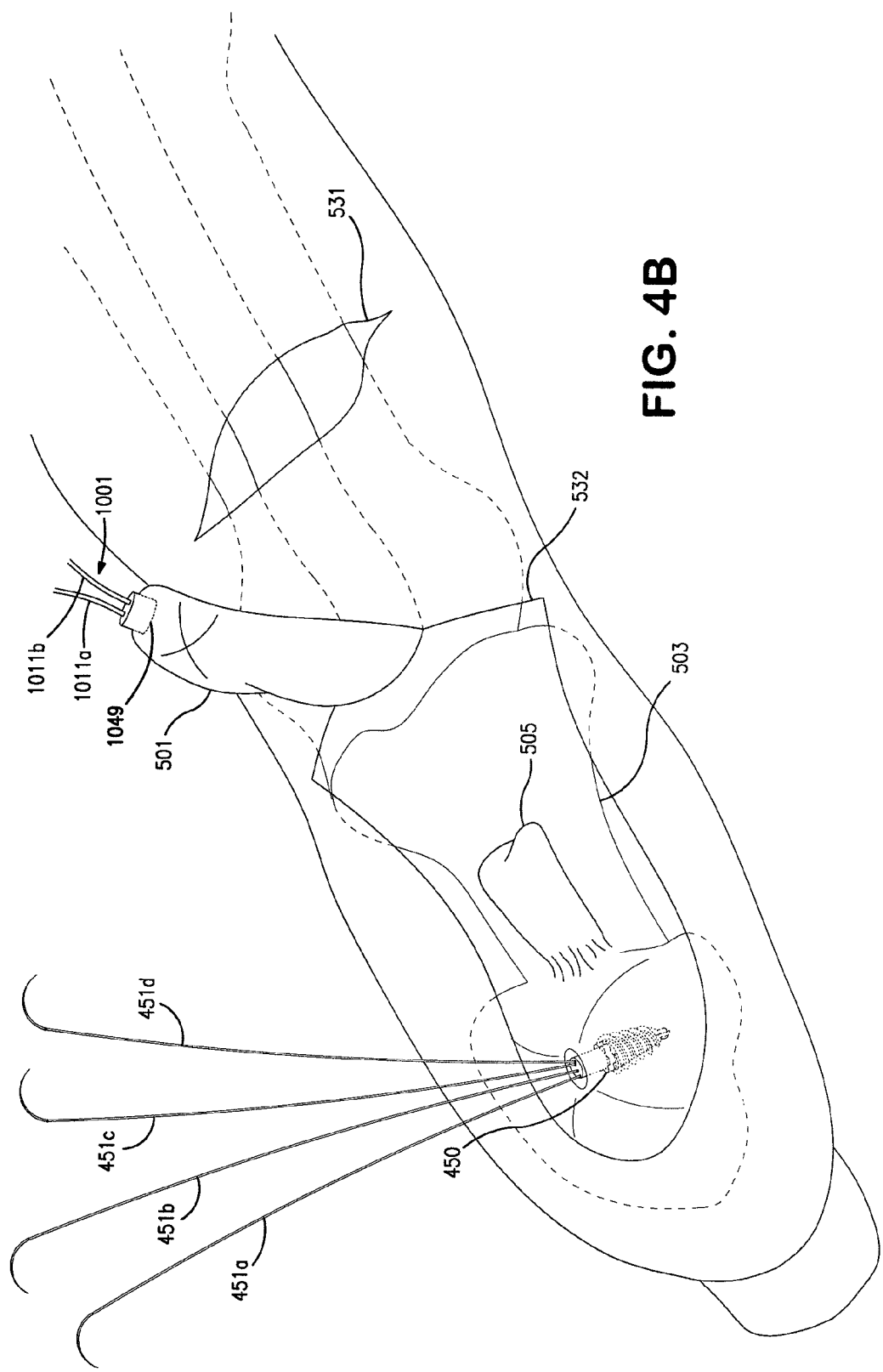

Next, referring to FIG. 4B, with respect to the bone 503 (and distal stump 505, if any is present), an incision 532 (which may include original injury 532) is made and dissection is carried down to expose the bone 503 of the distal phalanx. A bone anchor, such as bone anchor 450 shown in FIG. 1, is then affixed to this bone 503 by screwing it in securely.

Next, with reference to FIG. 4C, since this exemplary embodiment is a four strand repair, two of the sutures 451c, 451d of the bone anchor 450 can be cut off at or as close to the bone anchor as possible. The other two sutures 451a, 451b are threaded through the distal stump 505. Now, referring to FIG. 4D, the tendon stumps are brought together with a slight amount of overlap and the two sutures 451a, 451b of the bone anchor 450 are stitched and knotted to the proximal stump 501. Likewise, the tendon repair device 1001 that is already stitched to the proximal tendon stump 501 at one end thereof is then stitched to the distal stump 505 at the other end. FIG. 4D shows the completed repair in accordance with this embodiment.

Of course, the number of strands on the bone anchor 450 and the number of strands on the tendon repair device 1001 can be increased to provide a stronger repair, such as a six eight, ten, or even twelve strand repair, if desired.

A tendon injury of the type illustrated in FIGS. 4A-4D, in which there is only a short distal tendon stump remaining (or none at all) also can be repaired using a tendon repair device 109 such as illustrated in FIGS. 2A-2L and the other bone anchor 400 shown in FIG. 1, the long tendon stump 501 is operated upon exactly as described above in connection with the first embodiment of FIGS. 2A-2L. Particularly, the proximal tendon stump 501 is retrieved, if necessary, by making a retrieval incision where needed, exposing the tendon stump 501, attaching a tendon repair device 109 to the tendon stump, and using the pulley catheter 101, flanged catheter 103, and catheter connector 105 (if needed) as previously described to guide the tendon stump back to the injury site.

Next, an incision is made and the bone anchor 400 is affixed to the bone essentially as described above in connection with FIGS. 4A-4D, expect that it is bone anchor 400, rather than bone anchor 450.

Next, if a distal stump of the flexor is still present, such as stump 505 in FIGS. 4A-4D, then the needle 111 and cable 144 of tendon repair device 109 is run through this stump 505 and into and through the eyelet 402 of the bone anchor 400. Particularly, the straight needle 111 at the end of cable portion 144 is brought into the short distal tendon stump 505 through the severed end of the tendon stump 505 and out through the side of the tendon stump near where the stump 505 is still attached to the bone 503 and then through the eyelet 402 in the bone anchor 400.

Next, traction is applied to the cable 144 to draw the proximal tendon stump 501 distally until there is a 1 mm overlap of the proximal tendon stump 501 with the distal tendon stump 505.

Then, the cable 144 is fixed to the eyelet of the bone anchor 503. This can be done by tying the suture or cable to the eyelet 402 of the bone anchor. In a more preferred embodiment, however, the proximal end of the bone anchor 503 is crimped to crush the eyelet 402 of the bone anchor 400, thereby trapping the cable 144 therein.

Finally, the procedure is completed essentially as described above in connection with the embodiment of FIGS. 2A-2L or 4A-4D.

If, on the other hand, there is no or virtually no distal tendon stump remaining to attach to, the proximal stump would instead be attached directly to the bone using the bone anchor. Preferably, the cable portion 144 of the tendon repair device attached to the tendon stump is directly attached to the bone anchor without the use of a second suture or cable 509 and the proximal tendon stump is pulled distally so that the stump envelopes the bone anchor and contacts the bone around the bone anchor. As is often the case, the surgeon may roughen, counter bore or tunnel the bone in the area around the bone anchor for the tendon to attach to.

In another alternate embodiment, only the bone anchor 450 with multiple strands (with needles at the ends of the strands) already extending from the bone anchor is used. No separate tendon repair device 109 or 1001 is used. Rather, the sutures extending from the bone anchor 450 are stitched directly to the proximal tendon stump. This type of embodiment is most suited to an injury in which (1) the proximal tendon stump has not retracted significantly and is, therefore, present at the incision near the distal stump without the need to be retrieved through another incision and (2) there is no distal tendon stump to include in the repair. Particularly, with respect to the first point, if the proximal tendon stump needs to be retrieved, then it would likely be more practical to use the technique described in connection with FIGS. 4A-4D. More specifically, if the proximal tendon stump must be retrieved, then a separate tendon repair device probably will have to be attached to the proximal tendon stump for purposes of retrieving the stump, in any event. In such a situation, it would be simpler to attach the tendon repair device that is already stitched to the proximal tendon stump to the bone anchor than to add another set of sutures.

With respect to the second point, if there is a distal tendon stump, it would be preferable to include sutures emanating from the distal stump that exert a force pulling the distal tendon stump toward the proximal tendon stump. In the absence of a proximal tendon repair device, no sutures exerting such a force would be present and, therefore, the distal tendon stump could conceivably slide away from the end to end contact of the two tendon stumps prior to healing of the tendon stumps.

In repairs in accordance with the bone anchor embodiment, the load on the distal end is borne completely by the bone and bone anchor.

Preliminary testing has shown failure strengths of tendon reattachments performed in accordance with the principles of the present invention of approximately 70-100 Newtons. Accordingly, a tendon and ligament repair in accordance with the principles of the present invention results in a much stronger repair that the current standard of care.

In addition, the procedure is greatly simplified as compared to the present standard of care.

Third Set of Exemplary Embodiments

FIG. 5 illustrates another embodiment in accordance with the principles of the present invention. FIG. 5 is a close up of the proximal tendon stump 153a in accordance with this embodiment of the invention at a stage after the tendon repair device 109 has been stitched to the tendon stump. It is essentially similar to the stage shown in FIG. 2E, but illustrating a different way to finish off the stitches other than tying them in knots in pairs.

This embodiment involves a simpler procedure than in the aforedescribed embodiment in so far as the surgeon will not be required to tie any knots. Rather, as shown in FIG. 5, rather than tying knots in the sutures 147a-147g after stitching them to the tendon, a crimp 603 can be advanced over each suture against the stitch as far as it will go and then crimped with a crimping tool to lock the crimp to the suture, thus locking the stitch to the tendon. Depending on the particular configuration of the curved needles 114a-114g and the crimps 603, the crimps may be slipped over and around the needles onto the sutures 147a-147g. If this is not possible, then the needles 114a-114g can be cut off of the sutures 147a-147g after the corresponding stitch is tied to permit the crimp to be placed on the suture. In this embodiment, the surgeon is not required to tie any knots with the sutures, thus simplifying the procedure. The surgeon is free to use the sutures to create any stitches desired, but they do not need to be knotted at the end.

Fourth Set of Exemplary Embodiments

FIGS. 6A and 6B illustrate an alternative to the crimp connector 115 for attaching two tendon repair devices 109 (or a tendon repair device 109 and a bone anchor 115) to each other. In this embodiment, the connector 701 comprises a connector main body 711 having two parallel, longitudinal through bores 713, 715. The main body 711 may be cylindrical, rectangular, or any other reasonable shape. Another bore 717 is provided in the main body 711 transverse to the direction of longitudinal through bores 713, 715, this bore intersecting the two longitudinal through bores 713, 715. A pin in the form of a block 719 fits in the transverse bore 717. Accordingly, when the block is inserted in the transverse bore 717 as shown in FIG. 6b, it also transversely passes through portions of the longitudinal through bores 713, 715. The dimensions of the block 719, the transverse bore 717 as shown in FIG. 6B, the longitudinal through bores 713, 715, and cable portions 144 (that will pass through the longitudinal through bores 713, 715) are chosen so that the block 719, when inserted into the transverse bore 717 will compress the cables in the longitudinal bores 713, 715 between the side wall of the block 719 and the side walls of the longitudinal bores 713, 715, thereby trapping the cables in the connector 701.

Thus, in this embodiment, rather than crushing the crimp connector with a crimping tool, a pliers or clamp type tool acts on the block 719 and the connector 701 and pushes the block 719 into the connector 701 against the resistance of the cable portions 144 in the longitudinal through bores 713, 715, thereby capturing the cables as described above.

Some of the advantages of this embodiment of the connector include a much lower force requirement for locking since the block 719 does not have to be plastically deformed. Rather, this mechanism relies on the wedging of cables 144 against the inner wall of connector 701 to effect the lock.

There are many possible alternative stitching techniques to the few described above. The present invention can accommodate and permit the surgeon to use any stitching technique desired. In alternate embodiments, the tendon repair device may have only four sutures or, if it has more than four sutures, the surgeon may decide to cut off those sutures that he or she does not use. For instance, two of the sutures of the tendon repair device 109 of FIGS. 1-2L, e.g. sutures 147a and 147g, may be stitched to the tendon using cross stitches and are knotted together as previously described in connection with the embodiment of FIGS. 2A-2L, except that the remaining distal portions of the sutures 147a, 148g extending from the knots are not cut off at this time. Next, another two sutures, e.g., 147b, 147f, are stitched to the tendons at a different level than the first two sutures and knotted, also as described in connection with the embodiment of FIGS. 2A-2L. Then, sutures 147a and 147b are tied in a knot and sutures 147g and 147f are tied in another knot. Now, the distal ends of each of sutures 147a, 147g, 147b, and 147f may be cut off. The other 3 sutures 147c, 147d, 147e, may be cut off and not used or may be used to form other knots. The inter-dependence of the two pairs of sutures in this technique provides greater assurance that the sutures will not tear out of the tendon.

In yet other embodiments, the third pair of sutures also may be tied together with the first two pairs of sutures. The various permutations of stitching techniques and tying together of the sutures are virtually endless.

Sixth Set of Exemplary Embodiments

Figure 8A:
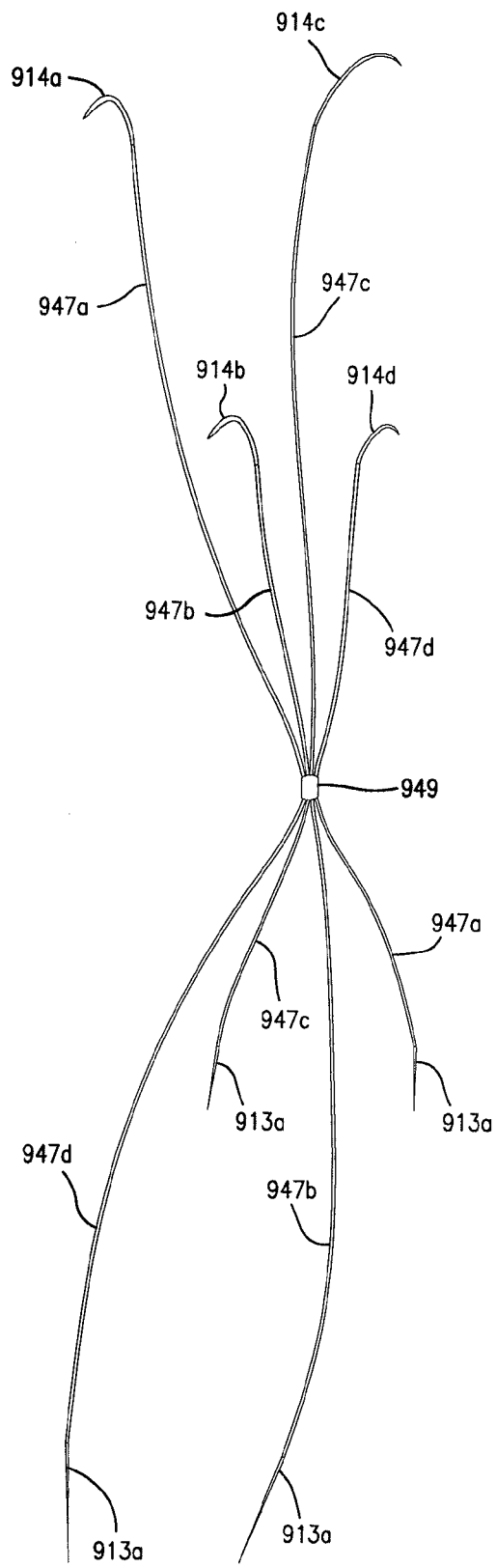
FIG. 8A illustrates an alternate embodiment of a tendon repair device in accordance with the principles of the present invention.

FIGS. 8A illustrates an alternative embodiment of the tendon repair device. This embodiment is particularly suited to, but not limited to, surgical procedures in which either one or none of the tendon stumps needs to be retrieved from a separate incision and be guided back to the wound site. This embodiment also has the advantage of being capable of effecting a repair using only a single tendon repair device, if desired.

As can be seen in this embodiment, rather than having one side of the anchor comprised of multiple sutures and the other side comprised of one cable as was the case for the embodiments illustrated in FIGS. 1-2L and 4A-4E, this tendon repair device has multiple sutures on both sides 901a, 901b of the tendon repair device 901. More particularly, this tendon repair device may be formed of four sutures 947a-947d attached together at one or more intermediate points along their lengths. In one embodiment that is particularly convenient to manufacture, the tendon repair device 901 comprises four sutures 947a-947d with at least one crimp 949 intermediate their lengths holding them together. The crimp may be initially uncrimped so that it can slide along the lengths of the sutures during the procedure. It may be crimped to lock its position relative to the sutures at any point during the procedure. In some procedures, it may not be crimped at all.

Figure 8B:
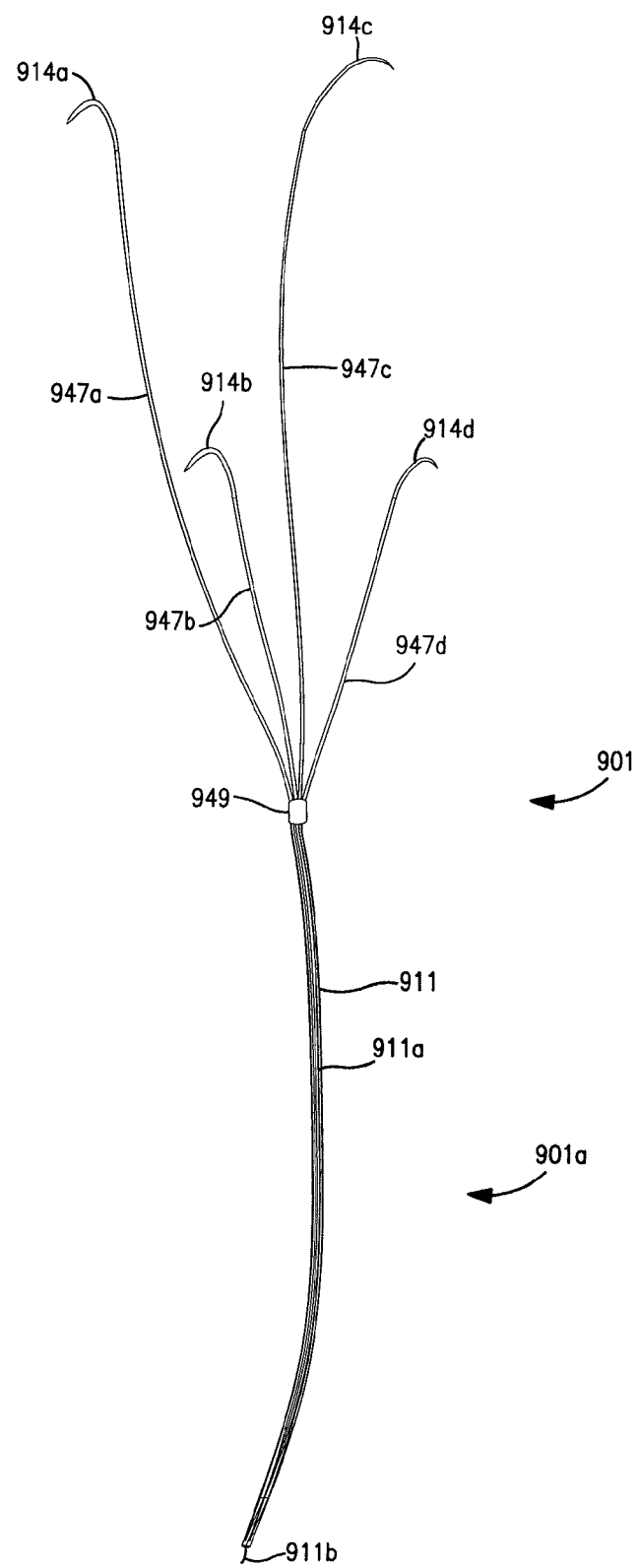
FIG. 8B illustrates the tendon repair device of FIG. 9A as it is preferably delivered to the surgical site.

In this embodiment, the tendon repair device 901 preferably is delivered to the surgical site in the condition illustrated in FIG. 8B, i.e., with at least one of the side 901a contained in a narrow sheath 911 (e.g., a plastic tube) that can be easily passed through the flanged catheter. However, depending on the diameters of the needles, sutures, flanged catheter, the number of sutures in the device, and the material of the flanged catheter, a sheath may be unnecessary or may cover only part of the end 901a (such as just the tips of the needles 913a-913d). In this embodiment, the needles 913a-913d attached to the ends of the sutures on side 901a of the crimp 949 that will be placed in the sheath 911 should be straight needles in order to more readily fit into the sheath 911 and/or through the catheters 101, 103.The needles attached to the other ends of the sutures 947a-947d may be curved needles 914a-914d to facilitate stitching. However, they also may be straight needles.

The first half of the surgical procedure is essentially identical to the procedure described above in connection with the first embodiment illustrated in FIGS. 2A through 2L. More particularly, the procedure is essentially identical to that embodiment up to the stage illustrated in FIG. 2F, the only difference being that, instead of a single cable 144 extending from the far side of the intermediate crimp 949, there are four individual sutures (or cables) contained in a sheath 911.

After the device has been stitched to one tendon stump, the sheath 911, containing the four straight needles and sutures is traversed through the pulley system to the site of the wound as described previously. Next, the protective sheath 911 is removed; thereby releasing the four sutures 947a-947d and straight needles 913a-914d.

In one embodiment, the sheath 911 is cut with a knife or scissor. In another embodiment, the sheath can be torn by hand. In yet another embodiment, and, particularly, the illustrated embodiment, the sheath 911 comprises an integral longitudinal strip 911 a, such as a string embedded within the material of the sheath, having a "tail" 911b extending beyond at least one end of the sheath so that it can be grasped by the surgeon and pulled to tear the sheath, thus freeing the needles for attachment to the tendon stump. Alternately, the strip may comprise a weakened radial segment of the sheath running the full longitudinal length of the sheath. The weakened segment may comprise a strip of the sheath that is integrally formed with the rest of the sheath, but having a thinner wall thickness than the rest of the sheath.

The crimp 949 may be crimped at this stage of the procedure to lock its position on the device 901. For instance, it may be crimped immediately adjacent the end of the tendon stump 902a to which it has been stitched at this point.

When using this embodiment, the other tendon stump 902b preferably is exposed at the wound site without the need to be retrieved. If, however, it must be retrieved through a different incision, it can be retrieved using any reasonable technique, including conventional techniques for tendon retrieval or using the pulley catheter and flanged catheter of the present specification as described above. For instance, a small suture can be stitched to the tendon temporarily and the suture can be advanced through the pulley system of the finger using the pulley catheter 101 and flanged catheter 103 much as described above in connection with the first embodiment.

In any event, with the other tendon stump 902b exposed at the wound, the two stumps 902a, 902b are positioned with their ends opposed to each other and the second end 901a of the tendon repair device can be stitched to the distal tendon stump 902b much in the same way as described above in connection with the first embodiment. Care should be taken to assure that the two tendon ends 902a, 902b appose each other, since it will be difficult, if not impossible, to adjust the relative positions of the ends of the tendon stumps after the first stitch is completed and locked. The tendon holder 107 can be used as previously described to hold the tendon ends apposed to each other. The sutures may be stitched to the tendon in pairs as previously described. The repair can be completed with an epitendonous stitch between the two stumps as previously noted.

This embodiment is advantageous in that it requires no crimp connector or crimping tool and has fewer parts. For example, only one tendon repair device is involved in the procedure, that tendon repair device being double headed, as shown in FIG. 8A.

Seventh Set of Exemplary Embodiments

Figure 9A:
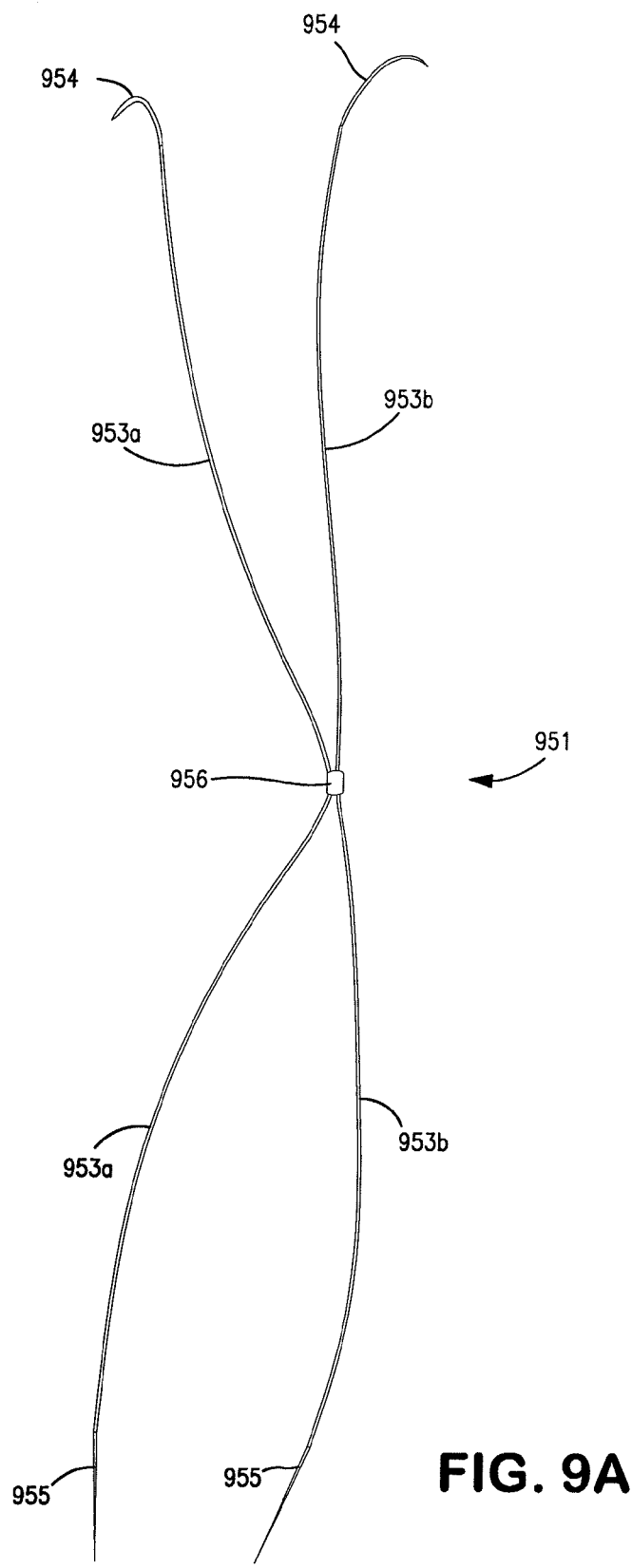
FIGS. 9A through 9D illustrate another embodiment of a tendon repair device and technique in accordance with the principles of the preset invention.
Figure 9B:
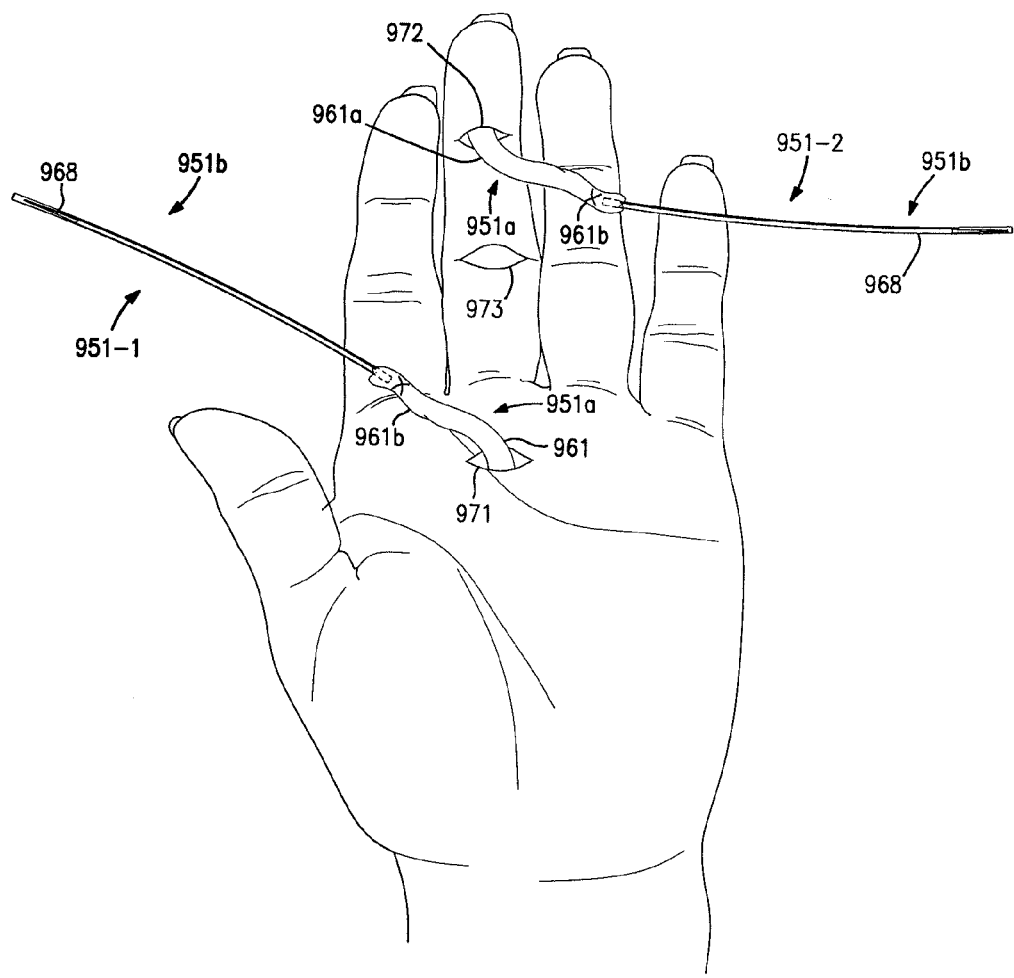
Figure 9C:
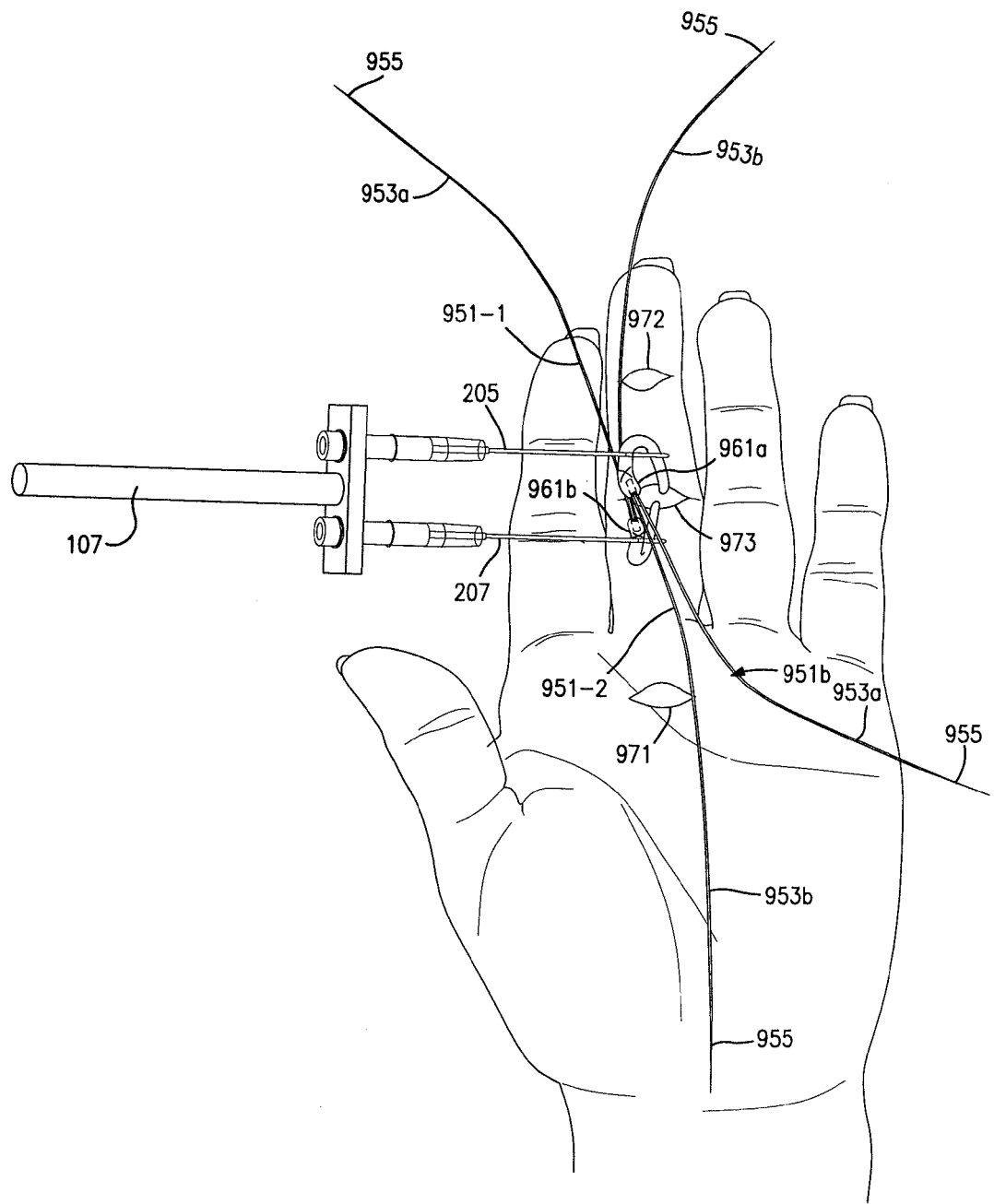

FIGS. 9A-9C help illustrate yet another embodiment of a tendon repair device and technique particularly suited, but not limited, to repairs where both tendon stumps must be retrieved to the repair site by being tracked through anatomy between two incisions. FIG. 9A shows the tendon repair device 951 in accordance with this embodiment. In this embodiment, two tendon repair devices 951 are used, each comprising two strands or filaments 953a, 953b, with each strand having a needle at each end. In the illustrated embodiment, curved needles 954 are provided at the first end and straight needles 955 are provided at the second end of each strand. The two strands comprising a single tendon repair device are joined intermediate their ends, such as by a slidable crimp 956 as previously described in connection with other embodiments. The crimp 956 may initially be uncrimped so that it can slide along the device and, if desired, crimped at a suitable stage of the procedure.

As shown in FIG. 9B, one end 951a of each tendon repair device 951-1, 951-2 is stitched to a respective tendon stump 961a, 961b using the two strands of that end. The other end 951b of each tendon repair device may be initially encased within a sheath 968 similarly to the embodiment of FIGS. 8A and 8B for purposes of being passed through anatomy, such as the pulleys of the finger, using the pulley catheter and flanged catheter described above in connection with other embodiments. However, as noted above in connection with the embodiments of FIGS. 8A and 8B, the sheath may not be necessary.

Next, the tendon repair devices and tendon stumps to which they are stitched can be tracked through anatomy to the repair incision using the pulley and flanged catheters as previously described. The condition of the tendon repair procedure at this point is illustrated in FIG. 9B. Referring now to FIG. 9C, the two tendon stumps 961a, 961b are brought together. If desired, they can be held in position using the tendon holder 107, with one needle 205,207 in each of the tendon stumps 961a, 961b (not shown).

Figure 9D:
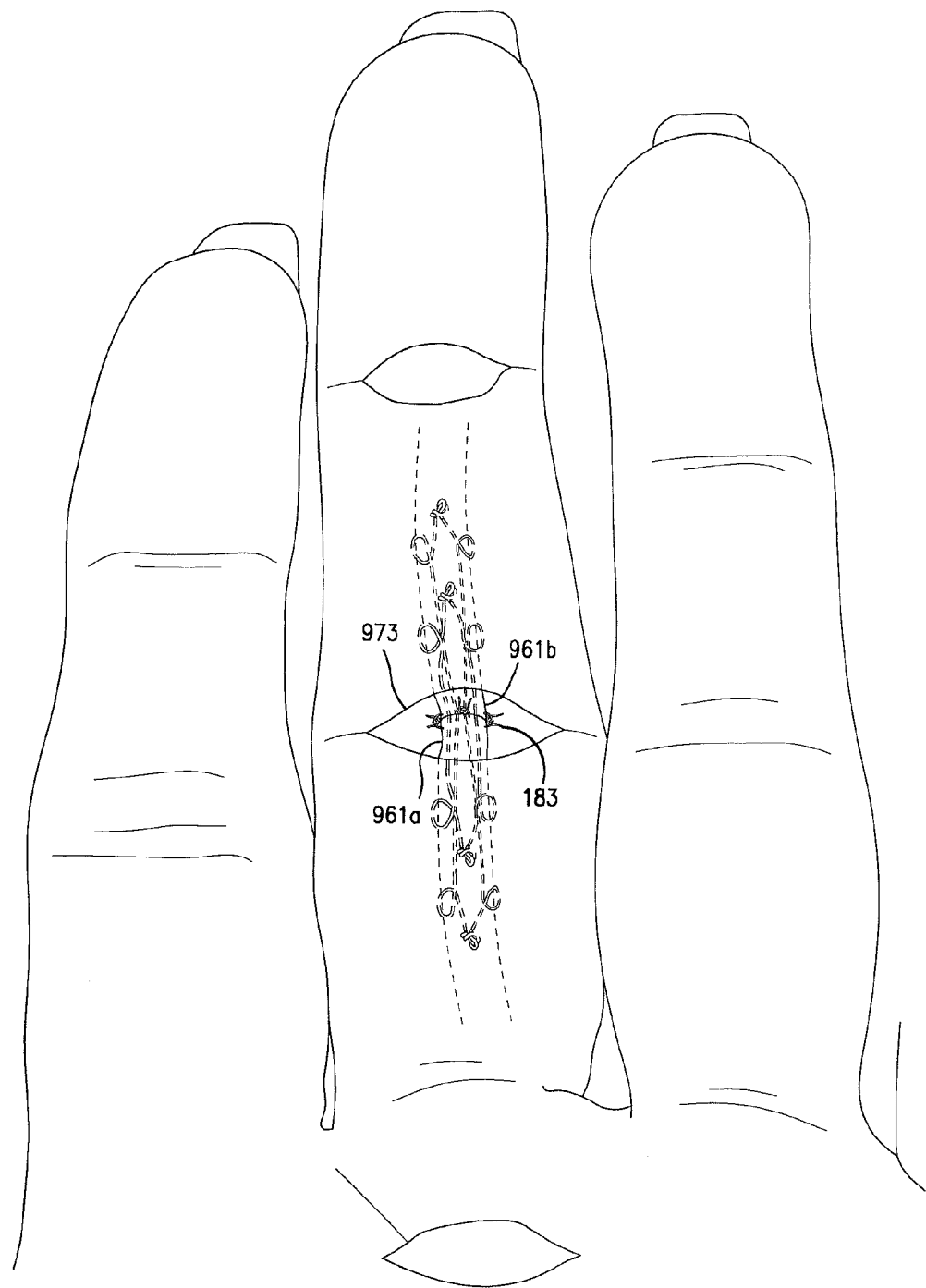

Next, the free ends 951b of the two strands of the first tendon repair device 951-1 (the other ends 951a of which are already stitched to the first tendon stump 961a) are stitched to the second tendon stump 961b, preferably at a different level than the stitches of the second tendon repair device 951-2. Likewise, the free ends 951b of the two strands of the second tendon repair device 951-2 (the other ends 951a of which are already stitched to the second tendon stump 961b) are stitched to the first tendon stump 961b. The completed repair is shown in FIG. 9D. The repair can be completed with an epitendonous stitch as previously described, if desired.

Like the embodiment of FIGS. 8A-8B, this embodiment provides four strands running between the two tendon stumps, and two stitches at different levels in each tendon stump, thereby providing a very sturdy repair.

Eighth Set of Exemplary Embodiments

FIG. 10A illustrates a tendon repair device in accordance with yet another embodiment of the invention. This device 1001 is essentially the same device of FIG. 9A, but with one side in a sheath, as will be described in more detail below. In these embodiments, two tendon repair devices will be used, as in the first embodiment as illustrated in FIGS. 1 and 2A-2L. However, both of these tendon repair devices 1001 have multiple strands at each end, as in the embodiments illustrated in FIGS. 8A-8B and 9A-9D. More particularly, each tendon repair device 1001 comprises two sutures 1047a, 1047b. The two sutures may be coupled together intermediate their ends, such as by a crimp 1049 or sliding sleeve. Alternately, the two sutures may be independent of each other.

Even further, the tendon repair device 1001 may comprise a single cable or suture over much of its length and be broken out into two sutures only near the opposite ends of the anchor. Again, such a tendon repair device may be formed of two sutures twisted together over much of their length and separated near the opposite ends with a crimp, such as crimp 956, at each end of the twisted portion holding the twisted portion together. As in the embodiment of the tendon repair device illustrated in FIGS. 8A-8B and 9A-9D, straight needles 1013a, 1013b preferably are employed on at least one end 1001a of the device 1001 and curved needles 1014a, 1014b are employed on the other end 1001b. As shown, the tendon repair device may be delivered to the surgeon with the sutures and straight needles 1011a, 1011b on end 1001a enclosed in a sheath 1011. The procedures and apparatus for repairing a tendon using this embodiment of the tendon repair device are rather similar to those described previously in connection with the first and second embodiments. Particularly, one or both of the tendon stumps can be retrieved through the pulley system of the finger, as needed, exactly as described in connection with the first embodiment of the invention illustrated in FIGS. 1 and 2A-2L, except that only two sutures are stitched to each tendon stump at one side 1001b of the tendon repair device 1001.

In this embodiment two of the tendon repair devices 1001-1 and 1001-2 are used. One side 1001a of each tendon repair device 1001-1 and 1001-2 is stitched to one of the tendon stumps.

Figure 10B:
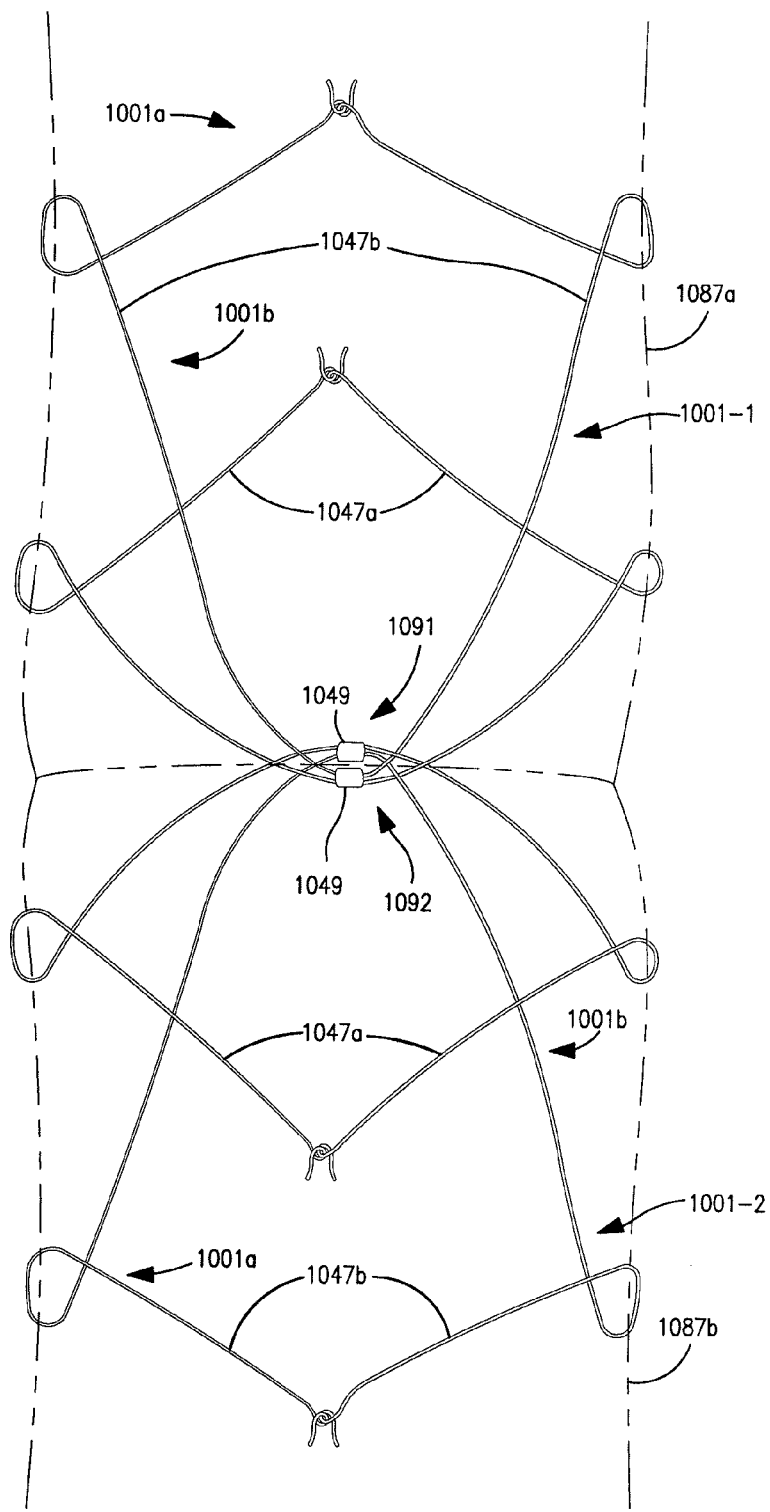
FIG. 10B illustrates two of the devices of FIG. 10A used to repair a tendon.

FIG. 10B helps illustrate how two of these fixation devices 1001 could be used to effect a repair by looping them around each other in accordance with this embodiment of the invention. Generally, one tendon repair device 1001-1 would be folded to form a loop 1091 and stitched to the first tendon stump 1087a and the other tendon repair device 1001-2 would be folded to form another loop 1092 and embedded in the other tendon stump 1087b with the loops joined in the middle as described in detail below.

Specifically, the two sutures 1047a, 1047b and curved needles 1014a, 1014b on one side 1001b of first tendon repair device 1001-1 would be stitched to the first tendon stump 1087a with the other side 1001a of the device sticking out of the end of the respective tendon stump, basically as described in connection with previous embodiments.

Next, with reference to FIG. 10B, the other side 1001a of the first tendon repair device 1001-1 is returned back into the tendon same stump through the end of the stump so that the tendon repair device 1001-1 forms a loop 1091 sticking out of the end of the tendon stump 1087a. This may be performed by individually threading each of the two sutures and straight needles 1014a, 1014b back through the end of the tendon stump 1087a and pulling them out through the side of the tendon stump. The suture(s) should be pulled through so that the loop 1091 protrudes from the end of the tendon stump 1087a by 1 millimeter or less. Preferably, the sutures are pulled through so that the loop 1091 does not protrude at all, but is essentially in the substance of the tendon stump 1087a. Then, the two sutures 1047a, 1047b are stitched to the tendon essentially as described above in connection with the previously described embodiments. At this point, both ends 1001a, 1001b of the tendon repair device 1001-1 are stitched to the tendon stump 1087a and a loop 1091 is located at the severed end of the tendon stump 1087a.

Next, the second tendon repair device 1001-2 is attached to the second tendon stump 1087b in essentially the same manner as the first tendon repair device 1001-1 was attached to the first tendon stump 1001a, except that, after the first two needles 1013a, 1013b at the first end of the 1001a anchor 1001-2 are stitched to the tendon, the other two needles 1014a, 1014b and sutures 1047a, 1047b are guided through the loop 1091 formed by the first tendon repair device 1001-1 to form a second loop 1092 before being stitched to the second tendon stump 1087b. If the loop 1091 of the first tendon repair device 1001-1 is within the substance of the first tendon stump 1087, the substance of the first tendon stump may need to be retracted with a suitable retractor tool to expose the loop momentarily for the second tendon repair device needles and sutures to be passed through the loop. Alternately, the surgeon may simply pierce the tendon substance with the second tendon repair device 1001-2 to access the loop 1091. Then the two sutures and needles 1014a, 1014b at the second end 1001b of the second tendon repair device 1001-2 are stitched to the second tendon stump. This embodiment offers another technique for providing a four strand repair between the two tendon stumps.

Ninth Set of Exemplary Embodiments

Figure 11A:
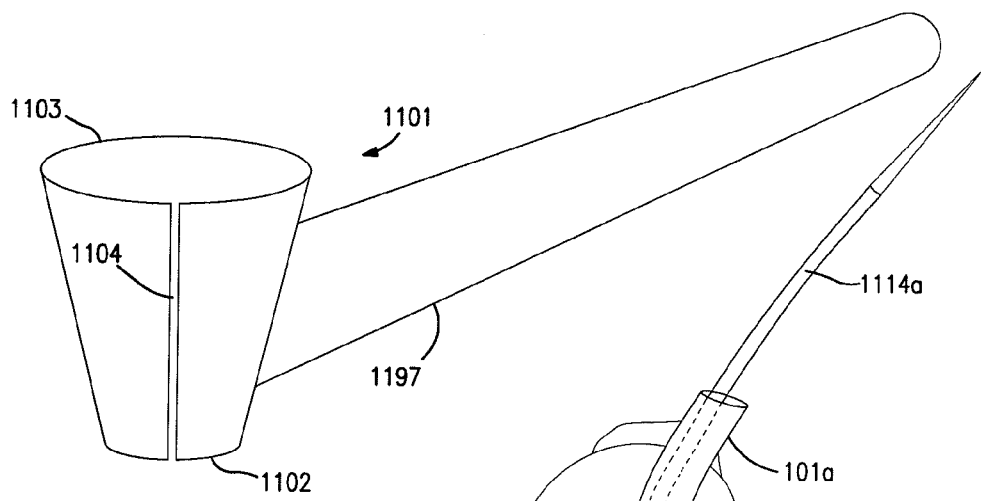
FIG. 11A illustrates an alternative apparatus in accordance with the invention.

FIGS. 11A-11E illustrate alternate embodiments and associated techniques to be used therewith, which techniques can be used in conjunction with some or all of the features and aspects of many of the other embodiments of both the methods and apparatus disclosed herein. FIG. 11A is a perspective view of the apparatus in accordance with this alternate embodiment. Particularly, in this embodiment the flanged catheter is replaced with a guidance member in the form of a funnel 1101.

In a preferred embodiment, funnel 1101 is formed of a biocompatible material, such as a biocompatible plastic, that is relatively rigid, so that it is not easily collapsible. The funnel 1101 comprises a small opening 1102 at one end and a large opening at the other end 1103. Funnel 1101 defines a frustoconical surface when in an unbiased condition, but is split along its entire length, whereby it can be radially spread apart at the split 1104 to resiliently deform the funnel to provide a lateral gap at the split 1104 through which a tendon, ligament or the like can be inserted into the funnel. Alternately, the funnel may overlap somewhat at the split as long as it can be spread apart radially to provide a lateral opening.

The small opening 1102 should be smaller than the entrance to the anatomical passage in connection with which it will be used for introducing a tendon therethrough and the large opening 1103 is larger than the anatomical passage. For instance, in the various embodiments of the invention discussed above in connection with a repair of a finger tendon, the small opening should be sized to help facilitate entry into the pulleys of a finger. The large opening at the other end 1103 of the funnel 1101 should be sufficiently large to readily accept the end of a tendon stump with a tendon repair device stitched thereto. A handle 1197 can be provided extending from the side of the funnel 1101 to facilitate easy manipulation by the surgeon.

Figure 11B:
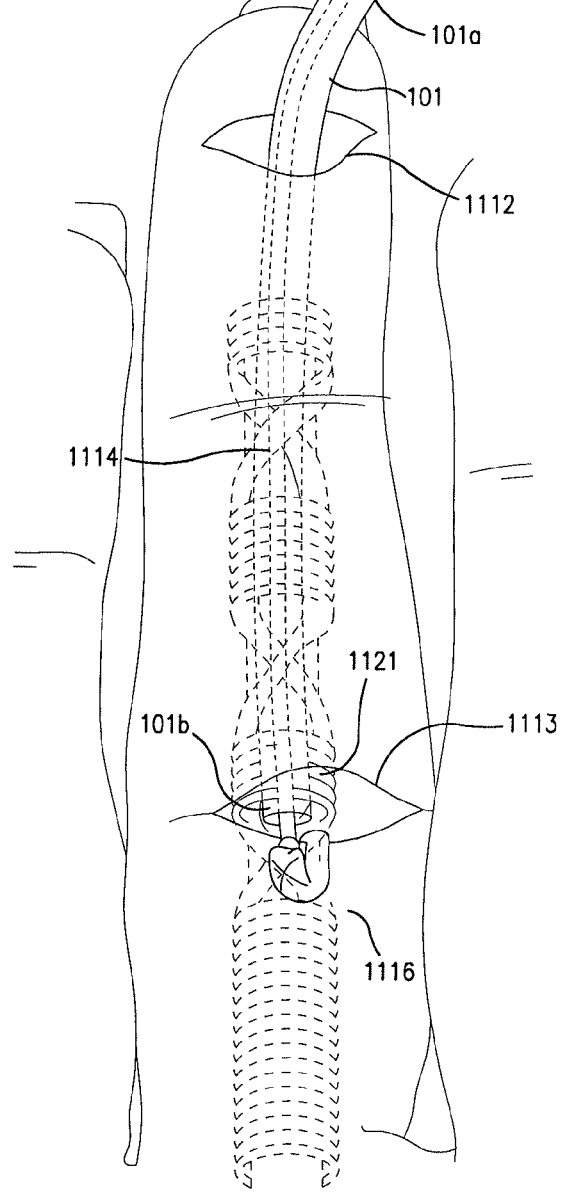
Figure 11C:
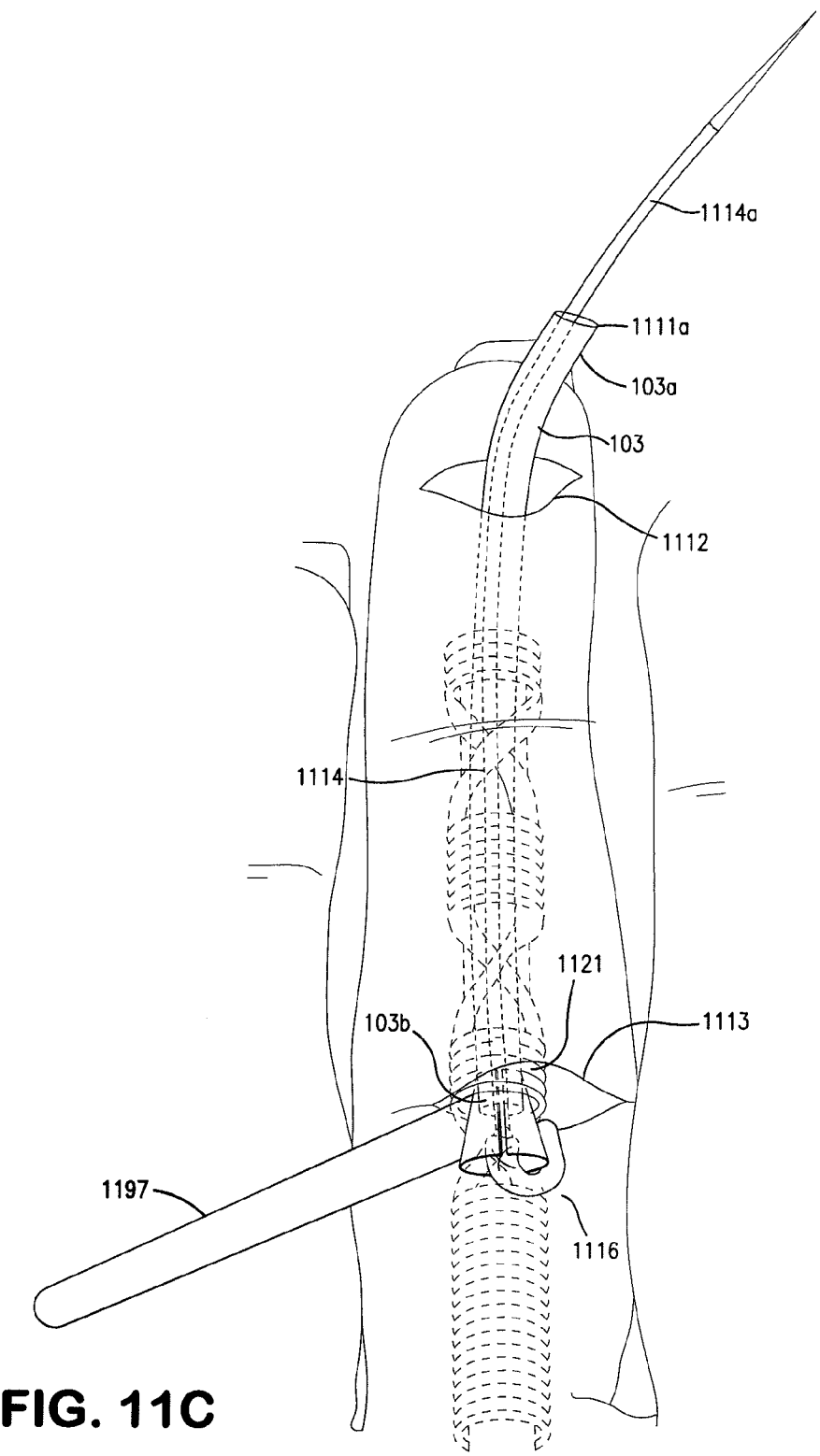

FIGS. 11B-11D illustrate a surgical technique using the funnel 1101. With reference to FIG. 11B, a pulley catheter 103 is positioned through the pulley system of the finger between two incisions 1112, 1113, as previously described, and a tendon repair device 1114, which could be any of the tendon repair devices previously discussed herein, is attached to the end of the proximal tendon stump 1116. Furthermore, the leading end 1114*a* of the tendon repair device 1114 is passed into the pulley catheter 101 also essentially as previously described, except without the use of a flanged catheter 103, the function of which will essentially be replaced by the funnel 1101, as described in detail below.

In this embodiment, the leading end 1114*a* of the tendon repair device 1114 is pushed through the pulley catheter 101 to a point where the end of the tendon stump 1116 is close to, but not touching the trailing end 101*b* of the pulley catheter 101. Next, the pulley catheter 101 and tendon repair device 1114 are pulled distally through the pulley system of the finger from the distal incision 1113 to a point where the trailing end 101*b* of the pulley catheter 101 passes the entrance of the first pulley 1121 that must be traversed, but the tendon stump 1116 is near the entrance to the pulley 1121, but has not passed it yet. Specifically, as previously noted, the end of the tendon stump 1116 is deformed and enlarged and is unlikely to pass easily through the pulley 1121 without a structure to compress it and guide it in. In the previously discussed embodiments, that structure was the flanged catheter 103. In this embodiment, it will be the funnel 1101.

Thus, with reference to FIG. 11C, funnel 1101 is spread apart and slipped over the tendon stump 1116 with the small end 1102 of the funnel facing the entrance to the pulley 1121 and the large end 1103 facing away from the entrance to the pulley. More particularly, the surgeon positions the funnel 1101 in the entrance to the pulley 1121 in order to dilate the pulley 1121 and facilitate the tendon's entering into and passing through the pulley, as shown in FIG. 11C. Funnels of different sizes may be provided as part of a kit in order to accommodate different sized parts of the anatomy and/or different sized patients and to facilitate dilation of the pulley (or other anatomical feature).

With the funnel in the position shown in FIG. 11C, the surgeon can then pull on the leading end 1114*a* of the tendon repair device 1114 to draw the end of the tendon stump 1116 into and through the funnel 1101 and the pulley 1121.

It should be apparent that the primary issue addressed by the funnel 1101 (as well as the flanged portion 159 of the flanged catheter 103 disclosed in connection with previous embodiments) is that often, if not always, the end of the tendon stump with the trailing end of the tendon repair device attached thereto bunches up to become larger than the passageway through the pulley and therefore difficult to insert into and through the pulley. The funnel (as well as the flanged portion 159 of the aforedescribed flanged catheter 103) contains the end of the tendon stump gradually to facilitate insertion into and passage through the pulley (or other narrow anatomical passage as the case may be). The funnel 1101 of this embodiment also serves to dilate the entrance to the pulley to even further facilitate passage.

Unlike the embodiment utilizing the flanged catheter 103, in this embodiment, the funnel 1101 does not pass through the pulleys. It remains in the position shown in FIG. 11C just inside the entrance to the pulley, while the tendon stump 1116 slides through the funnel 1101 and through the pulley 1121. Once the end of the tendon stump 1116 has passed through the pulley 1121, the funnel 1101 is removed. Particularly, it can be spread apart and slipped off the tendon. Alternately, the funnel can be cut away. FIG. 11D shows the repair at this point of the procedure.

If the tendon stump 1116 must be guided through a second or subsequent pulley, the same process is essentially repeated with respect to the second pulley. For instance, if the tendon must pass through a second pulley, then another incision can be made above that pulley (in the corresponding crease of the finger) and the aforescribed process can be repeated using the same or a different funnel. However, the surgeon should first attempt to pull the tendon through without using the funnel, as, often, the tendon might track through a second or subsequent pulley without the help of the funnel.

The tendon stump can then be (1) attached to the distal tendon stump directly, (2) attached to another tendon repair device attached to the distal tendon stump, or (3) be attached to a bone anchor, as the case may be, using any one of the aforedescribed tendon repair devices and/or techniques.

FIG. 11E illustrates an alternate embodiment of the guidance member. The guidance member 1140 in this embodiment is of a split hollow frustoconical form having a smaller diameter end 1143 and a larger diameter end 1144, with a portion of the frustoconical surface removed. The lateral opening 1142 defined by the removed portion of the surface should be sufficiently wide to permit easy insertion of the particular tendon, ligament, or other anatomical feature with which it is intended for use, but sufficiently narrow so as not to permit the tendon to slip out of the member 1140 accidentally. Thus, preferably, the opening is no more than 50% of the conical surface. The opening, for instance, may be about 5%-35% of the conical surface with ⅓ being preferred. In this embodiment, since the guidance member 1140 need not deform to permit the tendon to be inserted therein, it preferably is substantially rigid and not deformable under normal loads. It may be formed of a biocompatible metal, such as stainless steel or titanium. Again, a handle 1198 may be provided to facilitate handling of the guidance member 1140 by the surgeon.

The guidance member 1140 of this embodiment is used essentially exactly as was described above in connection with the funnel 1101 of the preceding embodiment, except that the member 1140 is not be spread apart in order to insert the tendon therein. Rather, the tendon can simply be laid inside the member 1201 through the lateral opening 1142. As in the previous embodiment, a handle 1198 may be provided to facilitate manipulation by the surgeon.

This embodiment is advantageous in that it is easier to insert a tendon in the member. Furthermore, the guidance member is rigid and, therefore, provides more efficient dilation of the anatomy.

FIG. 11F illustrates yet another alternate embodiment of the guidance member. Like the embodiment of FIG. 11A, the guidance member 1150 in this embodiment is a funnel 1151 with a small opening 1152 and a large opening 1153. It is split along its entire length, whereby it can be radially spread apart at the split 1154 to resiliently deform the funnel to provide a lateral gap at the split 1154 through which a tendon, ligament or the like can be inserted into the funnel.

A lip 1156 is provided at the large end to prevent the funnel from being inadvertently pulled through a pulley. A small handle 1157 provides a place for the surgeon to grasp the guidance member 1150. The use of a small handle or merely a lip with no handle at all per se facilitates the ease with which a surgeon may spin the guidance member about its longitudinal axis. Specifically, spinning is sometimes helpful in introducing the small end 1152 of the guidance member into the pulley. A longer handle might interfere with the ability to freely spin the guidance member because a longer handle is more likely to hit an obstruction, such as another part of the patient's hand or another surgical instrument.

In still other embodiments, the guidance member could be formed as a split cone with overlap at the split so as to have a spiral-like shape. The overlap should be relatively small, such as on the order of between about 5° and 90° of radial overlap, and preferably about 70° of radial overlap when unstrained. Particularly, too much radial overlap might make it difficult to spread the guidance member apart sufficiently to open the gap through which the tendon must pass.

Embodiments with overlapping at the split have several advantages. First, the overlap would make it essentially impossible for the tendon to accidentally slip out of the gap in the guidance member once the expansion pressure to open the gap is removed. Second, the overlap will permit some adjustability to the radial size of the guidance member. That is, by applying inward radial force on the outer wall of the guide member, the radius of the guide member can be decreased temporarily to help fit the small opening of the guidance member into a pulley should that be necessary. Conversely, the radius of the guidance member may be temporarily increased should that be necessary to allow a tendon to pass through the opening at the small end of the guidance member, but without opening the gap in the side wall, which might allow the tendon stump to inadvertently escape from the guidance member through the gap). More specifically, if the tendon stump being guided through the pulley system by the guidance member is smaller than the opening at the small end of the guidance member, the pulling force on the tendon repair device and tendon stump will simultaneously also apply a radially outward force on the inner wall of the guidance member. That outward radial force will force the guidance member to radially expand, which will cause the opening at the smaller end to increase in diameter and allow the tendon stump to pass through.

Tenth Set of Exemplary Embodiments

While the invention has been described above in connection with attaching two tendon stumps and/or one tendon stump directly to bone, it should be understood by those of skill in the related arts that it can also be employed in connection with repairs that use a tendon graft. In such situations, one end of the tendon graft is attached to one tendon stump and the other end of the tendon graft is attached to either another tendon stump or directly to bone using the above-described apparatus and techniques. The tendon graft may be taken from another part of the patient's body, such as the patient's foot, or may be an allograft.

In accordance with another aspect of the invention, a thin walled tube that functions as an adhesion barrier may be placed over the tendon at the repair site in order to facilitate the free gliding of the tendon through the pulley system of the finger. More particularly, as an injured tendon, ligament, or other longitudinal anatomical member heals, scar tissue forms around the repair site. During the healing process, the scar tissue can interfere with the free movement of the tendon through the pulley system. Additional surgery may also be needed to remove such scar tissue.

Figure 12C:
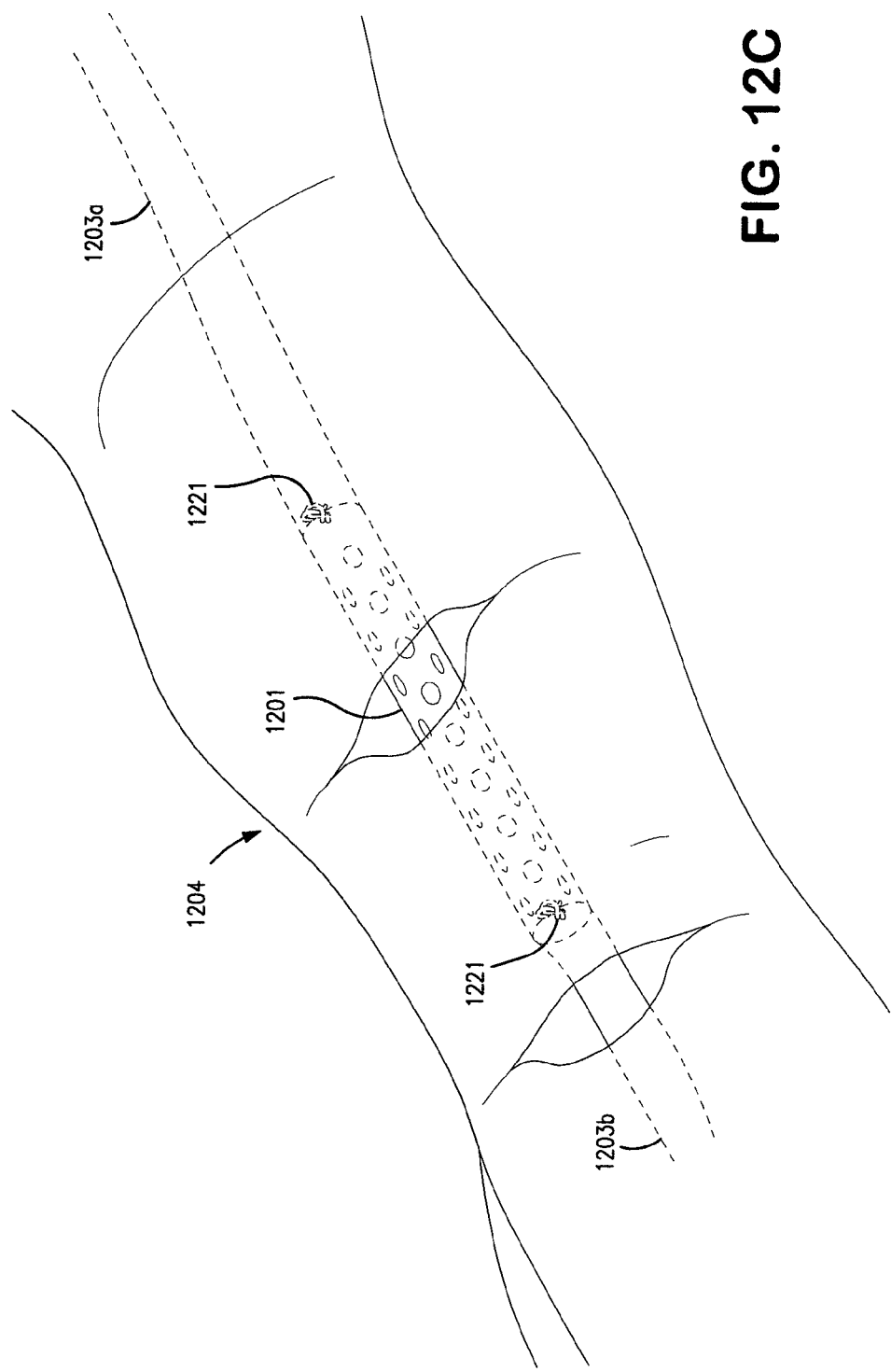

In order to facilitate the free movement of the tendon through the pulley system, the repair site(s) may be encased in an adhesion barrier in the form of a thin walled tube. The adhesion barrier may comprise a thin walled tube 1201 such as illustrated in FIG. 12A. FIG. 12B illustrates one particular embodiment of the adhesion barrier being used in connection with a tendon repair in which two tendon stumps are being reattached without an intervening graft. As shown, the tube 1201 may be slipped over the end of one of the severed tendon stumps 1203a prior to the repair being performed and slid out of the way during the repair process. Then, referring to FIG. 12C, after the repair is completed, the tube 1201 may be slid along the repaired tendon to the repair site 1204 (including the stitches, the tendon repair device, and both tendon stumps 1203a, 1203b). Preferably, the tube 1201 is stitched to the tendon at this point with at least one stitch 1221 and, preferably, with each at least one stitch 1221 at each end of the tube.

The tube will provide a barrier to allow healing to take place along the length of the tendon (inside the tube) rather than outwardly where such scar tissue might interfere with the free movement of the tendon through the pulley system. The tube may also provide guidance for growth on the outside of the tube diameter to bolster the structure that will ultimately provide the passageway for the repaired tissue inside the tube. The external and internal surfaces of the tube should be lubricious and have a low friction coefficient so that it (with the tendon inside of it) can slide freely through the pulley system and allow the tube to be removed after healing has occurred.

The wall thickness of the tube should be as thin as possible so as to add minimal bulk to the tissues being repaired. In the case of flexor tendon repair, wall thicknesses of less than 0.25 mm are contemplated. However, the best wall thickness of the tube depends upon the surgical application of the repair and should proportionally thin compared to the tissue being repaired. The length and diameter of the tube will, of course, be dictated primarily by the particular repair. Furthermore, the tube should be formed of a bio-inert material, such as a material chosen from the family of fluoropolymers of Teflon™, PET, PTFE, and EPTFE or the family of silicone polymers. Preferably, the tube is porous so as to allow fluid exchange therethrough in order to keep the tendon healthy. It may have holes or other openings to facilitate such fluid transfer. Preferably, the holes are small enough so as not to permit tissue ingrowth therethrough. It may also be coated with a lubricant to facilitate sliding through the pulley system (or any other anatomical restrictions). Passive motion of the finger during the healing period of the tendon will also prevent any scar tissue adherence of the tendon to the surrounding tissues through the holes in the tube.

The tube should be long enough to completely cover the repair site. In the case of a repair utilizing a graft, depending on the length of the graft, accessibility and other factors, a single longer tube may be used to cover both ends of the graft or two separate, smaller tubes may be used.

The tube will remain in place for the duration of the healing process, from several weeks to several months. At the end of the process, it may be removed by making one or more small incisions in the patient near one end of the tube and then carefully pulling the tube out of the incision as the surgeon cuts the tube. In alternate embodiments, the tube may be formed of a bioabsorbable material that will simply dissolve over time, provided that the bioabsorbable material does not promote adhesions or a local tissue response as it absorbs. An example of a bioabsorbable material would be a crosslinked Hyaluronic Acid or other bioinert polymer. In yet another embodiment, the adhesion barrier may be provided with a longitudinal slit over its entire length so that no cutting would be necessary when it is removed, but rather, it would simply need to be spread apart to be removed from the tendon. Such an embodiment would also facilitate the option of installing the adhesion barrier over the repair site by spreading it apart and slipping it over the tendon after the repair is completed, thereby eliminating the need to slide it longitudinally over the end of a tendon stump before the repair and then sliding it over the repair site after the repair is completed. This may be advantageous where the repair site is long and/or there is insufficient available length of the tendon stump to slide the adhesion barrier out of the way during the repair procedure.

Eleventh Set of Exemplary Embodiments

FIGS. 13A-13C, and 14A-14C illustrate further alternate embodiments and associated techniques to be used therewith, which techniques can be used in conjunction with some or all of the features and aspects of many of the other embodiments of both the methods and apparatus disclosed herein. FIG. 13A is a perspective view of one embodiment of a unitary dilation catheter in accordance with this set of embodiments. FIG. 13B is a perspective view of one embodiment of a multi-piece dilation catheter in accordance with this set of embodiments. The dilation catheter is designed to fit through and dilate the passage or passages (e.g., pulleys) through which the longitudinal anatomical member (e.g., tendon) must be pulled. As will be described in detail below, it will essentially be used like and serve the same functions as the pulley catheter 101 of the first set of embodiments described in connection with FIGS. 1 and 2A-2L above. However it also will serve to dilate the passage. FIG. 13C is a perspective view of a guide member that may be used in conjunction with the dilation catheter to dilate the passage. Particularly, as will be described in detail below, it may serve essentially as a guidewire for inserting the dilation catheter through the pulley system. However, it is believed that the guide member will be unnecessary in the majority of applications.

The dilation catheter 1301 comprises an elongated tube having a lumen therein. The tube comprises a series of consecutive stepped diameter longitudinal segments 1302, 1303, 1304, 1305, each consecutive segment larger than the previous. The use of four steps in the illustrated embodiment is merely exemplary. Any number of steps is possible. The outer diameters and number of different diameter segments should be determined as a function of the size of the anatomical passage or opening through which the dilation catheter 1301 will pass. We will continue to use the example of a severed tendon in the hand in the following discussion. The smallest diameter segment should be smaller than the diameter of the pulley system of the smallest hand size reasonable through which it must pass so that the smallest diameter segment can pass through any pulley system relatively easily. Each larger diameter segment should be designed to gently and in a gradual, stepped manner dilate the pulley system to a larger size in preparation for passing the tendon stump therethrough. The last, largest diameter segment of the dilation catheter should be at least as large as the largest diameter to which one would reasonably dilate the pulley system of the largest reasonable hand size.

As will be seen from the discussion below, according to one exemplary technique, any segment having a diameter that is larger than needs to be passed through the pulley system of the particular patient simply will not be passed through the pulley. Therefore, the largest diameter segment of the dilation catheter can be virtually any diameter. In one embodiment adapted for use in passing tendons through the pulleys of the fingers, the various segments of the dilation catheter range from a smallest diameter of about 10 French to a largest diameter of about 18 French. In one embodiment, this is accomplished with nine segments of 10 F, 11 F, 12 F, 13 F, 14 F, 15 F, 16 F, 17 F, and 18 F diameters. Each segment may be about 10 cm in length.

In one embodiment such as illustrated in FIG. 13A, the dilation catheter 1301 can be unitary. If, prior to or during the surgical procedure, the surgeon determines that any of the smaller diameter segments are clearly smaller than will be needed and/or any of the larger diameter segments are larger than will be needed, the surgeon may simply cut them off prior to use or during the procedure. Hence a single dilation catheter can be offered that can be used in a large number of different anatomical passages and with a large number of different sized patients, thus reducing the number of different versions of the dilation catheter that need to be manufactured.

In another embodiment of the dilation catheter 1310 such as illustrated in FIG. 13B, each diameter segment 1311, 1312, 1314, et seq. may be separable from each other. For instance, in one simple embodiment, each catheter segment may have a neck portion 1315 near its proximal longitudinal end sized to mate in an interference fit with the distal end of the next smaller diameter segment. Preferably, the necked down portion is sized to fit within the distal end of the next smaller segment so that the edges of the longitudinal ends of the various segments will not be exposed on the outside of the dilation catheter 1310.

Like the pulley catheter 101, the dilation catheter preferably is formed of a biocompatible, low friction material having a wall thickness sufficient to make the entire catheter sufficiently stiff to be pushed through the pulley system and to serve the purpose of dilating (holding open) the pulleys against their natural size, yet soft and resilient enough to track through curves in the anatomical passage through which it must pass. It might, for instance, have the approximate flexibility of a typical surgical vascular catheter. The inner diameter of all of the segments should be large enough to easily accommodate the tendon repair device that will be used with the dilation catheter.

In yet other embodiments, the dilation catheter need not have discrete segments of different diameter, but may be continuously tapered over its entire length. As in the segmented embodiments, any portion or portions of the catheter clearly not necessary for the surgery may be cut off before insertion and any portion not necessary after insertion may be curt off after the dilation catheter is in place in the anatomical passage.

FIG. 13C illustrates an optional guide member 1320. As shown, the guide member comprises an elongate member having an outer diameter smaller that the inner diameter of lumen in the smallest diameter segment of the dilation catheter so that the dilation catheter may pass over the guide member easily. In other words, the entirety of the lumen of the dilation catheter is of sufficient size and shape to accept the guide member 1320 therethrough. The guide member 1320 may be cannulated. Alternately, it may be solid (e.g., essentially a guidewire). The guide member should be relatively stiff so that it can be pushed through the pulley system without kinking, yet sufficiently flexible to track through curves in the anatomical passages through which it will be passed in accordance with the techniques disclosed herein. The outer diameter of the guide member should be substantially smaller than the anatomical passage through which it must pass.

In most practical embodiments, the guide member and dilation catheter will both be cylindrical. However, a cylindrical cross-section is not necessary, and, depending on the particular anatomical passage through which the guide member and dilation catheter will be passed, other shaped cross-sections may be preferable. The term diameter is used in this application in a non-limiting manner and not to imply that the cross-section necessarily is cylindrical.

Preferably, each of the segments of different diameter of the dilation catheter is long enough to individually traverse the entire length of the anatomical passage through which it will be passed and stick out sufficiently at each end thereof to provide easy access thereto to the surgeon. Particularly, as will be discussed in detail further below, after the dilation catheter is placed through the relevant anatomical passage, all segments other than the largest segment that fit through the passage can be cut off or removed. For a human hand, 10 cm should be sufficient.

The dilation catheter (and optional guide member) is used to dilate the pulley system so as to best assure that the tendon stump will be able to pass through the pulley system without binding. Both the guide member and the dilation catheter are hollow tubes formed of a biocompatible polymer of such composition and/or wall thickness so that it is bendable, but sufficiently rigid to be pushed through a pulley system. The relative rigidity of the dilation catheter and guide member will permit it to be pushed through narrow anatomical passages, such as the pulleys of the fingers. However, its flexibility will permit some bending to accommodate an overall curved path. Preferably, the dilation catheter is formed of a material having a low friction coefficient to allow the dilation catheter to readily pass through and around bodily tissues such as the tendon pulley system. Suitable biocompatible polymers include homopolymers, copolymers and blends of silicone, polyurethane, polyethylene, polypropylene, polyamide, polyaryl, flouropolymer, or any other biocompatible polymer system that meets the mechanical characteristics above (PELLETHANE™ a DOW thermoplastic polyurethane elastomers (TPU), which is commonly use in other dilating catheters is targeted for this device.)

The required low coefficient of friction of the surfaces of the dilation catheter may be inherent to the materials used to construct the device or may be enhanced through a surface preparation such as a lubricious coating or mechanical modification of the surface such as longitudinal recesses.

The particular length, material, wall thickness, inner diameter, outer diameter, and stiffness of the dilation catheter will vary depending on the particular tendon or ligament with which is it to be used.

The inner diameter should be large enough to easily accommodate the cable portion and straight needle of the tendon repair device. The particular material and cross sectional geometry (e.g., wall thickness) of the dilation catheter will largely dictate the stiffness of the catheter and, as noted above, should be selected to provide enough rigidity to allow it to be pushed through a narrow path, but flexible enough to bend to accommodate bends in the path. In the exemplary case of the flexor digitorum profundus at the level of the middle phalanx, the pulley catheter may be formed of silicone and be 120 millimeters in length with a wall thickness of 0.5 mm, and an outer diameter of 2 mm. A biocompatible elastomer having a durometer of 50-90 (Shore A) may be used for the dilation catheter.

Similarly to the pulley catheter 101 of FIG. 1, the dilation catheter, with or without the guide member, can be used in connection with a tendon or other repair using virtually any of the tendon repair devices and related accoutrement described herein and in conjunction with virtually any of the surgical techniques described herein.

Figure 14B:
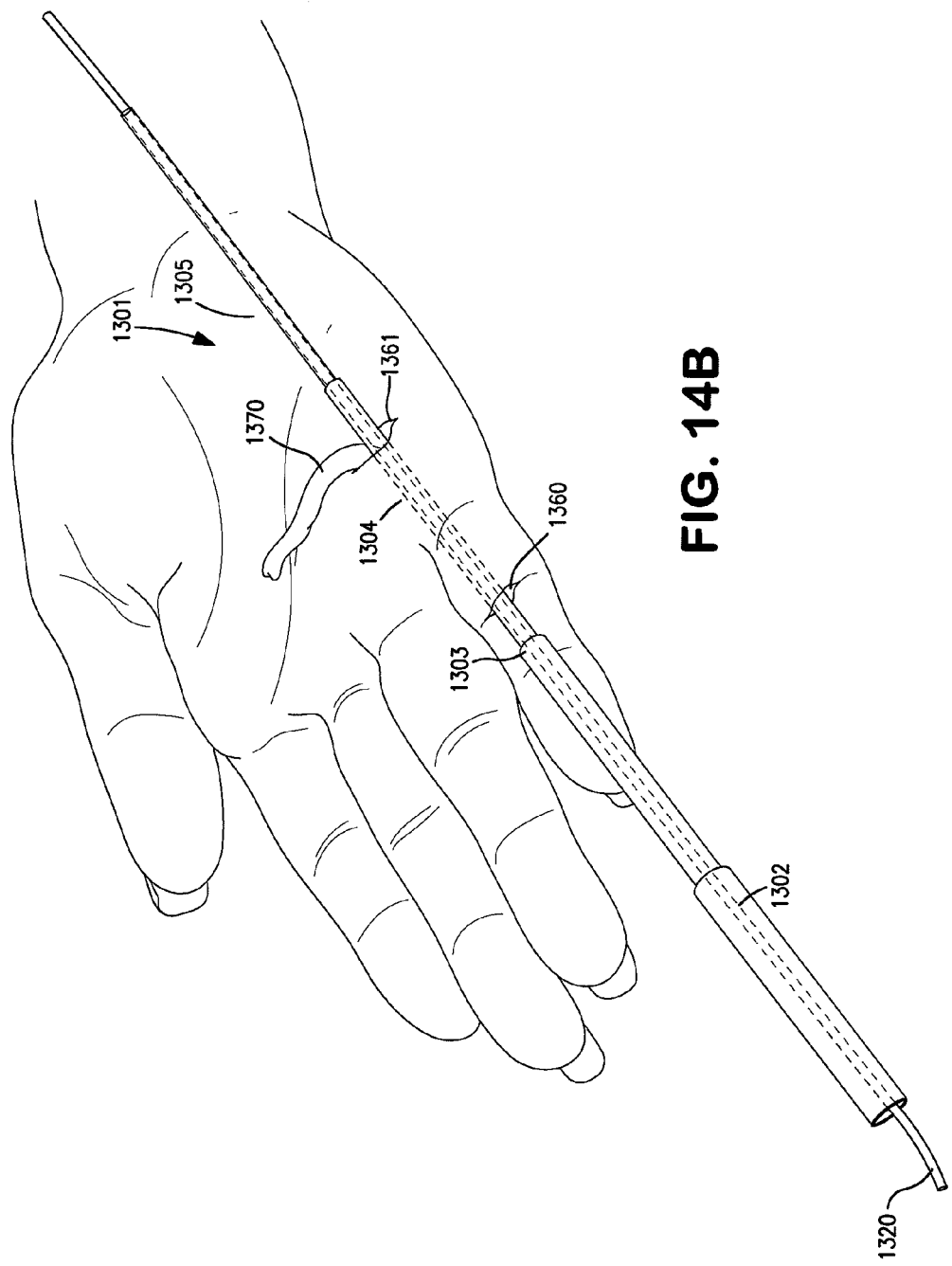

FIGS. 14A-14G illustrate various stages in an exemplary surgical procedure to reattach a severed tendon. If the tendon stump has retracted and must be retrieved from a first incision into a second incision (or the wound), as is typical of tendon lacerations in the hand, first, an incision 1361 is made, typically in the palm of the hand, as illustrated, where the proximal tendon stump 1370 can be retrieved. If, on the other hand, the proximal tendon stump is distal to the A2 pulley, then the tendon would be exposed through an incision just distal to the A2 pulley. Referring first to FIG. 14A, if a guide member is used, the guide member 1320 is passed into the wound or incision 1360 at the laceration site and slowly pushed proximally toward the other incision 1361 beneath the A3 pulley through the pulley system of the finger. If resistance is encountered such that the pulley catheter cannot be pushed through proximally, then a ½ cm to 1 cm incision (not shown) may be made midway between the skin creases of the proximal interphalangeal joint of the finger and the crease at the base of the finger. This is at a level between the A2 pulley and the A3 pulley of the finger. The dissection is carried down gently to the flexor sheath where the pulley will be found. The dilation catheter 1301 can then be pulled past the obstruction or resistance through this incision. The guide member 1320, if used, should be long enough to pass entirely through the pulley system and stick out at both ends. If the guide member is substantially longer than the desired length, it may be cut to a suitable length either before it is inserted or after.

With reference to FIG. 14B, once the guide member 1320 is in place, the dilation catheter 1301 (or 1310) is slipped through the pulley system over the guide member 1320 working from distal to proximal. Particularly, the smallest diameter portion 1302 is slipped over the guide member 1320 and pushed over the guide member through the pulley system until it exits the other incision. In embodiments omitting the guide member 1320, the smallest diameter segment of the dilation catheter 1301 is simply inserted through the pulley system just as described above for the guide member.

In either event, the smallest diameter segment of the dilation catheter is slid back-and-forth about 10 mm to enlarge the annular rings. Then the next larger catheter segment is pulled through and slid similarly. This continues for each longitudinal segment of the dilation catheter until the surgeon determines that the annular rings in the pulley system are enlarged enough to accept passage of the tendon stump. Generally, this will be at about the 14, 16, or 18 French diameters for most hands. This largest fitting catheter size is centered between the two surgical wounds 1360, 1361. In this example, segment 1304 is the largest segment passed through the pulley system.

With reference to FIG. 14C, once the dilation catheter 1301 is in place, the guide member, if used, 1320 may be removed.

Figure 14D:
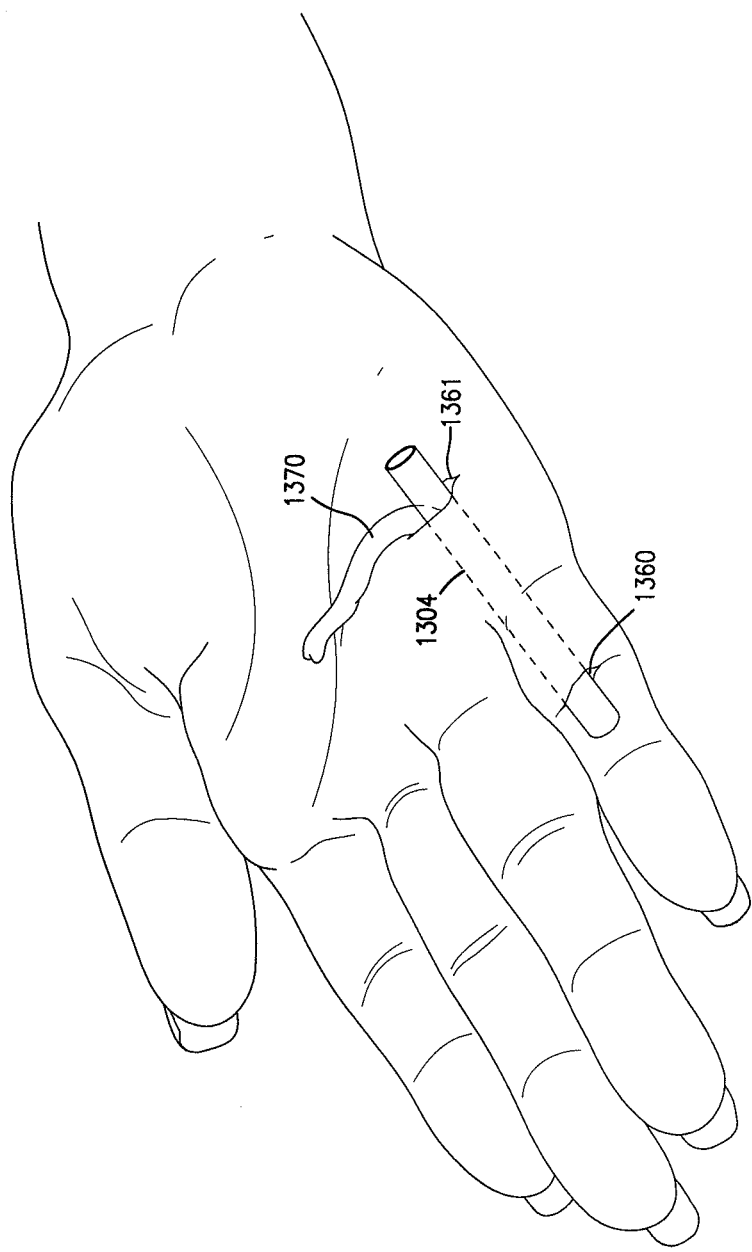

With reference to FIG. 14D, at this point, all of the segments of the dilation catheter other than the one traversing the pulley system can be removed. As previously mentioned, if the dilation catheter is unitary, then the other diameter segments of the dilation catheter can be cut off. On the other hand, if the dilation catheter comprises multiple separable segments, then the other segments can simply be pulled off. In addition, the surgeon also may cut off part of the remaining segment if it is longer than needed.

At this point, the surgical procedure to reattach the tendon stump can be performed essentially as described in accordance with any of the embodiments discussed previously in this specification, with the tendon repair device and tendon stumps being passed through the dilation catheter rather than the pulley catheter.

Figure 14E:
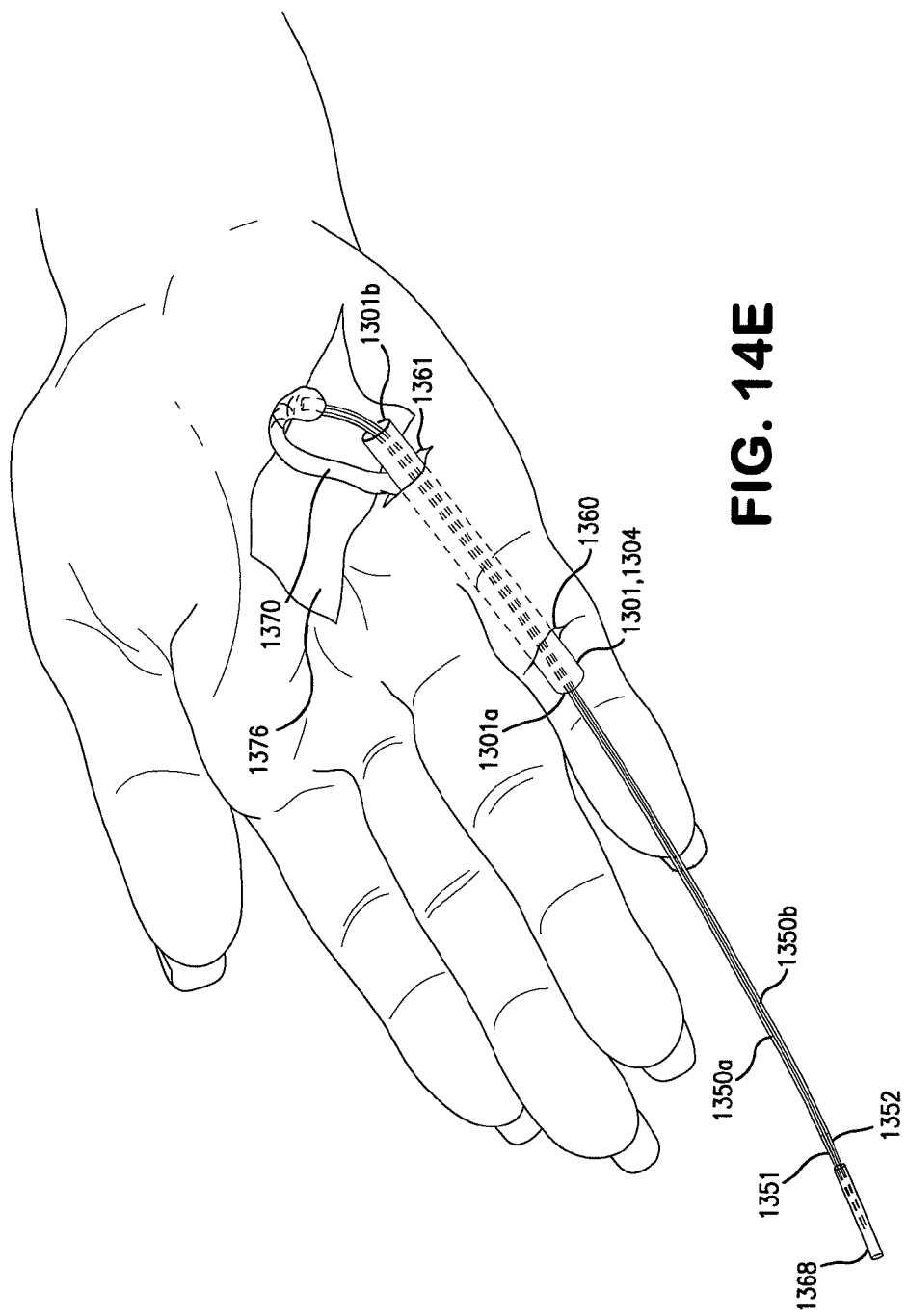

Thus, for example, with reference to FIG. 14E, a flexible barrier 1376 is placed under the tendon holder to create a working 'table' for suture repair and a tendon holder may be used to pierce the tendon stump to hold the tendon stump for stitching. Next, a tendon repair device, which could be any of the tendon repair devices previously discussed herein, is attached to the end of the tendon stump 1370. FIGS. 14A-14G, illustrate an embodiment in which a single suture 1401 with a needle 1402, 1403 at each end thereof is used to perform the repair. In this embodiment, one needle may be curved and the other straight or both needles may be straight. In fact, a repair could be performed with a needle on only one end of the suture; however, having a needle at each end is advantageous and will allow the stitching to be performed much faster since the surgeon can stitch from both ends of the suture. In any event, the suture is stitched to the proximal tendon stump using the needle(s). A modified cruciate stitching technique, as will be discussed in more detail below in connection with FIG. 15, provides a particularly advantageous stitch because it is a locking stitch.

Once the tendon repair device 1350 is securely fixed to the proximal tendon stump 1370, the tendon stump is removed from the tendon holder, if used. Next, the loose end(s) 1350a, 1350b of the suture 1350 are passed all the way through and out of the other end of the dilation catheter 1301 (essentially as previously described in connection with the pulley catheter 101). Stainless steel sutures typically have sufficient rigidity to permit them to be pushed through the dilation catheter segment. In fact, multifilament stainless steel sutures such as described above in connection with previous embodiments of the suture repair device are particularly suitable because they are strong, exhibit little, if any, shape memory, and hold knots quite well. One exemplary suture is the multifilament stainless steel 4-0 (MFSS) suture available from Fort Wayne Metals of Fort Wayne, Ind., USA. The MFSS comprises 49 wound filaments of 0.023" diameter 316L stainless steel wire. There are seven sets of seven wires wound with each other, each set comprising seven wires wound with each other.

Whichever type of suture is used, it may be desirable to lodge at least the tips of the needles on the ends of the suture in a small diameter rod that is smaller than the inner diameter of the dilation catheter before passing them through the dilation catheter 1301. This will help prevent the needles from sticking into the side of the lumen of the dilation catheter 1301 and getting stuck. In one embodiment, the rod may be a small, double lumen tube, and each needle 1351, 1352 may be inserted into one of the lumens. The lumens may be sized so that the needles 1351, 1352 fit within the respective lumens in a friction fit. Alternately, the rod may be solid (i.e., not a hollow tube with a lumen) and made of a material soft enough to be punctured by the needles so that the needles could be pushed into the end of the rod, like a pin cushion. FIG. 14E illustrates yet another embodiment, in which a tube 1368 has a single lumen sized to accept both needles 1351, 1352 together in a friction fit. The tube 1368 need be only long enough to accept the tips of the needles and provide a sufficient length over the needles to form a reasonable friction fit so that the tube does not fall of the needles.

In other embodiments, if one of the needles is a curved needle, the needle can be cut off after stitching and the bare suture end can be inserted into the tube 1368 along with the needle at the other end of the suture. In yet even further embodiments, only one end of the suture may be passed through the dilation catheter 1301. Thus, the other end of the suture may have a curved needle that is simply cut off after stitching or no needle at all.

In any event, FIG. 14F illustrates yet another possible embodiment. In this embodiment, the tube 1368 of FIG. 14E is replaced with a much longer tube or rod 1380. Tube or rod 1380 is long enough to be passed through the dilation catheter in the distal to proximal direction and extend from both ends of the dilation catheter. After the suture 1350 (or other tendon repair device) has been stitched to the tendon stub 1370, the needle(s) 1351, 1352 can be inserted into the proximally facing end 1380a of the tube 1380 and the surgeon can grasp the distally facing end 1380b of the tube or rod that is protruding from the distal end of the dilation catheter 1301 and pull the suture(s)/tendon repair device 1350 through the dilation catheter, rather than pushing it through. This embodiment is advantageous in that it allows other types of suture(s), such as nylon sutures, that may not have sufficient stiffness to be pushed through the dilation catheter, to be used in the repair. Alternately, a short tube, rod, block or anything to which the needles can be temporarily affixed (e.g., by sticking, adhesive, tape etc.) may be attached to the end of any longitudinal member (e.g., another suture, a narrow surgical instrument) that is thin enough to fit within the dilation catheter in order to pull the sutures through the dilation catheter.

In any event, after the tendon repair device/suture 1350 is through the dilation catheter and extending from its distal end 1301a, if the stitched end of the tendon stump 1370 is sufficiently small to pass into the dilation catheter itself, it can be pulled just into the proximal end 1301b of the dilation catheter 1301 and then the dilation catheter 1301, tendon repair device/suture(s) 1350, and tendon stump 1370 can be pulled through the pulley system as a unit as previously described in connection with the pulley catheter 101 of FIG. 1.

Figure 14G:
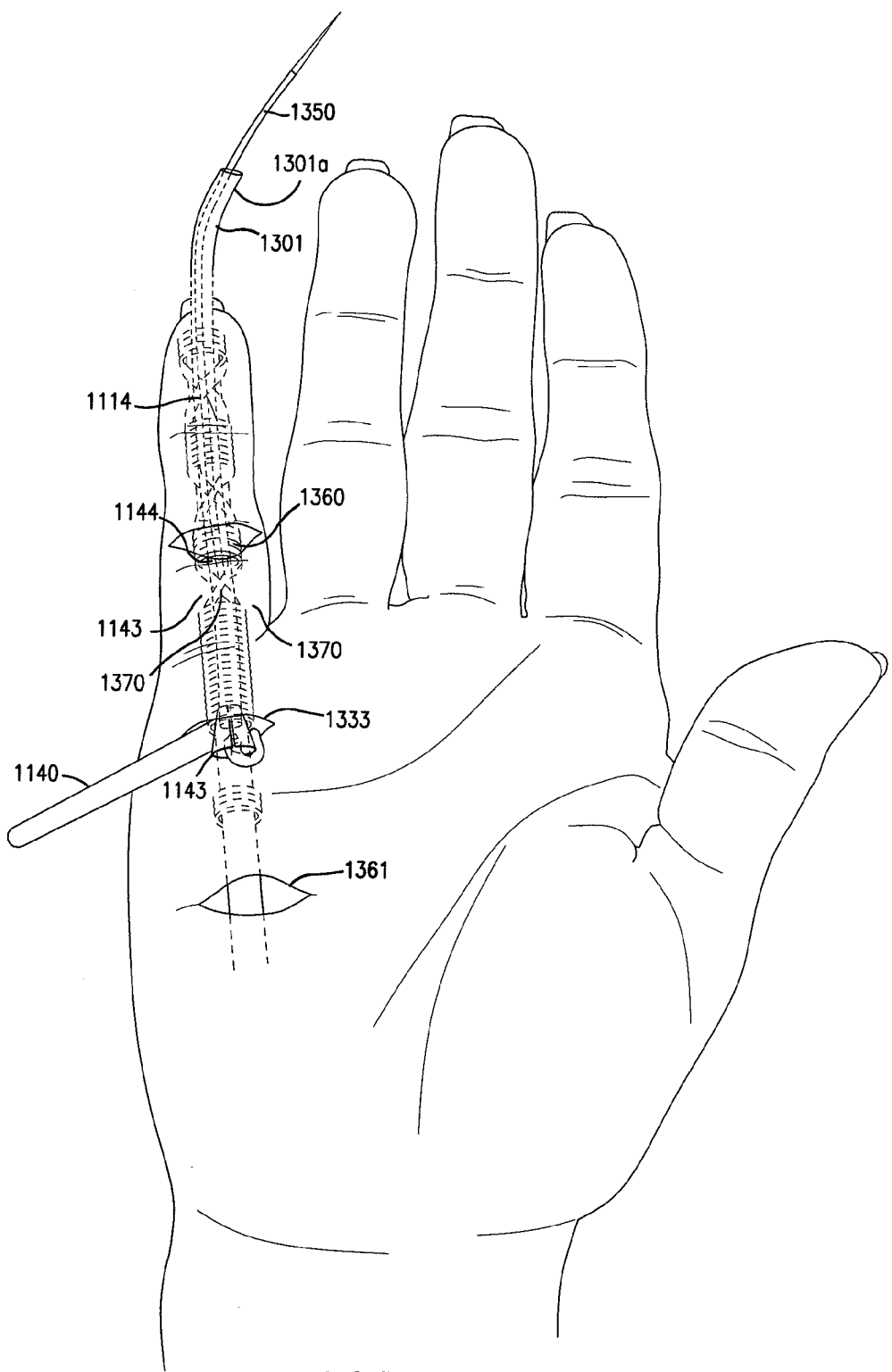
Figure 15:
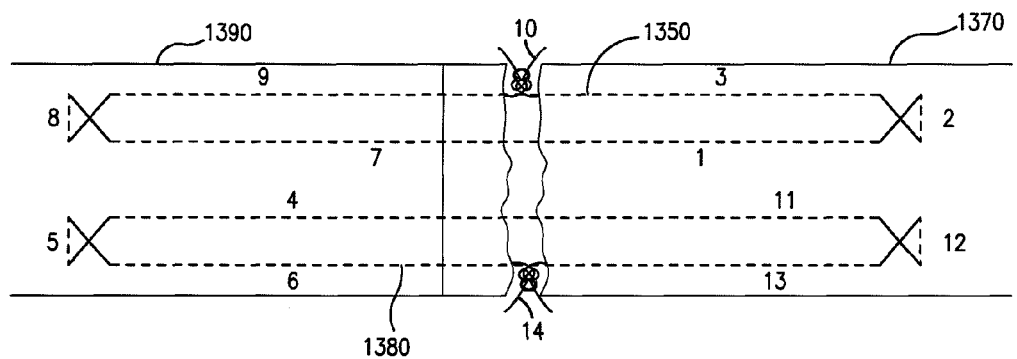
FIG. 15 illustrates a tendon bearing a modified cruciate repair stitch.

However, with reference now to FIG. 14G, most likely the tendon stump 1370, because of its deformation and excess bulk due to the stitching, will not readily fit within the dilation catheter 1301. In such cases, the leading end of the tendon repair device 1350 is pushed or pulled through the dilation catheter 1301 to a point where the end of the tendon stump 1370 is close to, but not touching the trailing end 1301b of the dilation catheter 1301, as seen in FIG. 14G.

Next, the dilation catheter 1301, tendon repair device 1350, and tendon stump 1370 are pulled as a unit through the pulley system to a point where the trailing end 1301b of the dilation catheter 1301 has passes the entrance of the first pulley 1321 that must be traversed with the end tendon stump 1370 is near the entrance to the pulley 1321, as shown in FIG. 14G. This may require the making of an additional incision 1333 adjacent an end of the pulley if the existing incisions are not already adjacent the pulley entrance. In fact, as will become clear, such an additional incision may be necessary for each separate pulley that must be traversed. A funnel, such as 1140 of FIG. 11E, is slipped over the tendon stump 1370 with the small end 1143 of the funnel positioned slightly inside of the entrance to the pulley 1121 and the large end 1144 facing away from the entrance to the pulley.

With the funnel 1140 in the position shown in FIG. 14G, the surgeon can then pull on the leading end of the tendon repair device 1350 and dilation catheter 1301 to draw the end of the tendon stump 1370 into and through the funnel 1140 and the pulley 1321.

The funnel 1140 contains the end of the tendon stump 1370 gradually to facilitate insertion into and passage through the pulley 1321. The tendon stump 1370 slides through the funnel 1140 and through the pulley 1321. Once the end of the tendon stump 1370 has passed through the pulley 1321, the funnel 1140 is removed, as seen in FIG. 14G.

The dilation catheter 1301 may be provided with mm markers on its surface to assist in determining exactly where a hidden blockage is positioned (and a new incision must be made) when pulling the tendon through the pulley system with the dilation catheter. Particularly, the specific mm mark at the skin in the incision is noted prior to pulling the tendon through the finger. If a resistance is encountered, then the mm marking at the same location of the skin is noted. The exact site of the blockage is calculated by determining the difference between the two observed markings and measuring the equivalent distance on the skin surface of the patient.

If the tendon stump 1370 must be guided through a second or subsequent pulley, the same process using the funnel 1140 is repeated with respect to the second or subsequent pulley.

If there is a distal tendon stump that has retracted and must be passed through a different portion of the pulley system in the opposite direction, then that can be done using the techniques and apparatus just described, but working in the opposite direction.

The tendon stump 1370 can then be (1) attached to the other, mating tendon stump directly, (2) attached to another tendon repair device attached to the other, mating tendon stump, or (3) be attached to a bone anchor, as the case may be, using any one of the aforedescribed techniques. Particularly, the two tendon stumps are brought together in an abutting condition and the needle(s) and suture(s) extending from the proximal tendon stump are stitched to the distal tendon stump. A tendon holder may be used to help bring or hold the tendon stumps together by adjusting the positions of the needles of the tendon holder toward the center so that they are very close to each other and piercing each tendon stump with one of the needle pairs. The needle(s) and suture(s), if any, previously attached to and extending from the distal tendon stump can also be stitched to the proximal tendon stump to double the strength of the repair. Again, a modified cruciate stitch may be used.

FIG. 15 illustrates the aforementioned modified cruciate repair stitch as used in the exemplary repair procedure of FIGS. 14A-14G. The numbers 1-14 in FIG. 15 provided alongside some of the linear segments of the sutures and near the knots help indicate the chronological order of the stitching steps. The dashed lines indicate that the suture is within the substance of the tendon and the solid lines indicate that the suture is on the surface of the tendon.

Chronologically, (1) the first suture 1350 is stitched to the proximal tendon stump 1370 using a modified cruciate stitch as shown (steps 1-3), (2) a second suture 1380 is stitched to the distal tendon stump 1390 also using a modified cruciate stitch as shown (steps 4-6), (3) after the two tendon stumps are brought together (a tendon holder may be used to help bring or hold the tendon stumps together by adjusting the positions of the needles of the tendon holder toward the center so that they are very close to each other and piercing each tendon stump with one of the needles or needle sets), the first suture is then stitched to the distal tendon stump using another modified cruciate stitch (steps 7-9), (4) the two ends of the first suture are tied together with a knot (steps 10), (5) the second suture is stitched to the proximal tendon stump with another modified cruciate stitch (steps 11-13), and (6) the two ends of the second suture are tied together with a knot (steps 14). Finally, although not shown in FIG. 15 in order not to obfuscate the illustration of the modified cruciate stitches, one or more epitendonous stitches (using 6-0 Ethibond™) may be applied circumferentially at the repair junction.

Figure 16:
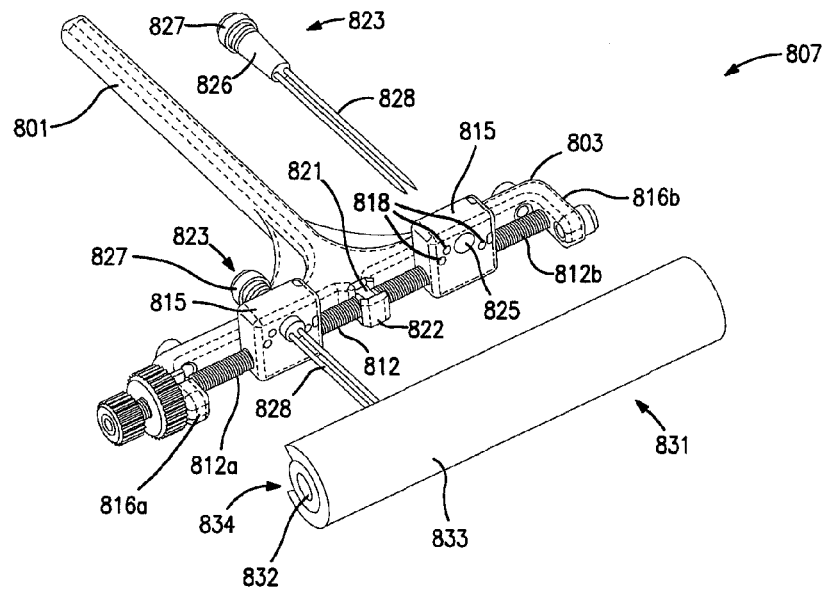
FIG. 16 is a perspective view of a tendon holder in accordance with another embodiment of the invention.

FIG. 16 is a perspective view of another embodiment of a tendon holder. In this embodiment, the tendon holder 807 still comprises a handle 801, and a cross bar 803 at the distal end of the handle 801. In this embodiment, the cross bar holds a turnbuckle 812 (essentially a screw with oppositely directed threads on each half 812a, 812b of its length) between two rotatable mounting points 813, 814 on arms 816a, 816b. A knob is attached to at least one end of the turnbuckle to permit the surgeon to rotate the turnbuckle. A needle holder block 815 is threadedly mounted on each half 812a, 812b. Thus, when the turnbuckle 812 is rotated in one direction, the two needle holder blocks 815 approximate each other (i.e., they move medially toward each other on the turnbuckle 812. When the turnbuckle 812 is rotated in the other direction, the two needle holder blocks 815 move laterally away from each other on the cross bar 803. An unthreaded larger diameter cylindrical portion 821 of the turnbuckle 812 exactly in the middle of the turnbuckle may be provided to prevent the two needle holder blocks 815 from hitting each other. A support block 822 may hold the unthreaded cylindrical portion 821 rotatably therein to provide support for the turnbuckle 812 intermediate its two ends.

Each needle block can hold a number of different needles in different configurations. Particularly, each needle block 815 includes a transverse threaded hole 825 for accepting a needle holder 823. The needle holder 823 comprises a screw shank 826 with mating threads to the transverse threaded holes and a head 827 at its proximal end for manually rotating the screw 826 into the transverse hole 825 of the needle block 815. One or more needles 828 extend from the distal end of the screw 826 for holding tendons. Different needle holders with different numbers and configurations of needles can be provided for addressing different surgical conditions.

Each needle block 815 further comprises one or more additional holes 818 through which needles or K-wires may be inserted. The various holes 818 may be oriented at different angles in order to provide a plurality of choices as to the angle(s) at which the needle(s) or K-wire(s) extend from the block. Particularly, when the apparatus and techniques of the present invention are used to reattach a tendon or ligament that has avulsed from the bone, rather than been lacerated, one of the blocks can be used to attach the tendon holder to the bone, rather than one of the tendon stumps. Then, the tendon holder can be to approximate the tendon stump to the bone. For instance, one or more a K-wire may be passed through one or more of holes 818 of one of the blocks 816 and stuck into the bone to which the avulsed tendon stump is to be reattached (such as by any of the techniques described above in connection with FIGS. 4A-4D). The needle(s) of the other block 816 are stuck into the tendon stump and the turnbuckle is turned to approximate the tendon stump to the bone.

In use, the turnbuckle can be turned to position the needles with a desired spacing relative to each other before piercing the tendon stump(s) with the needles. Alternately, two tendon stumps that are to be rejoined can be pierced with one of the needles (or plurality of needles) and then the turnbuckle can be turned to draw the needle blocks medially toward each other to bring the stumps into abutting contact.

A stabilizer bar 831 may be provided for use with the tendon holder, into which the tips of the needles 828 can be stuck both before and during surgery. The stabilizer bar 831 may be a cylinder formed of a relatively soft cylinder of material 832 that the needles can penetrate relatively easily that is partially wrapped in a second annulus of harder material 833 with a gap 834 through which the soft inner material 832 is accessible for sticking the needles into it. The harder outer material 833 is much more difficult to penetrate with the needles, and thus will prevent the needles from poking all the way through the stabilizer bar 831 and becoming exposed again. Alternately, the stabilizer bar may be formed unitarily of materials with two different hardnesses, such as by a dual extrusion process.

Both before and during surgery, the stabilizer bar 831 can serve several functions. First, it protects the needle tips, preventing the surgical personnel from inadvertently sticking themselves or anything else with the needles. Second, it braces the needles, creating a rectangular structure that helps prevent the needles from inadvertently being bent out of shape. Finally, during surgery, it can prevent the tendon stumps from becoming inadvertently disengaged from the needles.

Conclusion

Preliminary testing has shown failure strengths of tendon reattachments performed in accordance with the principles of the present invention of approximately 70-100 Newtons. Accordingly, a tendon and ligament repair in accordance with the principles of the present invention results in a much stronger result that the current standard of care.

In addition, the procedure is greatly simplified as compared to the present standard of care.

The present invention provides a safe, simple, easy, and strong repair for tendons, ligaments, and the like. In preliminary tests, failure strengths of up to 100 N have been observed.

It should be understood that the numbers of sutures/cables and needles forming the various parts of the tendon repair devices described in association with the various embodiments herein are merely exemplary and that fewer or more sutures/cables (and needles) may be provided depending on the desired strength of the repair, the particular tissue that is being repaired, the strength of the material from which the tendon repair device is manufactured, and other factors.

Even though description of the utility of the various embodiments was limited to the flexor tendons of the hand, it must be understood that many soft tissue repairs can be carried out by use of the device as described, either in part of in full. Examples of such anatomical structures include the tendons and ligaments of the body as well as any other structure require fixation in multiple points, subsequently attached to soft tissue or to bone.

Having thus described particular embodiments of the invention, various alterations, modifications, and improvements will readily occur to those skilled in the art. Such alterations, modifications, and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

The invention claimed is:

1. A method of retrieving through an anatomical passage a first stump of a longitudinal anatomical feature for reattachment to another anatomical feature, the method comprising:
providing a first repair device having a first longitudinal end and a second longitudinal end, the first repair device including at least one filament having a first longitudinal end defining the first longitudinal end of the first repair device and a second longitudinal end defining the second longitudinal end of the first repair device, a first needle attached to the first end of the at least one filament;
retrieving the first stump through a first opening in a patient;
stitching the at least one filament to the first stump using the first needle;
passing a catheter having a first longitudinal end and a second longitudinal end through the anatomical passage between the first opening and a second opening;
inserting at least the second longitudinal end of the at least one filament of the first repair device into the catheter from the first opening; and
pulling the catheter, the first repair device, and the first stump attached to the first repair device from the second opening,
wherein the inserting comprises passing the at least one filament through the catheter to a point where the second longitudinal end of the first filament extends from the second longitudinal end of the catheter and an end of the stump is adjacent the first longitudinal end of the catheter,
wherein the passing comprises inserting at least a portion of the at least one needle into a rod and pushing the filament, needle and tube through the catheter from the first opening to the second opening.

2. The method of claim 1 wherein the rod is a tube having a lumen and wherein the inserting comprises inserting the at least one needle into the lumen in the tube.

3. A method of retrieving through an anatomical passage a first stump of a longitudinal anatomical feature for reattachment to another anatomical feature, the method comprising:
providing a first repair device having a first longitudinal end and a second longitudinal end, the first repair device including at least one filament having a first longitudinal end defining the first longitudinal end of the first repair device and a second longitudinal end defining the second longitudinal end of the first repair device, a first needle attached to the first end of the at least one filament,
retrieving the first stump through a first opening in a patient,
stitching the at least one filament to the first stump using the first needle,
passing a catheter having a first longitudinal end and a second longitudinal end through the anatomical passage between the first opening and a second opening,
inserting at least the second longitudinal end of the at least one filament of the first repair device into the catheter from the first opening, and
pulling the catheter, the first repair device, and the first stump attached to the first repair device from the second opening,
wherein the inserting comprises passing the at least one filament through the catheter to a point where the second longitudinal end of the first filament extends from the second longitudinal end of the catheter and an end of the stump is adjacent the first longitudinal end of the catheter wherein the passing comprises:
inserting a tube through the catheter and extending from both ends of the catheter;
subsequently lodging at least a portion of the at least one needle into the tube from the first opening; and
pulling the tube through the catheter from the second opening, whereby the needle and filament are pulled through the catheter from the first opening to the second opening.

4. A method of retrieving through an anatomical passage a first stump of a longitudinal anatomical feature for reattachment to another anatomical feature, the method comprising:
providing a first repair device having a first longitudinal end and a second longitudinal end, the first repair device including at least one filament having a first longitudinal end defining the first longitudinal end of the first repair device and a second longitudinal end defining the second longitudinal end of the first repair device, a first needle attached to the first end of the at least one filament, retrieving the first stump through a first opening in a patient, stitching the at least one filament to the first stump using the first needle, passing a catheter having a first longitudinal end and a second longitudinal end through the anatomical passage between the first opening and a second opening, inserting at least the second longitudinal end of the at least one filament of the first repair device into the catheter from the first opening, and pulling the catheter, the first repair device, and the first stump attached to the first repair device from the second opening, wherein the inserting comprises passing the at least one filament through the catheter to a point where the second longitudinal end of the first filament extends from the second longitudinal end of the catheter and an end of the stump is adjacent the first longitudinal end of the catheter, wherein the pulling comprises pulling the repair device, first stump, and catheter simultaneously as a unit, wherein the passing comprises passing an elongate guide member between the first opening and the second opening, passing the catheter over the guide member between the first opening and the second opening; and subsequently removing the guide member, wherein the catheter comprises a dilation catheter comprising a tube having a lumen, the tube having a plurality of consecutive longitudinal segments, each consecutive longitudinal segment having an outer diameter over a majority of its length greater than an outer diameter of a preceding longitudinal segment, and wherein the passing comprises:

dilating the anatomical passage by passing the catheter through the anatomical passage starting with a smallest one of the longitudinal segments until a certain one of the longitudinal segments of the catheter dilates the anatomical passage a desired amount.

5. The method of claim 4 wherein each longitudinal segment is longer than the anatomical passage the catheter is intended to traverse and wherein the passing comprises positioning the certain one of the longitudinal segments so that it entirely occupies the anatomical passage between the first opening and the second opening.

6. The method of claim 5 wherein the passing further comprises removing the longitudinal segments other than the certain one of the longitudinal segments from the catheter after the positioning.

7. The method of claim 6 wherein the removing comprises cutting the catheter.

8. The method of claim 6 further comprising:
attaching a bone anchor to a bone;
removing the first repair device from the catheter; and
attaching the first repair device to the bone anchor.

9. The method of claim 8 wherein the attaching the first repair device to the bone anchor comprises attaching the at least one filament to the bone anchor.

10. The method of claim 8 wherein the bone anchor comprises an eyelet and the attaching the first repair device to the bone anchor comprises threading the at least one filament of the first repair device through the eyelet of the bone anchor.

11. The method of claim 4 wherein the pulling comprises:
pulling the repair device, catheter, and first stump simultaneously as a unit through the anatomical passage.

12. The method of claim 11 wherein the pulling further comprises:
pulling the unit through the anatomical passage until the stump is adjacent an entry to the anatomical passage;
positioning a funnel member having a smaller longitudinal end and a larger longitudinal end with the smaller longitudinal end adjacent the entry to the anatomical passage;
placing the first stump in the funnel member; and
pulling the unit to cause the stump to slide through the funnel member into the anatomical passage.

13. A method of retrieving through an anatomical passage a first stump of a longitudinal anatomical feature for reattachment to another anatomical feature, the method comprising:
providing a first repair device having a first longitudinal end and a second longitudinal end, the first repair device including at least one filament having a first longitudinal end defining the first longitudinal end of the first repair device and a second longitudinal end defining the second longitudinal end of the first repair device, a first needle attached to the first end of the at least one filament,
retrieving the first stump through a first opening in a patient,
stitching the at least one filament to the first stump using the first needle,
passing a catheter having a first longitudinal end and a second longitudinal end through the anatomical passage between the first opening and a second opening,
inserting at least the second longitudinal end of the at least one filament of the first repair device into the catheter from the first opening,
pulling the catheter, the first repair device, and the first stump attached to the first repair device from the second opening,
removing the first repair device from the catheter,
attaching the first repair device to a second stump of the longitudinal anatomical feature,
wherein the first repair device further comprising a second needle attached to the second end of each of the at least one filament, and wherein the attaching the first repair device to the second stump of the longitudinal anatomical feature comprises stitching the at least one filament to the second stump.

14. A method of retrieving through an anatomical passage a first stump of a longitudinal anatomical feature for reattachment to another anatomical feature, the method comprising:
providing a first repair device having a first longitudinal end and a second longitudinal end, the first repair device including at least one filament having a first longitudinal end defining the first longitudinal end of the first repair device and a second longitudinal end defining the second longitudinal end of the first repair device, a first needle attached to the first end of the at least one filament;
retrieving the first stump through a first opening in a patient
stitching the at least one filament to the first stump using the first needle;
passing a catheter having a first longitudinal end and a second longitudinal end through the anatomical passage between the first opening and a second opening;
inserting at least the second longitudinal end of the at least one filament of the first repair device into the catheter from the first opening; and pulling the catheter, the first repair device, and the first stump attached to the first repair device from the second opening, providing a bone anchor comprising at least one filament having a first longitudinal end attached to the bone anchor and a second longitudinal end bearing a needle;

attaching the bone anchor to a bone;

passing the at least one filament of the bone anchor through a second stump of the longitudinal anatomical feature;

pulling the first stump toward the second stump so that the ends of the first and second stumps abut;

stitching the first repair device to the second stump; and stitching the at least one filament of the bone anchor to the first stump using the needle of the bone anchor.

* * * * *